US012599673B2

(12) United States Patent
Hedrick et al.

(10) Patent No.: US 12,599,673 B2
(45) Date of Patent: Apr. 14, 2026

(54) TECHNIQUES FOR ENHANCING THE SELECTIVITY AND EFFICACY OF ANTIMICROBIAL AND ANTICANCER POLYMER AGENTS

(71) Applicants: International Business Machines Corporation, Armonk, NY (US); Agency for Science, Technology and Research, Singapore (SG)

(72) Inventors: James L. Hedrick, Pleasanton, CA (US); Nathaniel H. Park, San Jose, CA (US); Yi Yan Yang, Singapore (SG); Zhi Xiang Voo, Singapore (SG)

(73) Assignees: INTERNATIONAL BUSINESS MACHINES CORPORATION, Armonk, NY (US); Agency for Science, Technology and Research, Singapore (SG)

( * ) Notice: Subject to any disclaimer, the term of this patent is extended or adjusted under 35 U.S.C. 154(b) by 1210 days.

(21) Appl. No.: 17/470,121

(22) Filed: Sep. 9, 2021

(65) Prior Publication Data

US 2021/0401995 A1 Dec. 30, 2021

Related U.S. Application Data

(62) Division of application No. 16/201,155, filed on Nov. 27, 2018, now Pat. No. 11,167,036.

(51) Int. Cl.

| | |
|---|---|
| ***A61K 47/59*** | (2017.01) |
| ***A61K 31/155*** | (2006.01) |
| ***A61K 31/4188*** | (2006.01) |
| ***A61K 47/55*** | (2017.01) |

(52) U.S. Cl.

CPC ............ *A61K 47/59* (2017.08); *A61K 31/155* (2013.01); *A61K 31/4188* (2013.01); *A61K 47/55* (2017.08); *A61K 47/551* (2017.08)

(58) Field of Classification Search

CPC ...... A61K 47/59; A61K 47/55; A61K 47/551; A61K 31/155; A61K 31/4188

See application file for complete search history.

(56) References Cited

U.S. PATENT DOCUMENTS

| | | | | |
|---|---|---|---|---|
| 7,329,638 | B2 | 2/2008 | Yang et al. | |
| 8,709,483 | B2 | 4/2014 | Farokhzad et al. | |
| 11,007,216 | B2 * | 5/2021 | Hedrick | A61K 31/765 |
| 11,167,036 | B2 | 11/2021 | Hedrick et al. | |
| 2005/0059031 | A1 | 3/2005 | Bruchez et al. | |
| 2007/0053934 | A1 | 3/2007 | Kallenbach et al. | |
| 2010/0280219 | A1 * | 11/2010 | Cooley | C08G 64/0225 549/228 |
| 2014/0301968 | A1 | 10/2014 | Coady et al. | |
| 2016/0338356 | A1 * | 11/2016 | Chin | C08G 64/0241 |

FOREIGN PATENT DOCUMENTS

| | | | |
|---|---|---|---|
| WO | 2006/023207 | A2 | 3/2006 |

OTHER PUBLICATIONS

Muhammad (Chemical Communication, 2017, 53, 9971-9974) (Year: 2017).*

Velasco et al., "Comparative Study of Clinical Characteristics of Neutropenic and Non-Neutropenic Adult Cancerpatients with Bloodstream Infections", European Journal of Clinical Microbiology & Infectious Diseases , vol. 25, 2006, pp. 1-7.

Wang et al., "Biodegradable Functional Polycarbonate Micelles for Controlled Release of Amphotericin B", Acta Biomaterialia, Jul. 12, 2016, 10 pages.

Weiss et al., "Macrophage Defense Mechanisms Against Intracellular Bacteria", Immunological Reviews, vol. 264, 2015, pp. 182-203.

Wong et al., "Bactericidal and Virucidal Ultrathin Films Assembled Layer by Layer from Polycationic N-alkylated Polyethylenimines and Polyanions", Biomaterials, 2010, vol. 31, pp. 4079-4087.

Yang et al., "The Role of Non-covalent Interactions in Anticancer Drug Loading and Kinetic Stability of Polymeric Micelles", Biomaterials, vol. 33, 2012, pp. 2971-2979.

Zhang et al., "Antimicrobial Metallopolymers and their Bioconjugates with Conventional Antibiotics Against Multidrug-resistant Bacteria", Journal of the American Chemical Society, vol. 136, 2014, pp. 4873-4876.

Kim et al., "Synthesis and Evaluation of Biotin-conjugated pH-responsive Polymeric Micelles as Drug Carriers", Int J Pharm, vol. 427, No. 2, May 10, 2012, pp. 435-442, doi: 10.1016/j.ijpharm.2012.01.034, Epub, Feb. 7, 2012, 1 page.

Minko et al., "Enhancing the Anticancer Efficacy of Camptothecin Using Biotinylated Poly (Ethylene Glycol) Conjugates in Sensitive and Multidrug-resistant Human Ovarian Carcinoma Cells", Cancer Chemother Pharmacology, vol. 50, No. 2, Aug. 2002, pp. 143-150, Epub Jun. 11, 2002, 2 pages.

Ramathan et al., "Targeted PEG-based Bioconjugates Enhance the Cellular Uptake and Transport of a HIV-1 TAT Nonapeptide", Journal of Controlled Release, vol. 77, No. 3, Dec. 13, 2001, 1 page.

Walker et al., "Biotinylation Facilitates the Uptake of Large Peptides by *Escherichia coli* and Other Gram-negative Bacteria", Applied and Environmental Microbiology, vol. 71, No. 4, Apr. 2005, pp. 1850-1855.

(Continued)

*Primary Examiner* — Alma Pipic

(74) *Attorney, Agent, or Firm* — Amin, Turocy & Watson, LLP

(57) ABSTRACT

The subject disclosure is directed to techniques for enhancing the selectivity and efficacy of therapeutic polymers against a broad spectrum of pathogens and cancer cell lines. According to an embodiment, a method is provided that comprises forming a therapeutic polymer based on polymerization of a plurality of therapeutic monomers, wherein the therapeutic polymer provides a therapeutic functionality. The method further comprises attaching biotin to the therapeutic polymer, resulting in a biotin-functionalized therapeutic polymer, wherein the biotin-functionalized therapeutic polymer provides greater therapeutic efficacy relative to the therapeutic polymer.

19 Claims, 34 Drawing Sheets

(56) References Cited

OTHER PUBLICATIONS

Attia et al., "The Effect of Kinetic Stability on Biodistribution and Anti-tumor Efficacy of Drug-loaded Biodegradable Polymeric Micelles", Biomaterials, vol. 34, 2013, pp. 3132-3140.
Belon et al., "Intramacrophage Survival for Extracellular Bacterial Pathogens: Mgtc as a Key Adaptive Factor", Frontiers in Cellular and Infection Microbiology, vol. 61, No. 52, May 17, 2016, 5 pages.
Belon et al., "Intracellular Phase for an Extracellular Bacterial Pathogen: Mgtc Shows the Way", Microbial Cell, vol. 2, No. 9, Sep. 2015, 3 pages.
Buyck et al., "RX-P873, a Novel Protein Synthesis Inhibitor, Accumulates in Human THP-1 Monocytes and is Active against Intracellular Infections by Gram-positive (*Staphylococcus aureus*) and Gram-negative (Pseudomonas aeruginosa) Bacteria", Antimicrobial Agents and Chemotherapy, vol. 59, No. 8, Aug. 2015, pp. 4750-4758.
Cheng et al., "Broad-spectrum Antimicrobial/Antifouling Soft Material Coatings using Poly(elhylenimine) as a Tailorable Scaffold", Biomacromolecules, Jun. 3, 2015, 35 pages.
Chin et al., "Biodegradable Broad-spectrum Antimicrobial Polycarbonates: Investigating the Role of Chemical Structure on Activity and Selectivity", Macromolecules, vol. 46, 2013, pp. 8797-8807.
Chin et al., "A Macromolecular Approach to Eradicate Multidrug Resistant Bacterial Infections while Mitigating Drug Resistance Onset", Nature Communications, vol. 9, No. 917, Mar. 2, 2018, 14 pages.
Coady et al., "Enhancement of Cationic Antimicrobial Materials via Cholesterol Incorporation", Advance Healthcare Materials, vol. 3, 2014, pp. 882-889.
Cooley et al., "Oligocarbonate Molecular Transporters: Oligomerization-Based Syntheses and Cell-Penetrating Studies", Journal of the American Chemical Society, vol. 131, No. 45, 2009, pp. 16401-16403.
Engler et al., "The Synthetic Tuning of Clickable pH Responsive Cationic Polypeptides and Block Copolypeptides", Soft Matter, vol. 7, 2011, pp. 5627-5637.
Engler et al., "Polycarbonate-Based Brush Polymers with Detachable Disulfide-Linked Side Chains", ACS Macro Letters, vol. 2, 2013, pp. 332-336.
Engler et al., "Antimicrobial Polycarbonates: Investigating the Impact of Balancing Charge and Hydrophobicity Using a Same-Centered Polymer Approach", Biomacromolecules, Aug. 19, 2013, 9 pages.
Feng et al., "Construction of Functional Aliphatic Polycarbonates for Biomedical Applications", Progress in Polymer Science, vol. 37, 2012, pp. 211-236.
Fukushima et al., "Broad Spectrum Antimicrobial Supramolecular Assemblies with Distinctive Size and Shape", American Chemical Society NANO, vol. 6, No. 10, 2012, pp. 9191-9199.
Gabriel et al., "Synthetic Mimic of Antimicrobial Peptide with Nonmembrane-Disrupting Antibacterial Properties", Biomacromolecules, vol. 9, No. 11, 2008, pp. 2980-2983.
Gootz, T. D., "The Global Problem of Antibiotic Resistance", Critical Reviews in Immunology, vol. 30, No. 1, 2010, 2 pages.
Han et al., "Polymer/Peptide Complex-Based Sensor Array Discriminates Bacteria in Urine", Angenwandte Chemie International Edition, 2017, 7 pages.
Hidron et al., "Infection Control and Hospital Epidemiology", Chicago Journals, vol. 30, No. 1, Jan. 2009, 2 pages.
Ichiyama et al., "Cooperative Orthogonal Macromolecular Assemblies with Broad Spectrum Antiviral Activity, High Selectivity, and Resistance Mitigation", Macromolecules, vol. 49, 2016, pp. 2618-2629.
Ikler et al., "Tuning the Hemolytic and Antibacterial Activities of Amphiphilic Polynorbornene Derivatives", Journal of the American Chemical Society, vol. 126, 2004, pp. 15870-15875.
Insua et al., "Enzyme-responsive Polyion Complex (PIC) Nanoparticles for the Targeted Delivery of Antimicrobial Polymers", Polymer Chemistry, Jan. 26, 2016, 7 pages.
Kharazmi, A., "Mechanisms Involved in the Evasion of the Host Defence by Pseudomonas aeruginosa", Immunology Letters, vol. 30, 1991, pp. 201-206.
Kuroda et al., "Amphiphilic Polymethacrylate Derivatives as Antimicrobial Agents", Journal of the American Chemical Society, vol. 127, 2005, pp. 4128-4129.
Lee et al., "Block Copolymer Mixtures as Antimicrobial Hydrogels for Biofilm Eradication", Biomaterials, vol. 34, 2013, pp. 10278-10286.
Li et al., "Broad-Spectrum Antimicrobial and Biofilm-Disrupting Hydrogels: Stereocomplex-Driven Supramolecular Assemblies", Angenwandte Chemie International Edition, vol. 52, 2013, pp. 674-678.
Liu et al., "Nontoxic Membrane-Active Antimicrobial Arylamide Oligomers", Angewandte Chemie International Edition, vol. 116, 2004, pp. 1178-1182.
Lyczak et al., "Establishment of Pseudomonas aeruginosa Infection: Lessons From a Versatile Opportunist", Microbes and Infection, vol. 2, 2000, pp. 1051-1060.
Marr et al., "Antibacterial Peptides for Therapeutic Use: Obstacles and Realistic Outlook", Current Opinion in Pharmacology, vol. 6, 2006, pp. 468-472.
Mittal et al., "Otopathogenic Pseudomonas aeruginosa Enters and Survives Inside Macrophages", Frontiers in Microbiology, vol. 7, No. 1828, Nov. 2016, 15 pages.
Ng et al., "Synergistic Co-Delivery of Membrane-Disrupting Polymers with Commercial Antibiotics against Highly Opportunistic Bacteria", Advanced Materials, vol. 25, 2013, pp. 6730-6736.
Ng et al., "Antimicrobial Polycarbonates: Investigating the Impact of Nitrogen-Containing Heterocycles as Quaternizing Agents", Macromolecules, Dec. 26, 2013, 7 pages.
Lienkamp et al., "Antimicrobial Polymers Prepared by ROMP with Unprecedented Selectivity: A Molecular Construction Kit Approach", Journal of the American Chemical Society, vol. 130, No. 30, Jul. 30, 2008, pp. 9836-9843.
Ong et al., "Design and Synthesis of Biodegradable Grafted Cationic Polycarbonates as Broad Spectrum Antimicrobial Agents", Journal of Polymer Science, Part A: Polymer Chemistry, vol. 54, 2016, pp. 1029-1035.
Rada et al., "Interactions between Neutrophils and Pseudomonas aeruginosa in Cystic Fibrosis", Pathogens, vol. 6, 2017, 24 pages.
Percival et al., "HCAI, Medical Devices and Biofilms: Risk, Tolerance and Control", Journal of Medical Microbiology, Feb. 10, 2015, 31 pages.
Pratt et al., "Exploration, Optimization, and Application of Supramolecular Thiourea-Amine Catalysts for the Synthesis of Lactide (Co)polymers", Macromolecules, vol. 39, 2006, pp. 7863-7871.
Pratt et al., "Tagging Alcohols With Cyclic Carbonate: a Versatile Equivalent of (Meth)acrylate for Ring-Opening Polymerization", Chemical Communications, 2008, pp. 114-116.
Qiao et al., "Highly Dynamic Biodegradable Micelles Capable of Lysing Gram-positive and Gram-negative Bacterial Membrane", Biomaterials, vol. 33, 2012, pp. 1146-1153.
Ruden et al., "Synergistic Interaction between Silver Nanoparticles and Membrane-permeabilizing Antimicrobial Peptides", Antimicrobial Agents and Chemotherapy, vol. 53, No. 8, Aug. 2009, pp. 3538-3540.
Tan et al., "Broad Spectrum Macromolecular Antimicrobials with Biofilm Disruption Capability and In Vivo Efficacy", Advanced Healthcare Materials, 1601420, 2017, 9 pages.
Tempelaar et al., "Synthesis and Post-polymerisation Modifications of Aliphatic Poly(Carbonate)s Prepared by Ring-opening Polymerisation", Chemical Society Reviews, 2012, 24 pages.
Tew et al., "De novo Design of Biomimetic Antimicrobial Polymers", Proceedings of the National Academy of Sciences, vol. 99, No. 8, Apr. 16, 2002, pp. 5110-5114.
Tra et al., "Glycans in Pathogenic Bacteria—Potential for Targeted Covalent Therapeutics and Imaging Agents", Chemical Communication, vol. 50, 2014, pp. 4659-4673.

(56) References Cited

OTHER PUBLICATIONS

Tynan et al., "Macrophage Migration Inhibitory Factor Enhances Pseudomonas aeruginosa Biofilm Formation Potentially Contributing to Cystic Fibrosis Pathogenesis", The FASEB Journal, vol. 31, Aug. 2017, 10 pages.
Yang et al., "Supramolecular Nanostructures Designed for High Cargo Loading Capacity and Kinetic Stability", Nano Today, vol. 5, 2010, pp. 515-523.
Non-Final Office Action received for U.S. Appl. No. 16/201,155 dated Jan. 28, 2021, 46 pages.
United States Notice of Allowance dated Jun. 30, 2021, 10 pages, in U.S. Appl. No. 16/201,155.
United States Requirement for Restriction/Election dated Sep. 21, 2020, 11 pages in U.S. Appl. No. 16/201,155.

* cited by examiner

Formula 2 - BG

Formula 4

TEM of Complex E

900

Anionic Polymer A Formation

Biotinylated Anionic Polymer A' Formation

901

Polymer A'

Biotinylated Anionic Polymer J' Formation

Functional Guanidinium Cationic Homopolymers

1200

Coacervate Characteristics

| Polymers | Particle Size (nm) | PDI | Zeta Potential (mV) |
|---|---|---|---|
| PEG5K-30rp$SO_3H$ with Polymyxin B (PolB) | 168 ± 4 | 0.07 ± 0.04 | -0.19 ± 1.2 |
| PEG10K-15rp$SO_3H$ with PolB | 165 ± 4 | 0.29 ± 0.01 | 0.34 ± 0.2 |
| PEG10K-30rp$SO_3H$ (Polymer A) with PolB | 135 ± 3 | 0.17 ± 0.02 | -2.5 ± 0.4 |
| PEG10K-15rp$SO_3H$ with Polymer B | 113 ± 1 | 0.09 ± 0.02 | 3.6 ± 0.9 |
| Polymer A with Polymer B (Complex B) | 132 ± 1 | 0.08 ± 0.04 | 5.3 ± 0.4 |
| PEG10K-15rp$SO_3H$ with Polymer C | 106 ± 4 | 0.18 ± 0.02 | 4.8 ± 0.2 |
| Polymer A with Polymer C (Complex C) | 117 ± 1 | 0.11 ± 0.04 | 3.4 ± 0.2 |
| PEG10K-15rp$SO_3H$ with Polymer D | 159 ± 6 | 0.08 ± 0.01 | 3.7 ± 1.0 |
| Polymer A with Polymer D (Complex D) | 138 ± 3 | 0.07 ± 0.02 | 0.1 ± 0.7 |
| PEG10K-15rp$SO_3H$ with Polymer E | 95 ± 2 | 0.06 ± 0.01 | -0.8 ± 1.7 |
| Polymer A with Polymer E (Complex E) | 82 ± 1 | 0.08 ± 0.02 | -0.01 ± 0.3 |
| Polymer A-Biotin with Polymer E (Complex E') | 71 ± 1 | 0.09 ± 0.02 | -1.6 ± 0.4 |

Efficacy and Selectivity of Therapeutic Polymers and Coacervate Complexes Against P. aeruginosa

| Polymers | Polymer Composition | MIC (μg/mL) | $HC_{50}$ | SI[c] |
|---|---|---|---|---|
| | | *P. aeruginosa* | (μg/mL) | [HC50 (μg/mL)/MIC (μg/mL)] |
| Polymer A | MPEG 10 kDa-$P(SO_3H)_{38}$ | N.D. | > 2500[a] | N.D. |
| Polymer B | 4MBA-$P(Gua)_{16}$ | 31.3 | > 2500[a] | > 80 |
| Complex B | MPEG 10 kDa-$P(SO_3H)_{38}$ + 4MBA-$P(Gua)_{16}$ | 62.5 | > 2500[a] | > 80 |
| Polymer C | DM-$P(Gua)_{16}$ | 15.6 | > 2500[a] | > 160 |
| Complex C | MPEG 10 kDa-$P(SO_3H)_{38}$ + DM-$P(Gua)_{16}$ | 15.6 | > 2500[a] | > 160 |
| Polymer D | 4MBA-$P(Gua)_{16}$-$P(Urea)_2$ | 62.5 | 1000 | 16 |
| Complex D | MPEG 10 kDa-$P(SO_3H)_{38}$ + 4MBA-$P(Gua)_{16}$-$P(Urea)_2$ | 125 | > 2500[a] | > 40 |
| Polymer E | DM-$P(Gua)_{16}$-$P(Urea)_2$ | 15.6 | 500 | 32.1 |
| Complex E | MPEG 10 kDa-$P(SO_3H)_{38}$ + DM-P(Gua)16-P(Urea)2 | 31.25 | > 2500[a] | > 160 |
| PolB | Polymyxin B sulfate | 0.5 | N.D. | N.D. |
| Complex X | MPEG 10 kDa-$P(SO_3H)_{38}$ + PolB | 0.5 | N.D. | N.D. |

Characteristics of Coacervate Complexs HJ at Varying DP

| Cationic Polymer | Anionic Polymer | Molar Ratio (Anionic: Cationic) | Particle Size (d.nm) | PDI (Đ) | Zeta Potential (mV) | MIC (μg/mL) |
|---|---|---|---|---|---|---|
| Polymer H | Polymer J (n = 10) | 0.5 : 1 | 164 ± 31 | 0.49 ± 0.04 | 8.9 ± 0.7 | - |
| | | 1 : 1 | 119 ± 20 | 0.50 ± 0.02 | 11.5 ± 2.2 | 15.6 |
| | | 2 : 1 | 27 ± 1 | 0.32 ± 0.04 | 0.2 ± 1.9 | 15.6 |
| | Polymer J (n = 20) | 0.5 : 1 | 34 ± 1 | 0.22 ± 0.03 | 11.4 ± 1.2 | 15.6 |
| | | 1 : 1 | 32 ± 1 | 0.07 ± 0.04 | - 2.5 ± 2.4 | 15.6 |
| | | 2 : 1 | 32 ± 1 | 0.13 ± 0.02 | - 13.5 ± 5.7 | > 250 |
| | Polymer J (n = 20) | 0.5 : 1 | 36 ± 2 | 0.16 ± 0.05 | 12.5 ± 0.1 | 250 |
| | | 1 : 1 | 35 ± 1 | 0.15 ± 0.04 | -11.4 ± 1.4 | > 250 |
| | | 2 : 1 | 35 ± 1 | 0.10 ± 0.01 | -11.6 ± 0.1 | > 250 |

*MIC of Polymer H alone = 7.8 g/mL.*

In Vivo Toxicity

| Antimicrobials | LD50 (mg/kg) |
|---|---|
| Polymyxin B (PolB) | 5.4 |
| Polymer E | 17.5~50 |
| Complex H (PolB+ Polymer A) | 5.4 |
| Complex E | >175 (aggregation appearing above this concentration) |

Antimicrobial In Vivo Efficacy

| Formulation | Dose (mg/kg) |
|---|---|
| Complex E | Unable to treat at 42.2, mice dead at 84.4 |
| Complex E' | Infected mice survived at 42.2 |

TECHNIQUES FOR ENHANCING THE SELECTIVITY AND EFFICACY OF ANTIMICROBIAL AND ANTICANCER POLYMER AGENTS

TECHNICAL FIELD

This application generally relates to techniques for enhancing the selectivity and efficacy of therapeutic polymers against a broad spectrum of pathogens and cancer cell lines.

BACKGROUND

Nosocomial Gram negative bacteria *Pseudomonas aeruginosa* (*P. aeruginosa*) infections have high adaptability and strong antibiotics resistance. In addition, these bacteria have the ability to form biofilms, which further increases its resistance to a broad spectrum of antibiotics. As a result, hospital acquired *P. aeruginosa* infections account for high morbidity rates. *P. aeruginosa* infections are also the most commonly acquired infection among patients with cystic fibrosis and chronic obstructive pulmonary disease (COPD). Phagocytes such as neutrophils and macrophages are responsible for eradicating intracellular bacteria via acidic/oxidative stresses, build-up of metal in the phagolysosome, limiting its availability of key nutrients (fatty acids and iron) to phagocytosed bacteria. However, *P. aeruginosa* has devised mechanisms to evade the innate immune system and ingestion by macrophages. To compound the problem, *P. aeruginosa* was recently shown to survive and thrive within the macrophages by employing various gene mutations that prevent elimination within the hostile environment during phagocytosis. An example, is the inhibitory effect of MgtC on adenosine triphosphate (ATP) synthase activity, enabling *P. aeruginosa* to withstand metabolic dysregulation during the acidification of the phagosome. In addition, the outer membrane protein of *P. aeruginosa* plays a critical role for its survival within the macrophage. Finally, *P. aeruginosa* have also been found within phagocytic cells (alveolar macrophages) of infected mice. Incomplete clearance of *P. aeruginosa* from these infected phagocytic cells will ultimately lead to infection of other cell types, starting with dissemination from the original site of infection, affecting especially immunocompromised patients. Moreover, *P. aeruginosa* was shown to recruit extracellular deoxyribonucleic acid (DNA) and migratory inhibition factors from neutrophils, promoting the growth of biofilm. The biofilm is an extracellular matrix for the bacteria to reside within, shielding the colonies from antibiotics and causing chronic infections.

To circumvent bacteria resistance and intracellular infection of macrophages, polyguanidines with transmembrane and highly effective antimicrobial properties have been employed to treat *P. aeruginosa* infection. Unlike traditional antibiotics and various synthetic antimicrobial polymers and antimicrobial peptides which do not enter the bacteria, the polyguanidiniums are cationic polymers which possess amphiphilicity (balance between hydrophobicity and soluble positive charges). In this regard, the polyguanidiniums damage microbes via membrane lysis resulting from electrostatic attraction between positive polymer charges and negative membrane surface of microbes or via trans-location across the membrane leading to cytosol precipitation. Currently, polymers with varying non-degradable backbones such as polyethylenimines polyacrylates, polynorbornene, polyarylamides and metallopolymers have been reported and studied for their antimicrobial properties. However, the non-degradability properties of these polymers pose an issue of low selectivity and high hemotoxicity to mammalian cells. Conversely, antimicrobial peptides (degradable polypeptide backbone) are limited in their clinical applications due to cytotoxicity, enzymatic degradation and high production cost.

In order to synthesize a low cost, well defined biodegradable synthetic antimicrobial polymer, an organocatalytic ring opening polymerization (OROP) technique has been employed to attain aliphatic polycarbonates that possess low toxicity and biocompatibility. In addition, monomers of various functionalities can be easily incorporated into synthesis of these antimicrobial polycarbonates and are well characterized due to the precise control of the OROP. This allowed for design of various antimicrobial macromolecules, with the "same centered" design approach shown more recently to provide a distinctive combination of both antimicrobial activity and selectivity properties. However, increasing the hydrophobicity on the "same centered" guanidinium-functionalized polycarbonates did not significantly improve antimicrobial activity and reduced selectively in certain instances.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. The subject disclosure relates to techniques for enhancing the selectivity and efficacy of therapeutic polymers against a broad spectrum of pathogens and cancer cell lines.

According to an embodiment, a method is provided that comprises forming a therapeutic polymer based on polymerization of a plurality of therapeutic monomers, wherein the therapeutic polymer provides a therapeutic functionality. The method further comprises attaching biotin to the therapeutic polymer, resulting in a biotin-functionalized therapeutic polymer, wherein the biotin-functionalized therapeutic polymer provides greater therapeutic efficacy relative to the therapeutic polymer.

In various implementations, the biotin-functionalized therapeutic polymer provides the greater therapeutic efficacy based on increased uptake of the biotin-functionalized therapeutic polymer by pathogens or cancer cells relative to the therapeutic polymer. In particular, the biotin-functionalized therapeutic polymer can provide the greater therapeutic efficacy based on reduced toxicity of the therapeutic polymer toward mammalian cells relative to the therapeutic polymer. In one or more implementations, the therapeutic functionality comprises an anticancer functionality. In other implementations, the therapeutic functionality comprises an antimicrobial functionality. In various implementations, the therapeutic polymer comprises polyguanidinium.

The techniques for attaching the biotin can vary. For example, in some implementations, the attaching comprises performing the polymerization of the plurality of therapeutic monomers in presence of biotinol, resulting in formation of the biotin-functionalized therapeutic polymer with the biotin bound to an end of the polymer backbone. In other implementations, the biotin can be attached via post polymerization modification.

In another embodiment, a therapeutic is polymer is provided comprising a polymer backbone, therapeutic functional groups bound to the polymer backbone, and a biotin-based functional group bound to an end of the polymer backbone. For example, in one or more implementations the biotin-based functional group can comprise biotinol. In various implementations, the therapeutic functional groups comprise guanidinium moieties. In some implementations, the therapeutic polymer facilitates necrosis of bacteria cells. In other implementations, the therapeutic polymer facilitates autophagy of cancer cells.

In some implementations, the therapeutic polymer has a chemical structure characterized by Formula I:

Formula I

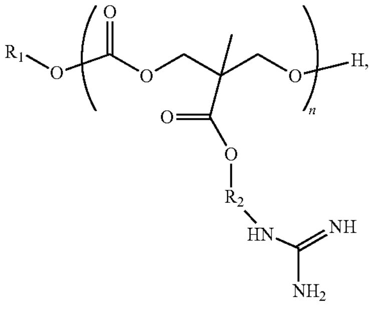

wherein n represents an integer between 10 and 50, wherein $R_1$ comprises the biotin-based functional group, and wherein $R_2$ comprises a spacer group.

In another implementation, the therapeutic polymer has a chemical structure characterized by Formula II:

Formula II

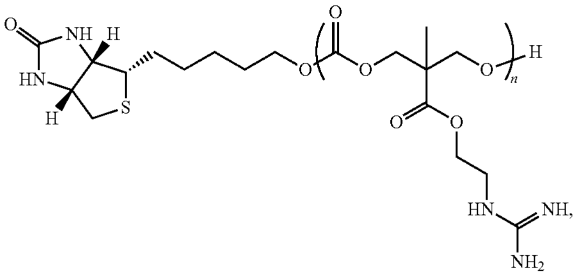

wherein n represents an integer between 10 and 50,

In another implementation, the therapeutic polymer has a chemical structure characterized by Formula III:

Formula III

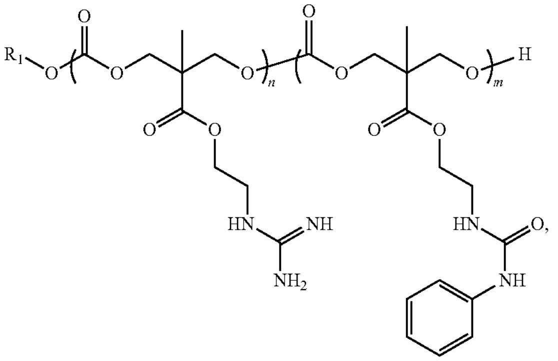

wherein n represents an integer between 10 and 50, wherein m represents an integer between 1.0 and 10, and wherein $R_1$ comprises the biotin-based functional group.

In yet another implementation, the therapeutic polymer has a chemical structure characterized by Formula IV:

Formula IV

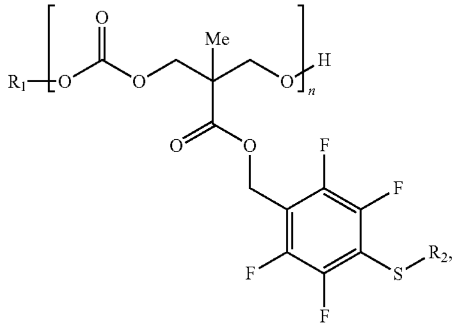

wherein n represents an integer between 10 and 50, wherein $R_1$ comprises a functional group, and wherein $R_2$ comprises the biotin-based functional group.

In one or more additional embodiments, a therapeutic polymer is provided that has a chemical structure characterized by Formula I:

Formula I

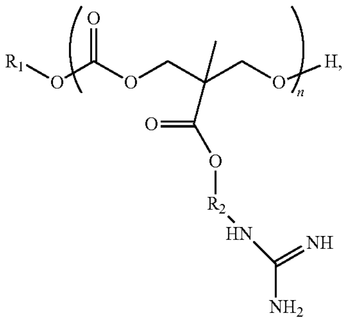

wherein n represents an integer between 10 and 50, wherein $R_1$ comprises the biotin-based functional group, and wherein $R_2$ comprises a spacer group.

In some implementations, the therapeutic polymer is an anticancer agent. In other implementations, the therapeutic polymer is an antimicrobial agent.

In another embodiment, an anticancer agent is described that has a chemical structure characterized by Formula I:

Formula I

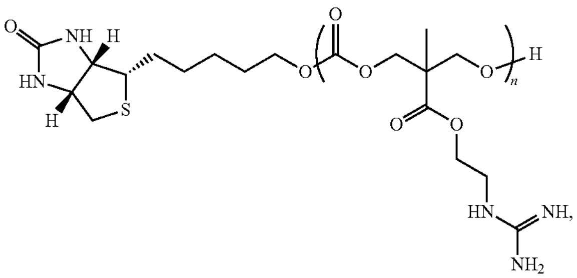

wherein n represents an integer between 10 and 50, and where the anticancer agent is effective against a plurality of different cancer cell lines. In one or more implementations, the plurality of different cancer cell lines comprises cancer cell line BT-474.

One or more additional embodiments are directed to a method that comprises polymerizing guanidinium-functionalized cyclic carbonate monomers via a ring opening polymerization reaction using biotinol as an initiator. The method further comprises forming a biotinylated polyguanidinium macromolecule based on the polymerizing. In various embodiments, the biotinylated polyguanidinium provides antimicrobial and anticancer functionality.

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which:

FIG. 12 provides a table identifying characteristics of example therapeutic coacervates in accordance with various embodiments described herein.

FIG. 15B provides a table illustrating the antimicrobial selectivity and efficacy of example therapeutic polymers and coacervate complexes against *P. aeruginosa* in accordance with various embodiments described herein.

FIG. 16 presents a table illustrating characteristics of example coacervate Complexes HJ with varying degrees of polymerization (DP) in accordance with various embodiments described herein.

FIGS. 21A and 21B provide tables illustrating the in vivo toxicity and antimicrobial efficacy of coacervate complexes in accordance with various embodiments described herein.

DETAILED DESCRIPTION

Figure 1:
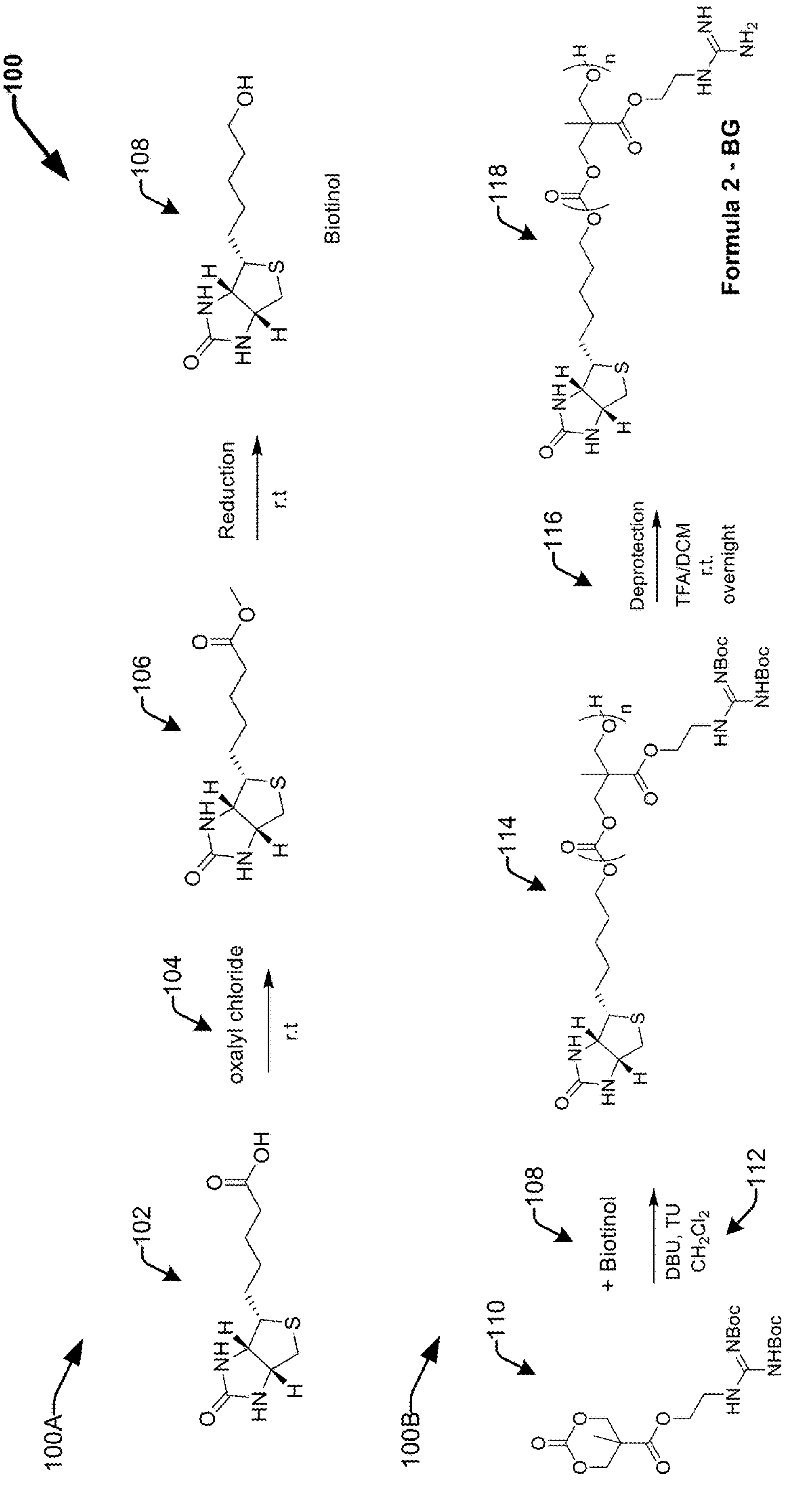
FIG. 1 presents an example synthesis route 100 for generating a biotinylated polyguanidinium in accordance with various embodiments described herein.

The following detailed description is merely illustrative and is not intended to limit embodiments and/or application or uses of embodiments. Furthermore, there is no intention to be bound by any expressed or implied information presented in the preceding Summary section or in the Detailed Description section.

The subject disclosure provides techniques for enhancing the antimicrobial selectivity and efficacy of aliphatic polymers, such as guanidinium-functionalized polycarbonates, against a broad spectrum of bacterial pathogens, including *P. aeruginosa*. Various embodiments of the disclosed techniques for enhancing the selectivity and efficacy of antimicrobial polymers are further extended to anticancer block polymers, providing techniques for enhancing the selectivity and efficacy of anticancer block polymers for a wide array of cancer cell lines.

The disclosed techniques take advantage of natural molecular trafficking mechanisms in cancer and pathogen derived diseases to enhance the efficacy of macromolecular therapeutics. In particular, the disclosed techniques employ unique methods to modify antimicrobial and anticancer polymers to target a broad spectrum of both pathogens and cancer cell lines and enhance the transport of the respective polymers through the bacterial cell and/or the cancer cell membrane. In various embodiments, similar materials/mechanisms can be used to modify both antimicrobial and anticancer polymers to enhance the selective uptake of these polymers into the bacteria and/or cancer cell and thereafter cause the respective cells to undergo necrosis or autophagy. For example, with respect to bacteria cells, in response to ingestion of the disclosed modified antimicrobial polymers by bacterial cells, the bacterial cells activate reactive oxygen species (ROS) which cause cellular necrosis. With respect to anticancer cells, in response to ingestion of the disclosed modified anticancer polymers by cancer cells, the anticancer polymers activate autophagy, thereby eliminating the exposed cancer cells.

In one or more embodiments, the uptake of polymer therapeutics in a broad spectrum of pathogens and cancer cells is enhanced via the introduction of biotin. The added biotin can also enhance the therapeutic activity of the polymers. In other embodiments, the selectivity of antimicrobial and anticancer polymers can be significantly enhanced by the introduction of an anionic polymer in combination with the cationic therapeutic polymer to form a coacervate. In this regard, an anionic polymer (optionally with functional groups) can be combined with the cationic therapeutic polymer to generate an electrostatic coacervate complex that is neutral and shields the toxic antimicrobial/anticancer cationic polymer when the complex circulates throughout the body, thereby reducing the toxicity of the cationic polymer to mammalian cells. These coacervate complexes are well-defined nanocomplexes that are highly modular with tunable particle size and neutral charge and remain stable under physiological conditions even in the presence of serum proteins. In some implementations, the anionic polymer and/or the cationic polymer can be functionalized with biotin to further increase the uptake of the coacervate complex by the pathogen and/or cancer cells. In one or more additional embodiments, these coacervate complexes can be used for diagnostic purposes. With these embodiments, the cationic polymer can be calibrated to target a specific pathogen or cancer cell type, and the anionic polymer and/or the cationic polymer can be functionalized with a fluorescent dye that illuminates in response to reaction of the coacervate with the specific pathogen or cancer cell type.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

I—Biotinylated Therapuetic Polymers

In one or more embodiments, antimicrobial and anticancer therapeutic polymers can be modified via functionalization with biotin (vitamin H) to facilitate the transport of these polymers through protein-based channels that traffic vitamins into bacteria as well as most cancer cell lines that over express such channels. In this regard, bacteria and cancer cells readily accept biotin as a source of food/fuel. By attaching biotin onto the therapeutic polymer, the bacteria/cancer cells are essentially enticed by the biotin and ingest the entire polymer via their normal protein-based channels. Once inside the cell, these antimicrobial/anticancer polymers initiate and/or facilitate killing of the cell.

As used herein, the term "biotinylated" refers to functionalization of a molecule, macromolecule, polymer, etc., with a biotin or biotin based functional group. In various embodiments, the antimicrobial and/or anticancer therapeutic polymers that are biotinylated in accordance with the disclosed techniques can include functional guanidinium polymers, referred to herein as polyguanidiniums. These polyguanidiniums can be formed using a controlled ROP of various cyclic carbonate monomers incorporating different antimicrobial and/or anticancer functionalities. These polyguanidiniums can comprise a hydrophobic polymer backbone consisting of one or more covalently bonded polymer units, wherein at least some (one or more) of the polymer units comprise a cationic (positively charged) guanidine-based functional group extending therefrom and covalently bonded to one or more atoms of the polymer unit via a spacer group. In this regard, the polymer backbone can comprise one or more repeat monomer units that are respectively functionalized with a cationic, guanidine-based antimicrobial/anticancer moiety. These monomers are referred to herein as guanidinium functionalized monomers. In various embodiments, the polyguanidiniums can be biotinylated via the attachment of biotin or a biotin based functional group (e.g., biotinol) to one or more ends or side chains of the polymer backbone. A polyguanidinium comprising a biotin or biotin based functional group is referred to herein as a biotinylated polyguanidinium (BG). In some embodiments, the biotin can be attached during ROP of the monomer used to generate the biotinylated polyguanidinium. In other embodiments, the biotin can be attached via post-polymerization modification of the biotinylated therapeutic polymer.

In various embodiments, the subject biotinylated polyguanidiniums can facilitate killing bacterial cells and/or cancer cells via membrane translocation facilitated in part by the cationic guanidinium-moiety and further enhanced by the biotin functional group. For example, in some implementation, when the disclosed biotinylated polyguanidinium are used as an antimicrobial agent, the cationic guanidinium moieties can bind with the anionic (negatively charged) phosphate groups on the bacterial cell membrane surface and a counterion exchange occurs between the guanidinium and the phosphate groups. As a result, the polymer becomes neutrally charged, allowing the polymer to translocate through the lipid bilayer of the bacterial membrane (e.g., as a non-polar species). The polymer is then released through the membrane leading to cytosol material precipitation and subsequent cell necrosis. In this regard, release of the polymer into the bacteria cytosol cause precipitation of the biomacromolecules inside the cell of the bacteria, including ribonucleic acid (RNA), deoxyribonucleic acid (DNA), proteins, enzymes, etc. and the cell begins to kill itself by generating reactive oxygen species (ROS) which cause cellular necrosis. The disclosed biotinylated polyguanidinium can perform a same or similar translocation mechanism attributed in part to the cationic guanidinium moiety to facilitate entry of the polymer into cancer cells. In response to ingestion of the biotinylated guanidinium polymers by cancer cells, the anticancer polymers activate autophagy, thereby eliminating the exposed cancer cells.

The biotin or biotin based functional group can further facilitate the translocation of the biotinylated polyguanidinium into the bacteria cell and/or cancer cell by taking advantage of natural molecular trafficking mechanisms in cancer and pathogen derived diseases. In particular, the biotin functional group opens up pore channels in both bacterial and cancer cells to facilitate increased uptake of the biotinylated polyguanidinium into the cell. In this regard, the biotin can in part serve as a molecular transporter. Based in the increased intracellular uptake of the biotinylated polyguanidiniums, the therapeutic activity and resistance prevention of the biotinylated polyguanidiniums are significantly enhanced.

In various embodiments, the antimicrobial and/or anticancer therapeutic polymers that are biotinylated in accordance with the disclosed techniques can include polyguanidiniums having chemical Formula 1 below, wherein $R_1$ comprises biotin or a biotin based functional group.

Formula 1

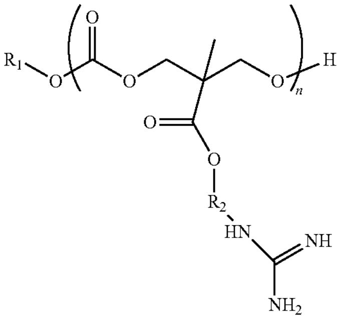

In accordance with Formal 1, the biotinylated polyguanidinium comprises a number "n" of repeating monomer units, (referred to herein as guanidinium functionalized monomer units or the monomer units). Each (or in some embodiments one or more) of the monomer units can comprise a polycarbonate group and a cationic guanidinium moiety attached to the polycarbonate a spacer group $R_2$. The spacer group $R_2$ can vary and can be adapted to facilitate a specific function or antimicrobial/antibacterial property of the polymer. For example, in some implementations the spacer group $R_2$ can be selected/adapted to target a specific pathogen or cancer cell type. In another example, the spacer group $R_2$ can comprise a group that causes the entire polymer to self-assemble into a micelle structure, wherein the cationic guanidinium portion of the polymer becomes shielded within the micelle structure. One suitable functional group that can facilitate this self-assembly can include a butyl group. Other suitable functional groups that can be employed for $R_2$ can include but are not limited to: an alkyl group, an ethyl group, an isopropyl group, a propyl group, a pentyl group, a cyclohexyl group, a phenyl group, and a benzyl group.

In various exemplary embodiments, the disclosed antimicrobial/anticancer biotinylated polyguanidiniums having Formula 1 can be or include a biotinylated polyguanidinium having Formula 2.

Formula 2

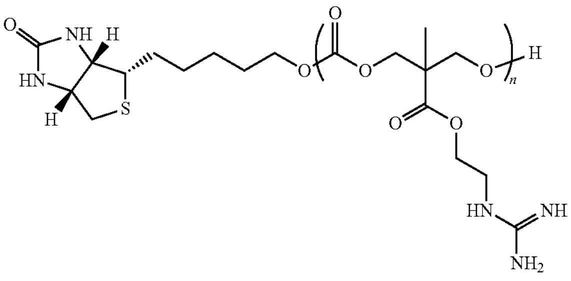

In accordance with Formula 2, the guanidinium moiety is attached to the polymer backbone via an alkyl $C_2$ spacer group (e.g., $R_2$=an alkyl group) and the biotin functional group $R_1$ comprises biotinol. In one or more embodiment, the chemical name for the polymer represented by Formula 2 is Biotinol-$[C2Gua]_{17}$.

In other embodiments, the disclosed antimicrobial/anticancer biotinylated polyguanidiniums can include block copolymers. For example, in one or more embodiments, having can be or include a biotinylated polyguanidinium copolymer having Formula 3, wherein $R_1$ comprises biotin or a biotin based functional group (e.g., biotinol) and wherein m=2 or 1<m<20.

Formula 3

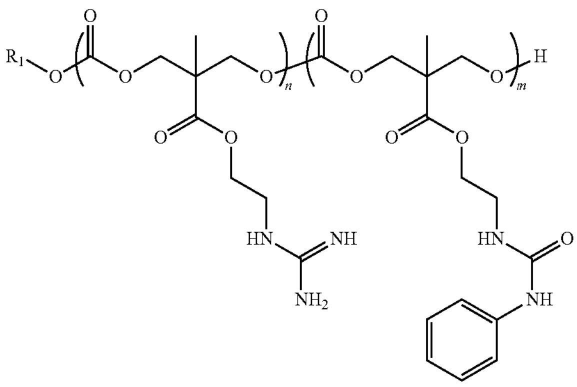

With reference to Formulas 1, 2 and 3 the number "n" and/or "m" of repeating and connected/bonded guanidinium functionalized monomer units can vary. For example, in some implementations, the number "n" of repeating monomer units can be one or more and one thousand or less. However, in various embodiments, the number "n" of repeating monomer units can be less than 50 and more preferably less than 40 to reduce the particle size of the polymer which facilitates better circulation and update in-vivo. In one implementation, the number "n" can be between 10 and 40 units. In another implementation, the number "n" can be between 10 and 40 units. With respect to Formula 3, in various embodiments, the number "m" can be less than the number "n". For example, in some implementations, the number "m" can be between 1.0 and 10.

In some implementations, the number "n" of repeating monomer units can be tailored to balance the hydrophobicity of the polymer backbone group and the spacer group $R_2$ relative to the hydrophilicity of the guanidinium moiety. In other implementation in which $R_2$ comprises a butyl group, the number "n" of repeating monomer units can be tailored to facilitate formation of the subject biotinylated polyguanidinium into protected micelle nanostructures in aqueous solution to facilitate the self-assembly of the subject polymers into the protected micelle nanostructures, wherein the guanidinium moieties are exposed on the outside of the micelle on the out and the hydrophobic residuals are internalized within a micelle. In this regard, in some embodiments, one or more polymers having Formula 1 can be configured to self-assemble into the protected micelle nanostructures when $R_2$ comprises a butyl group and "n" is between 10 and 50, and more preferably between 20 and 40.

FIG. 1 presents an example synthesis route 100 for generating a biotinylated polyguanidinium having chemical Formula 2 in accordance with various embodiments described herein. Synthesis route 100 facilitates the attachment of biotin to therapeutic polymers via the modification of biotin into an alcohol form, which is then repurposed as a polymerization initiator. In this regard, synthesis route 100 facilitates the attachment of a biotin or biotin based functional group to the therapeutic monomer in association with the ROP to form the polymer.

In the embodiment shown, synthesis route 100 is divided into a two-part process, wherein biotinol 108 is generated in accordance with synthesis route 100A, and thereafter in accordance with synthesis route 100B, the biotinol 108 is attached to the polyguanidinium in association with the ROP of the cyclic guanidinium monomer 110. With reference to synthesis route 100A, a biotin monomer 102 can be reacted with oxalyl chloride 104 at room temperature (r.t.) to modify the biotin monomer 102 into compound 106. Compound 106 can further be reduced at r.t. to form biotinol 108, which is a modified alcohol form of the biotin monomer comprising a hydroxyl group side chain. In accordance with synthesis route 100B, this biotinol 108 can be used as an initiator of a ROP of the cyclic guanidinium monomer 110 in association with reagents/catalysts including 1,8-Diazabicyclo[5.4.0]undec-7-ene/thiourea (DBU/TU) and methylene chloride ($CH_2CL_2$) to form protected biotinylated polyguanidinium 114. The protected biotinylated polyguanidinium 114 can then be deprotected using reagents/catalysts trifluoroacetic acid (TFA) and dichloromethane (DCM) in r.t. overnight to form the biotinylated polyguanidinium 116 (BG) having Formula 2.

Although synthesis route 100B is demonstrated using a single, cyclic guanidinium monomer 110 having an alkyl spacer group, synthesis route 100B can be extended to other biotinylated polyguanidiniums. For example, synthesis route 100B can be used to attach biotin to various biotinylated polyguanidinium monomer and copolymer variations (e.g., with different spacer groups for $R_2$, biotinylated polyguanidinium having Formula 3, and the like) using biotinol 108 as the initiator for the ROP of the cyclic guanidinium monomer.

Furthermore, the disclosed techniques for enhancing update of therapeutic polymers via the attachment of a biotin or biotin based functional group thereto can be applied to anticancer and antimicrobial peptides. In this regard, the disclosed biotinylated therapeutic polymers are not limited to polyguanidinium polymers. For example, in some embodiments an anticancer and antimicrobial quaternary ammonium functional block copolymer can be biotinylated (e.g., in accordance with synthesis route 100 or synthesis route 200 described below) to further enhance the update of these polymers into tumor cells.

Figure 2:
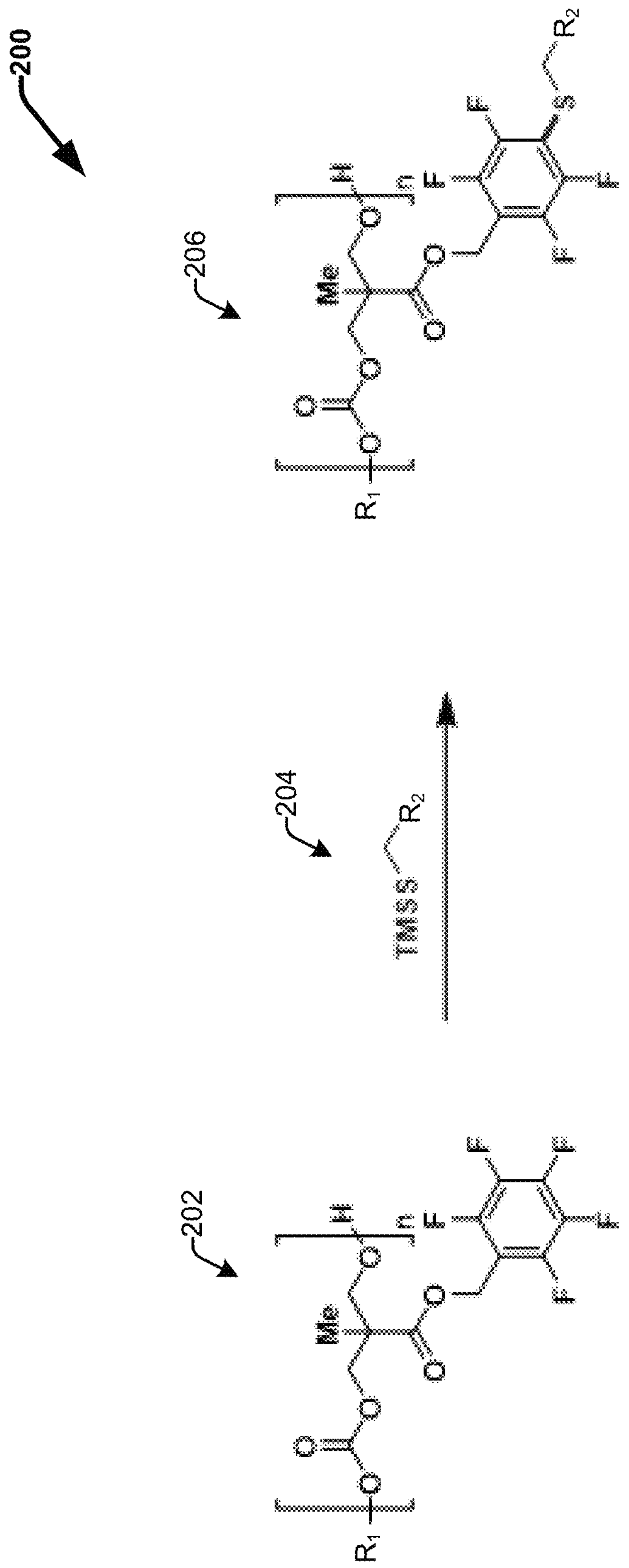
FIG. 2 presents another example synthesis route 200 for generating a biotinylated therapeutic polymer in accordance with various embodiments described herein

FIG. 2 presents another example synthesis route 200 for generating a biotinylated therapeutic polymer in accordance with various embodiments described herein. Synthesis route 200 facilitates the attachment of biotin to a therapeutic polymer via post-polymerization modification. In this regard, in some embodiments, functionality can be introduced to the disclosed therapeutic macromolecules via post polymerization modification. The functionality can include a biotin based functional group, a guanidinium based functional group, a sugar based functional group, and the like. Post polymerization modification provides an efficient and straightforward manufacturing process that can be used to synthesize functionalized therapeutics macromolecules with significant diversity. For example, synthesis route 200 can be used to form a therapeutic polymer having chemical formula 4 below, wherein $R_1$ can comprise a variety of functional groups that can be used as the initiator of the ROP of the polymer, and $R_2$ comprises biotin or a biotin based functional group. For example, in some embodiment, $R_1$ can comprise a benzyl alcohol, a disaccharide (a sugar), a dansyl amid (a reactive fluorescent dye), or another suitable hydroxyl ROP initiator.

Formula 4

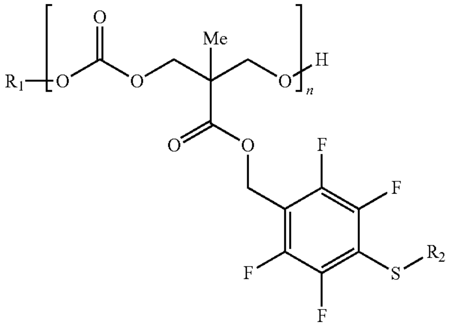

In accordance with synthesis route 200, the therapeutic polymer 202 comprises a perfluoro amine functional group as opposed to guanidinium. In various embodiment, the perfluoro amine can be cationic and provide same or similar cell translocation functionalities (e.g., via ion exchange) as the guanidinium moiety. In this regard, in some embodiments of synthesis route 200, a guanidinium moiety can be used instead of the perfluoro amine. In order to attach the biotin functional group $R_2$ to the therapeutic polymer 202, a thiol such as tetramethylsilane (TMSS) can be installed onto the biotin $R_2$ to generate the modified biotin 204. The modified biotin 204 can then be used to perform a nucleophilic aromatic substitution on the cationic moiety (e.g., the perfluoro amine or in some cases a guanidinium moiety or the like) to generate the biotinylated therapeutic polymer 206 having chemical formula 4.

In accordance with Formula 1, Formula 2, Formula 3 and Formula 4, the polymer backbone comprises polycarbonate. However, in one or more additional embodiments, other hydrophobic polymers can be employed as the polymer backbone. For example, in other embodiments, the polymer backbone can comprise polylysine, polyionene, polyethylenimine and the like. In some implementations, no restriction is placed on the polymer skeletal structure of the skeletal backbone. Exemplary non-limiting polymer skeletal structures can include linear polymers, branched polymers, star polymers, mykto-arm star polymers, latter polymers, cyclic polymers, and graft polymers. The forgoing polymer types can comprise a homopolymer, a random copolymer, or a block copolymer chain. In various exemplary embodiments, the biotinylated polyguanidinium is a linear polymer comprising a plurality of covalently bonded guanidinium functionalized monomer units. Herein, a linear polymer has one branch having two peripheral ends (i.e., dangling ends, as the two ends of a segment of a rope). The one branch can comprise one or more polymer chain segments covalently linked together at respective polymer chain ends by way of any suitable linking group, which can include a single bond. Each polymer chain segment of a linear polymer can comprise a homopolymer, random copolymer, or block copolymer chain comprising one or more repeat units. At least one of the polymer chain segments comprises one or more repeat units of a monomer comprising a cationic functional group, such as guanidinium functionalized monomer, perfluoro amine monomer, or the like.

The various biotinylated therapeutic polymers having chemical formulas 1-4 discussed above have demonstrated strong, broad-spectrum, antimicrobial selectivity and efficacy toward a variety of gram-negative and gram-positive bacteria types, including *P. aeruginosa*. The antimicrobial efficacy and/or specificity (or the degree of selectivity toward microbial cells as opposed to mammalian cells) of the biotinylated form of these polymers relative to the same polymers without biotin was further increased. The biotinylated therapeutic polymers having chemical formulas 1-4 have also demonstrated strong, broad-spectrum selectivity and efficacy against many different cancer cell lines. Similarly, the antimicrobial efficacy and the degree of selectivity toward cancer cells as opposed to mammalian cells of the biotinylated form of these polymers relative to the same polymers without biotin was further increased.

Figure 3:
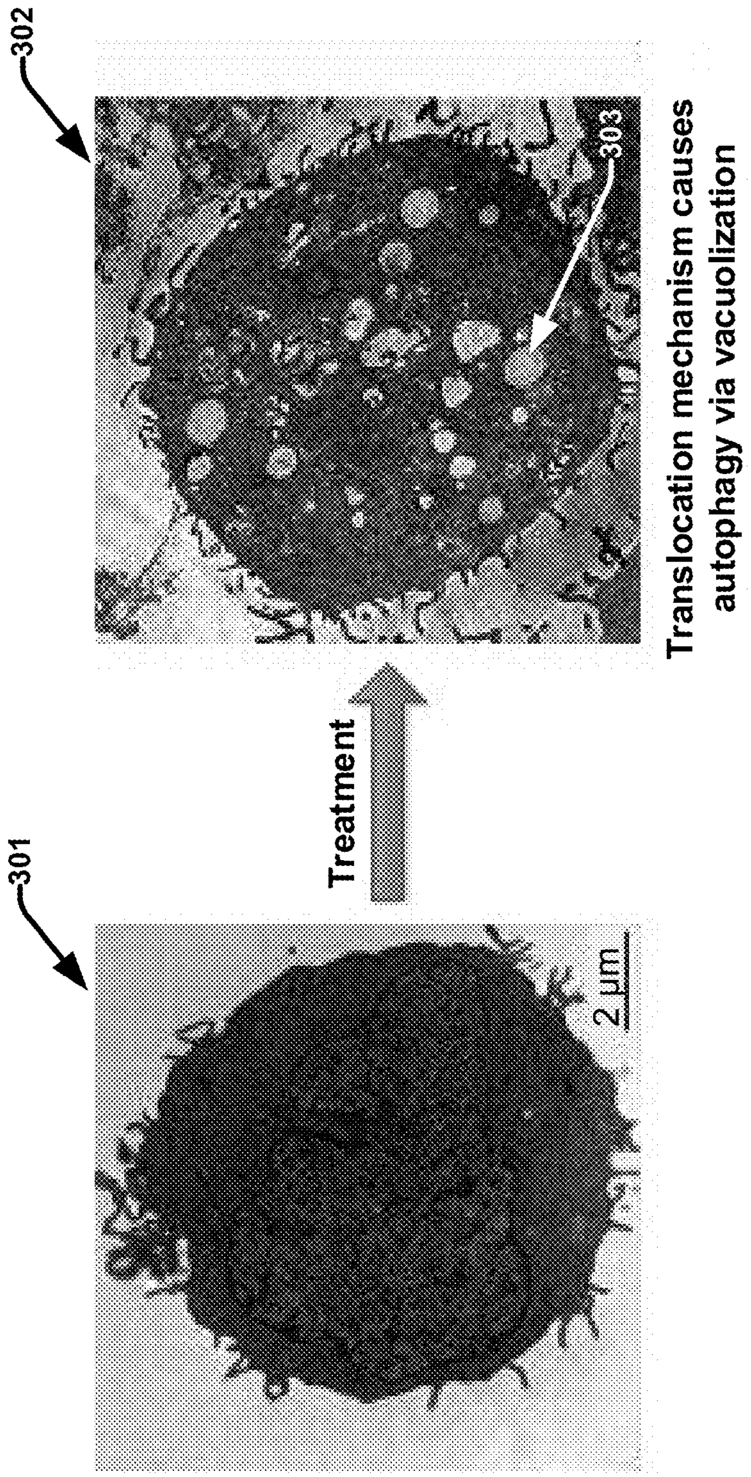
FIG. 3 presents transmission electron microscopy (TEM) micrograph images of a cancer cell before and after treatment with a biotinylated polyguanidinium based anticancer agent in accordance with various embodiments described herein.

For example, FIG. 3 presents transmission electron microscopy (TEM) micrograph images of a cancer cell before and after treatment with a biotinylated polyguanidinium based anticancer agent in accordance with various embodiments described herein. In accordance with this example, the anticancer agent used comprised a block copolymer formed with guanidinium monomers (e.g., having chemical Formula 3 or the like). When used as an anticancer agent, these polymers self-assemble into micelles. Upon interaction with cancer cells, these polymers translocate though the cancer cell membrane as facilitated by the micelle structure, the guanidinium moiety and the biotin group, and accumulate within the cancer cell. Once inside, the accumulated polymers kill the cancer cell quite dramatically. For example, as shown in FIG. 3, the left TEM image (image 301) depicts a cancer cell prior to treatment with the polyguanidinium block copolymer, and the TEM image on the right (image 302), depicts the same cancer cell post treatment. As shown in image 302, the polymers translocate into the cancer cell and cause autophagy via vacuolization. For example, the polymer causes the cancer cell to form holes or vacuoles 303 as a result of the cell essentially destructing itself from the inside out.

Figure 4A:
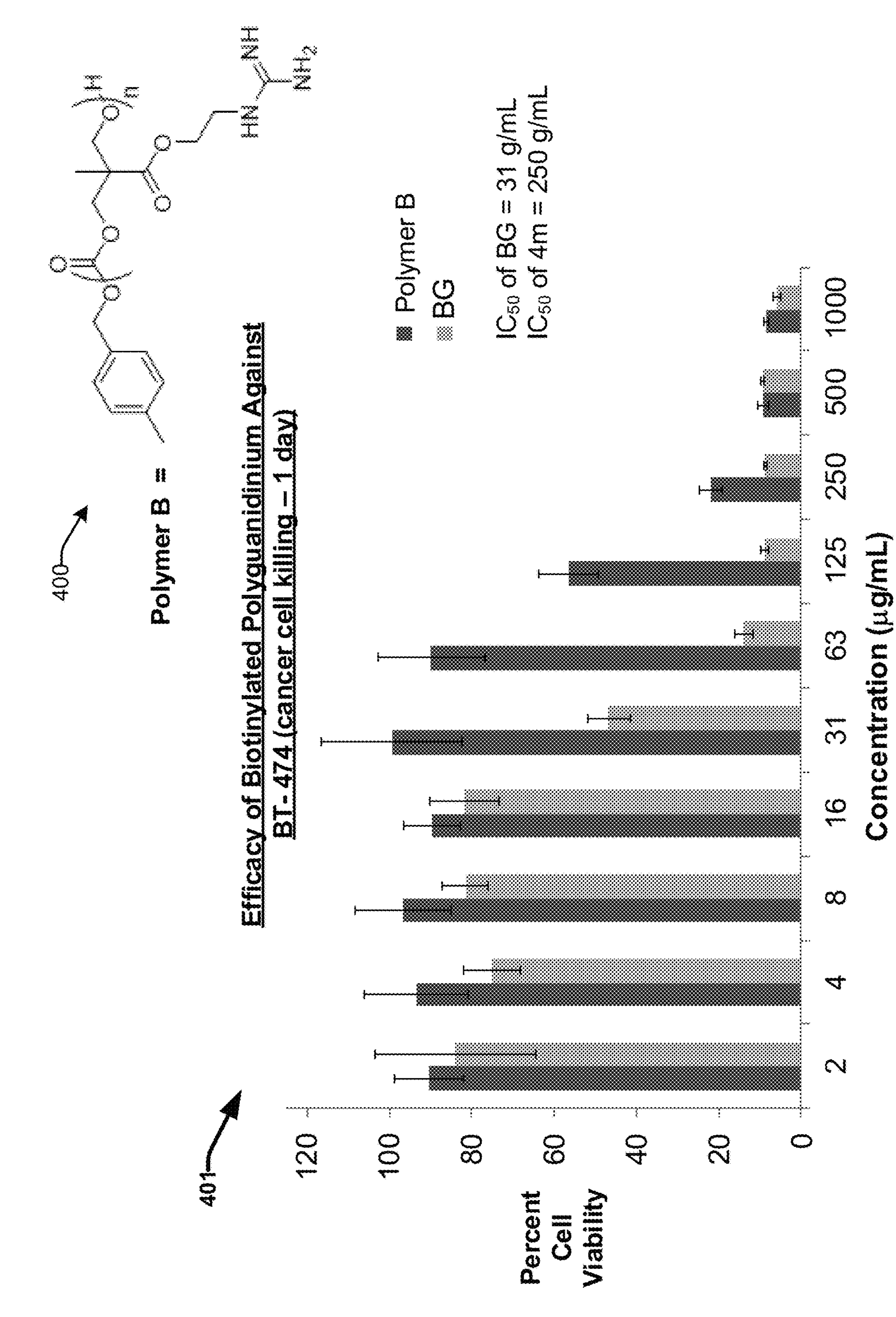
FIGS. 4A and 4B present charts illustrating the in vitro efficacy of a biotinylated polymer and a non-biotinylated polymer against cancer cell line BT-474 (a human ductal carcinoma cell line) in accordance with various embodiments described herein.
Figure 4B:
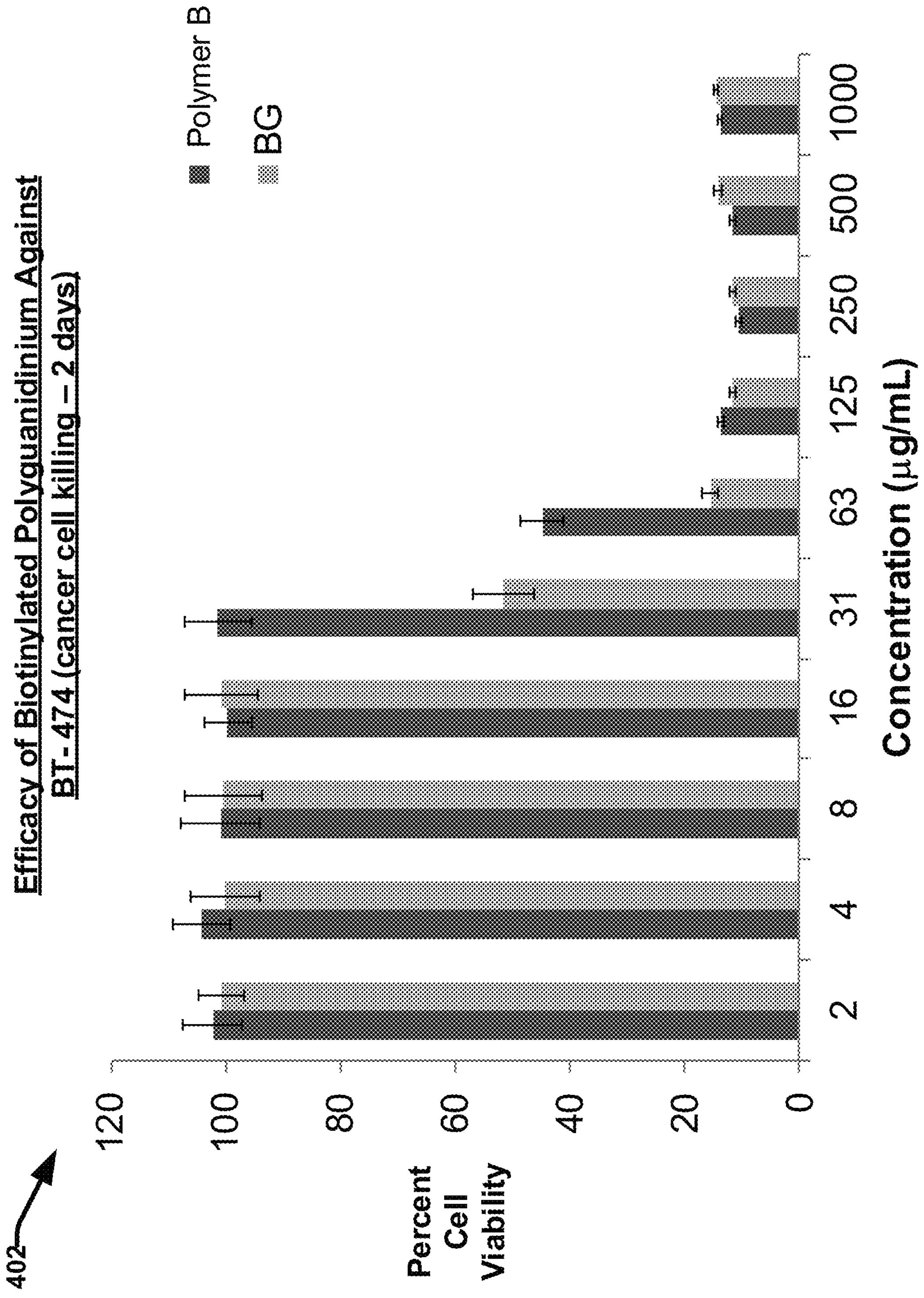

FIGS. 4A and 4B present charts illustrating the in vitro efficacy of a biotinylated polymer and a non-biotinylated polymer against cancer cell line BT-474 (a human ductal carcinoma cell line) in accordance with various embodiments described herein. The biotinylated polymer tested comprised a biotinylated polyguanidinium having chemical Formula 2 (BG). The non-biotinylated polymer tested for comparison comprised a polyguanidinium referred to herein in as Polymer B or 4m4-$[C2Gua]_{17}$. The chemical structure for Polymer B is shown in the upper righthand corner of FIG. 4A with reference to arrow 400. In accordance with FIGS. 4A and 4B, the anticancer efficacy of the respective polymers was tested as a function of cell viability using a 3-(4,5-dimethylthiazol-2-yl)-2,5-diphenyltetrazolium bromide (MTT) assay at different concentrations over a 2 day (48 hour) period. FIG. 4A presents a Chart 401 demonstrating the results after 1 day (24 hours) and FIG. 4B presents a Chart 402 demonstrating the results after 2 days (48 hours). As shown in Charts 4A and 4B, the BG (biotinylated polyguanidinium) has significantly stronger anticancer activity relative to the non-biotinylated polyguanidinium as evidenced by the lower amount of anticancer agent required to inhibit survival (or kill) of 50% of the cancer cell population, referred to as the IC50 value. In this regard, after 1 day, the IC50 value for BG 31 μg/ml is half that of m4 which is 250 μg/ml.

Figure 5:
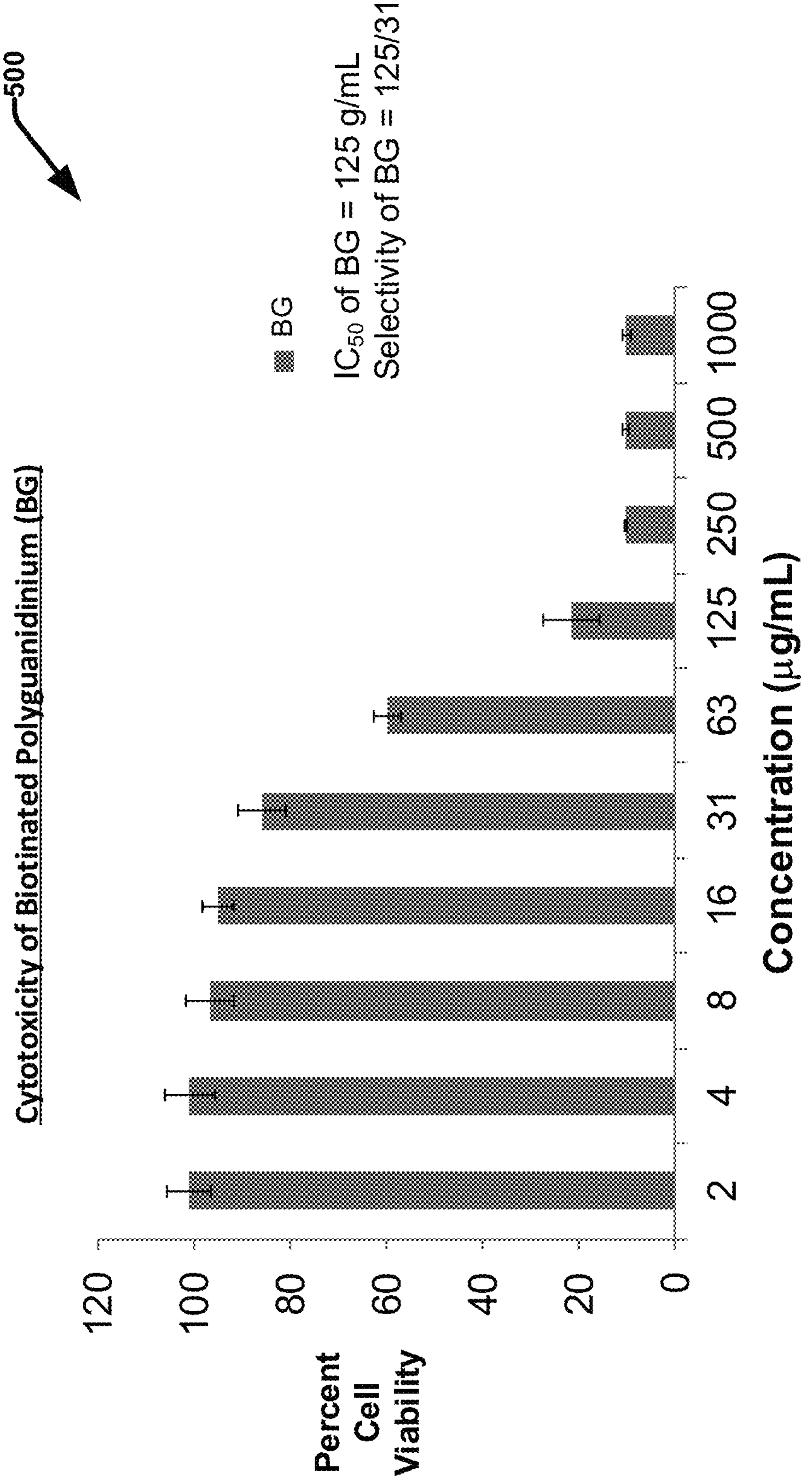
FIG. 5 presents a chart illustrating the cytotoxicity of a biotinylated polymer against healthy non-cancerous mammalian cell line HEK293 in accordance with various embodiments described herein.

FIG. 5 presents a Chart 500 illustrating the cytotoxicity of a biotinylated polymer against healthy non-cancerous mammalian cell line HEK293 in accordance with various embodiments described herein. The biotinylated polymer tested comprised a biotinylated polyguanidinium having chemical Formula 2 (BG). In accordance with Chart 500, the cytotoxicity of BG against HEK293 was tested as a function of cell viability using an MTT assay. As shown in Chart 500, almost 100% of the HEK293 cells survived at concentrations of BG up to about 31 μg/ml. BG further showed a high IC50 value at about 125 μg/ml, rending the selectivity of BG toward HEK293 125/31 or 4 μg/ml. This demonstrates that the disclosed biotinated polyguanidiniums not only demonstrate high efficacy as an anticancer agent, but also demonstrate strong selectivity toward diseased cells over healthy mammalian cells.

Figure 6:
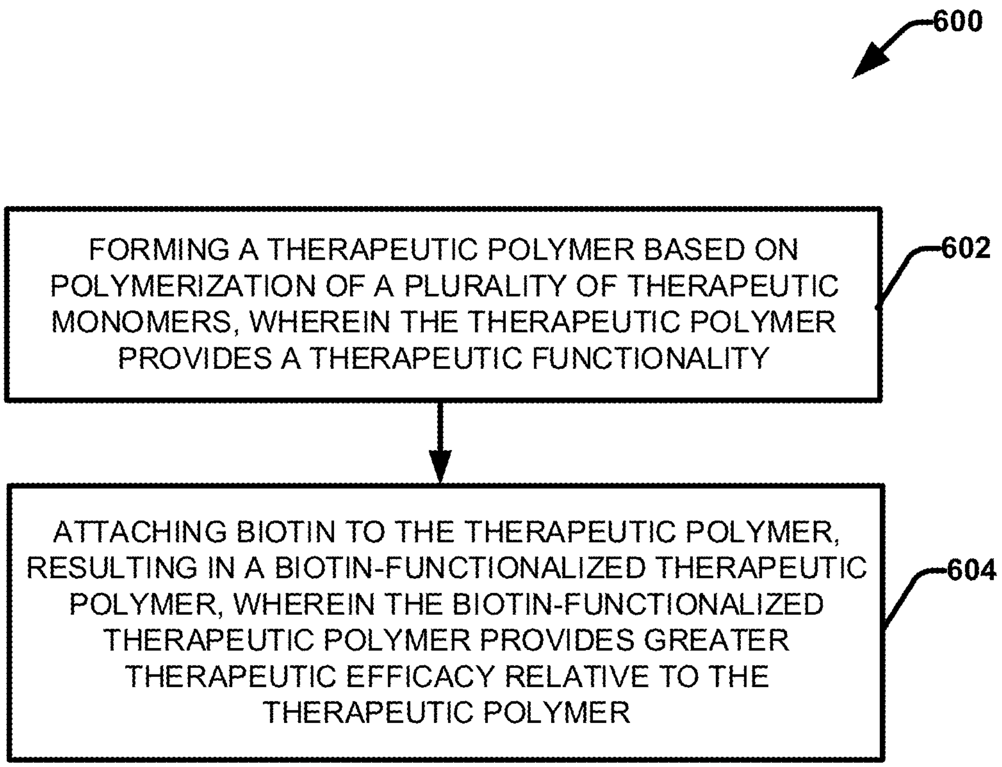
FIG. 6 presents a high-level flow diagram of an example method for enhancing the selectivity and efficacy of therapeutic polymers against a broad spectrum of pathogens and cancer cell lines via the introduction of biotin in accordance with various embodiments described herein.

FIG. 6 presents a high-level flow diagram of an example method 600 for enhancing the selectivity and efficacy of therapeutic polymers against a broad spectrum of pathogens and cancer cell lines via the introduction of biotin in accordance with various embodiments described herein. Repetitive description of like elements employed in respective embodiments is omitted for sake of brevity.

At 602, a therapeutic polymer can be formed based on polymerization of a plurality of therapeutic monomers (e.g., cyclic carbonate guanidinium functionalized monomers), wherein the therapeutic polymer provides a therapeutic functionality (e.g., an antimicrobial and/or anticancer functionality). At 604, biotin can be attached to the therapeutic polymer, resulting in a biotin-functionalized therapeutic polymer (e.g., BG), wherein the biotin-functionalized therapeutic polymer provides greater therapeutic efficacy relative to the therapeutic polymer. For example, in some embodiments, the biotin can be attached via synthesis route 100. In other embodiments, the biotin can be attached via synthesis route 200.

II—Therapeutic Coacervates

In various additional embodiments, to improve selectivity, bioavailability and reduce serum complexation, an anionic carrier and be used to deliver the antimicrobial and/or anticancer polymers in the form a coacervate. Coacervation is a phenomenon in which cationic and anionic water-soluble polymers interact in fluid (e.g., water, serum, etc.) to form a liquid, polymer-rich phase complex held together by electrostatic forces. The term "coacervate" is used herein to refer to the complex formed between two polymers as a result of coacervation. In accordance with the disclosed techniques, a coacervate can be formed between a cationic antimicrobial polymer and an anionic carrier polymer. The coacervate complex shields the cationic therapeutic polymer in a loose particle structure based on the dynamic electrostatic interaction between the cationic polymer and the anionic polymer, thereby reducing toxicity of the cationic therapeutic polymer mammalian cells.

In this regard, the coacervate complexes disclosed herein are relatively loose particle structures held together by electrostatic forces. The coacervate complexes are further neutral in charge as a result of charge cancelation between the anionic and cationic polymer. As a result, the anionic polymer and the cationic therapeutic polymer remain in a dynamic equilibrium when suspended in solution. However, when the coacervate complex interacts with the negatively charged surface the cellular membrane of a bacteria cell or cancer cell, the coacervate complex opens up to expose the cationic therapeutic polymer because the cationic therapeutic polymer is more attracted to the bacteria or cancer cell membrane relative to the anionic carrier polymer. As a result, the cationic therapeutic polymer is released from the coacervate complex and an ion exchange occurs between the cationic therapeutic polymer and the anionic surface of the bacteria or cancer cell. This ion exchange neutralizes the cationic polymer and facilitates translocation of the cationic polymer through the bacteria or cancer cell membrane. Once internalized, the cationic polymer induces necrosis by the bacterial cell or autophagy by the cancer cell, respectively.

Figure 7:
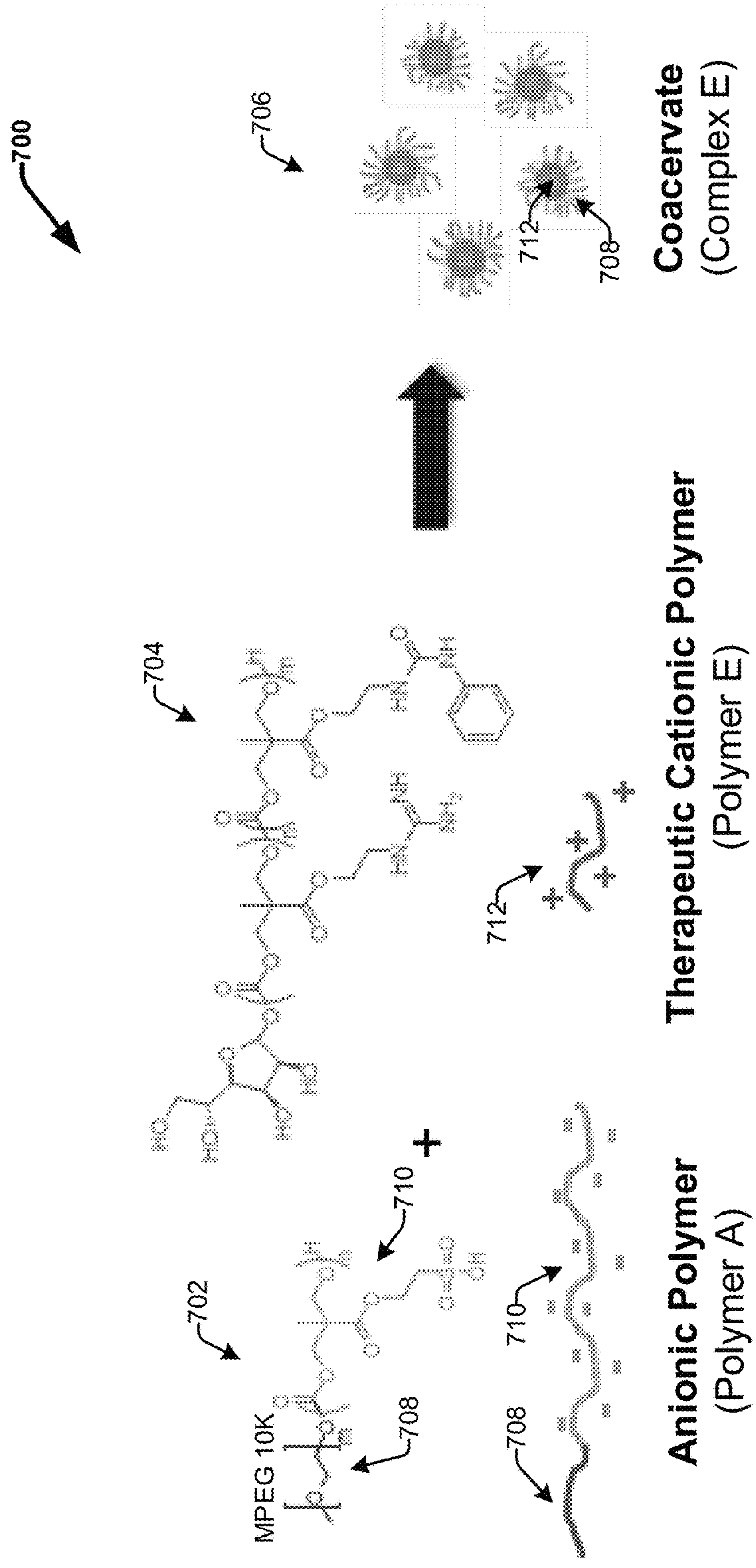
FIG. 7 presents an example synthesis route 600 for forming a therapeutic coacervate in accordance with various embodiments described herein.

FIG. 7 presents an example synthesis route 700 for forming a therapeutic coacervate in accordance with various embodiments described herein. In accordance with synthesis route 700, an anionic polymer 702 can be combined with a therapeutic cationic polymer 704 in solution (e.g., water, DI water, serum, bodily fluids, etc.) to form coacervate complex 706. In the embodiment shown, the anionic polymer 702 comprises a sulfonate functional polycarbonate having chemical Formula 5 below and referred to herein as Polymer A. The therapeutic cationic polymer 704 comprises a functional guanidinium cationic copolymer having chemical Formula 6 below and referred to herein as Polymer E.

Formula 5 - (Polymer A)

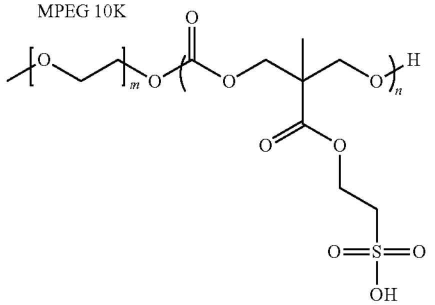

Formula 6 - (Polymer E)

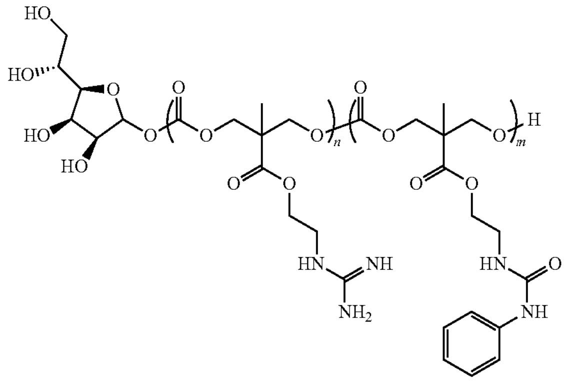

The coacervate complex 706 formed between anionic Polymer A and cationic Polymer E is referred to herein as Complex E. As shown in FIG. 7, the anionic polymer 702 can comprise an anionic polymer backbone 710 and a relative neutral polyethylene glycol (PEG) tail 708 extending therefrom. In the embodiment shown, the PEG is more specifically methoxy polyethylene glycol (MPEG). In various embodiments, the PEG tail 708 can comprise MPEG or PEG. Based in part on this chemical structure of the anionic polymer 702, the combined anionic polymer and cationic polymer self-assemble into coacervate complex 706 having a relatively circular/spherical particle structure. The structure of the coacervate complex 706 shields the cationic portion 712 of the cationic polymer within an internal region of the particle, surrounded and protected by the neutral, PEG tail 708 portion of the anionic polymer 702.

Figure 8:
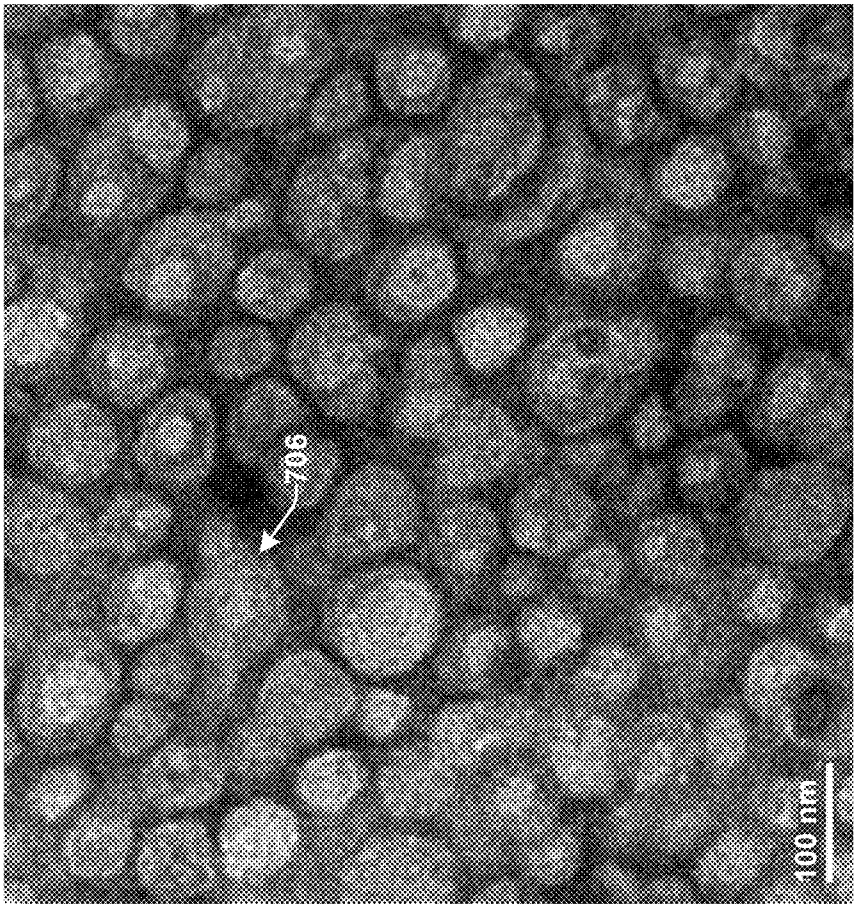
FIG. 8 provides a transmission electron microscopy (TEM) image of Complex E in accordance with various embodiments described herein. In the embodiment shown.

For example, FIG. 8 provides a transmission electron microscopy (TEM) image of Complex E in accordance with various embodiments described herein. As shown in FIG. 8, the coacervate complexes 706 have a relatively circular or spherical structure around 100 nm in diameter.

With reference again to FIG. 7, the PEG tail 708 facilitates shielding the cationic portion 712 of the therapeutic cationic polymer 704 within the formed coacervate complex. The PEG tail 708 also facilitates circulation of the coacervate complex 706 in solution (e.g., within the body) and minimizing the toxicity of the coacervate complex 706 toward mammalian cells. In this regard, PEG is water soluble and the human body doesn't really recognize PEG. When the anionic polymer 702 and the therapeutic cationic polymer 704 assemble into the coacervate nanoparticles, the PEG presents itself on the outside. As a result, macrophages and biomolecules that normally sequester particles recognize the coacervate complex 706 only as water. Thus, immune cells don't sequester the coacervate complex or try kill it.

The number "m" of PEG units and the number "n" of polymer units that make up the polymer backbone of Polymer A can vary. In the embodiment shown, the PEG tail 708 is identified as MPEG 10K, which denotes a mixture of PEG molecules (about 195-265 PEG molecules) having an average MW of 10,000 g/mol. In this regard, the value of m can be between about 195 and 265. However, in other embodiments, m can be between 40 and 500. In various embodiment, the value of "n" for Polymer A can be between 10 and 100, more preferably between 20 and 80, and even more preferably between 30 and 50. In various embodiments, the value of "n" for Polymer A is 40. The value of "n" and "m" with respect to Polymer E can also vary. For example, in some embodiments, the value of n for Polymer E can be less than 50 and more preferably less than 41, and in one embodiment, the value of n in for Polymer E is 11. The value of m for Polymer E can be less than 10 and more preferably less than 5. In various embodiments, the value of m for Polymer E can be 2.

Complex E provides one example coacervate complex that provides both antimicrobial and anticancer functionality with higher efficacy and/or selectivity relative to the cationic Polymer E alone. Various additional antimicrobial and anticancer coacervates can be formed in accordance with synthesis route 700 using other anionic polymers in combination with Polymer E, as well as other therapeutic cationic polymers. For example, some additional anionic polymers that can be used instead of Polymer A to form a therapeutic coacervate complex in combination with Polymer E or another therapeutic cationic polymer can include acid-functionalized polycarbonates such a carboxylic acid-functionalized polymer, a phosphoric acid-functionalized polymer, or the like. In this regard, one example acid-functionalized polymer that can be used as the anionic polymer instead of Polymer A can include a diblock carboxylic acid functionalized copolymer having chemical Formula 7 below and referred to herein as Polymer J:

Formula 7 (Polymer J)

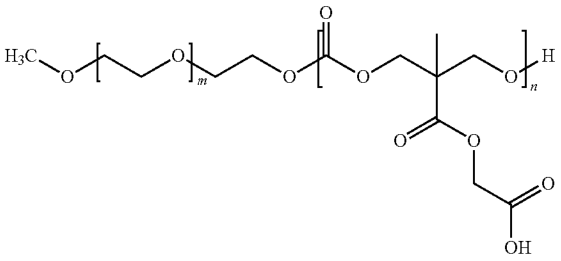

In accordance with Formula 7, the number "m" of PEG units and the number "n" of polymer units that make up the polymer backbone of Polymer J can vary. In this regard, the value of m can be between about 195 and 265. However, in other embodiments, m can be between 40 and 500. In one exemplary embodiment, m can be 113. In various embodiment, the value of "n" for Polymer J can be between 10 and 100, more preferably between 20 and 80, and even more preferably between 30 and 50. In various embodiments, the value of "n" for Polymer J is 40.

Furthermore, in some embodiments, biotin ligands can be installed on one or more chain ends of the anionic polymer 702 and/or the therapeutic cationic polymer 704 to enhance the targeting selectivity of the resulting coacervate complex. For example, in some embodiments, Polymer E can be replaced with the polymer having chemical Formula 2 (also referred to herein as Polymer BG). In other embodiments, the anionic (e.g., Polymer A, Polymer J, and the like) can be biotinylated via the attachment of a biotin group to one or more ends of the polymer backbone and/or a side chain extending from the polymer backbone. In accordance with these embodiments, the biotinylated form of Polymer A is referred to herein as Polymer A' and has chemical Formula 8 below, and the biotinylated form of Polymer J is referred to herein as Polymer J' and has chemical Formula 9 below.

Formula 8

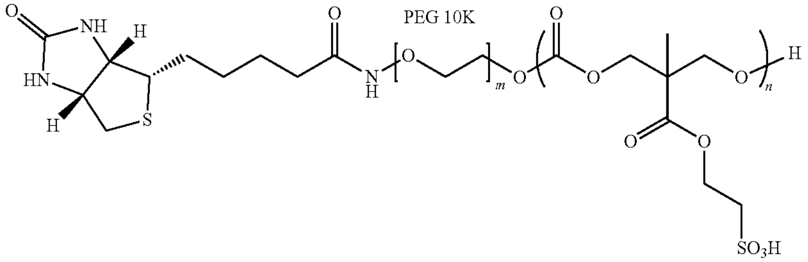

(Polymer A')

-continued

Formula 9

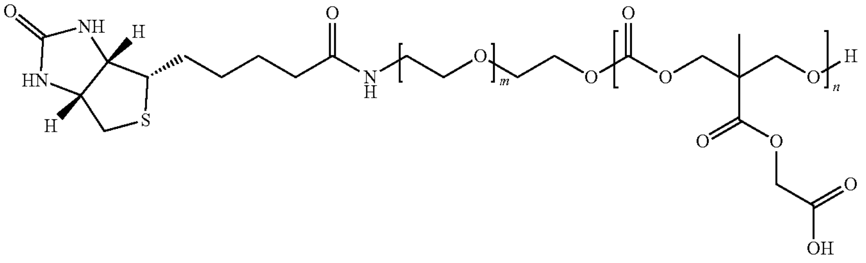

(Polymer J')

As shown with reference to Formulas 5 and 8, Polymer A' can comprise a same or similar structure as Polymer A with the addition of a biotinol functional group to an end of the polymer backbone. In this regard, in some embodiments, "m" and "n" can be the same values in Formula 8 as those used for Formula 5. In some embodiments however, the values for "m" and "n" for Polymer A' can be different than those used for Polymer A. Similarly, Polymer J' can comprise a same or similar structure as Polymer J with the addition of a biotinol functional group to an end of the polymer backbone. In this regard, in some embodiments, "m" and "n" can be the same values in Formula 9 as those used for Formula 7. In some embodiments however, the values for "m" and "n" for Polymer J' can be different than those used for Polymer J.

Other therapeutic (e.g., anticancer and/or antimicrobial) cationic polymers that can be used instead of Polymer E can include but are not limited to Polymer B, Polymer C, Polymer F, Polymer D, Polymer G and Polymer H, respectively having chemical Formulas 10, 11, 12, 13, 14 and 15 as follows:

Formula 10 - (Polymer B)

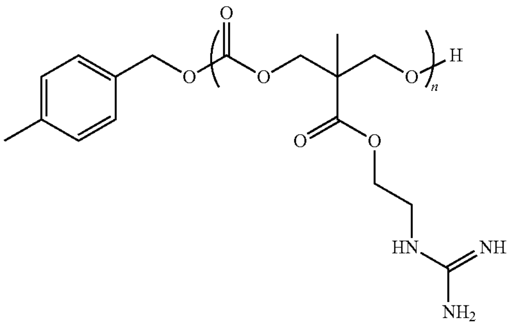

Formula 11 - (Polymer C)

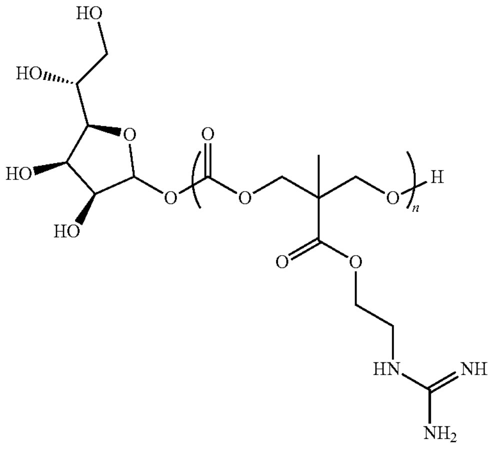

Formula 12 - (Polymer F)

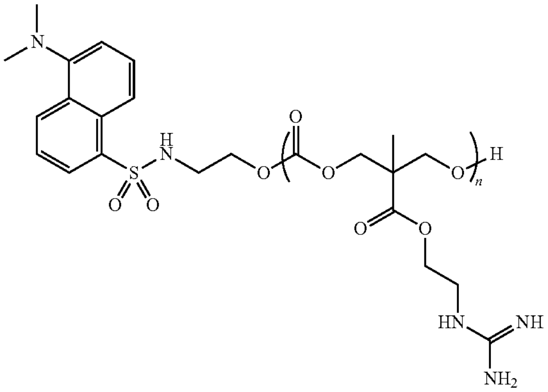

Formula 13 - (Polymer D)

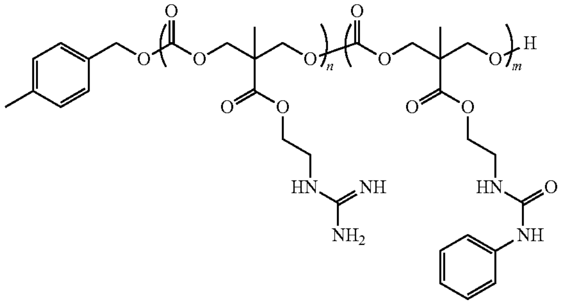

-continued

Formula 14 - (Polymer G)

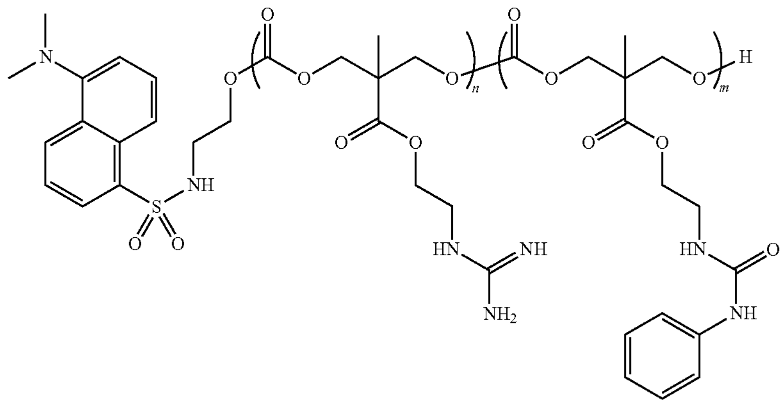

Formula 15 - (Polymer H)

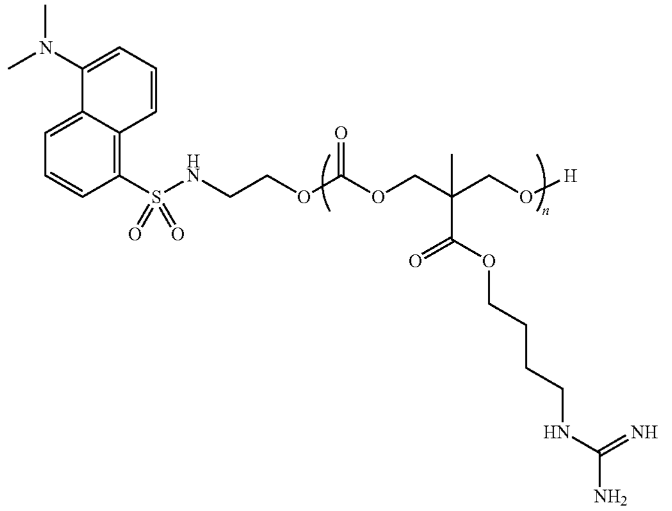

The values of "n" and "m" with respect to the cationic polymers having Formulas 10-15 can vary. In one or more embodiments, with respect to Formula 10 (Polymer B), n can be less than 60 and more preferably less than 45. In one embodiment, the value of n in Formula 10 can be 16. Similarly, with respect to Formula 11 (Polymer C), n can be less than 60 and more preferably less than 45, and in one embodiment, the value of n in Formula 11 can be 16. With respect to Formulas 12 and 15 (Polymer F and Polymer H, respectively) can be less than 60 and more preferably less than 45, and in one embodiment, the value of n in Formula 12 can 19 and the value of n in Formula 15 can be 20. With respect to Formula 13 (Polymer D) and Formula 14 (Polymer G), n can be less than 60 and more preferably less than 45, and in one embodiment, the value of n in Formulas 13 and 14 can be 16. The value of m in Formulas 13 and 14 can be less than 10 and more preferably less than 5. In various embodiments, the value of m in Formulas 13 and 14 can be 2.

In this regard, in addition to Complex E, in various embodiments, antimicrobial and/or anticancer coacervate complexes can be formed using a combination of an anionic polymer such as Polymer A, Polymer A', Polymer J, Polymer J' or the like, with a cationic polymer, wherein the cationic polymer can include but is not limited to, one of: Polymer B, Polymer C, Polymer D, Polymer E, Polymer F, Polymer G, Polymer H and Polymer BG (wherein Polymer BG has chemical Formula 2 supra). The resulting coacervate complexes are respectively referred to herein as identified in Table 1.

TABLE 1

| Anionic Polymer | Cationic Polymer | Coacervate |
|---|---|---|
| Polymer A | Polymer B | Complex B |
| Polymer A' | Polymer B | Complex B' |
| Polymer A | Polymer C | Complex C |
| Polymer A' | Polymer C | Complex C' |
| Polymer A | Polymer D | Complex D |
| Polymer A' | Polymer D | Complex D' |
| Polymer A | Polymer E | Complex E |
| Polymer A' | Polymer E | Complex E' |
| Polymer A | Polymer F | Complex F |
| Polymer A' | Polymer F | Complex F' |
| Polymer A | Polymer G | Complex G |
| Polymer A' | Polymer G | Complex G' |
| Polymer A | Polymer H | Complex H |
| Polymer A' | Polymer H | Complex H' |
| Polymer A | Polymer BG | Complex BG |
| Polymer A' | Polymer BG | Complex BG' |
| Polymer J | Polymer B | Complex BJ |
| Polymer J' | Polymer B | Complex BJ' |
| Polymer J | Polymer C | Complex CJ |
| Polymer J' | Polymer C | Complex CJ' |
| Polymer J | Polymer D | Complex DJ |
| Polymer J' | Polymer D | Complex DJ' |
| Polymer J | Polymer E | Complex EJ |
| Polymer J' | Polymer E | Complex EJ' |

TABLE 1-continued

| Anionic Polymer | Cationic Polymer | Coacervate |
|---|---|---|
| Polymer J | Polymer F | Complex FJ |
| Polymer J' | Polymer F | Complex FJ' |
| Polymer J | Polymer G | Complex GJ |
| Polymer J' | Polymer G | Complex GJ' |
| Polymer J | Polymer H | Complex HJ |
| Polymer J' | Polymer H | Complex HJ' |
| Polymer J | Polymer BG | Complex BGJ |
| Polymer J' | Polymer BG | Complex BGJ' |

Figure 9A:
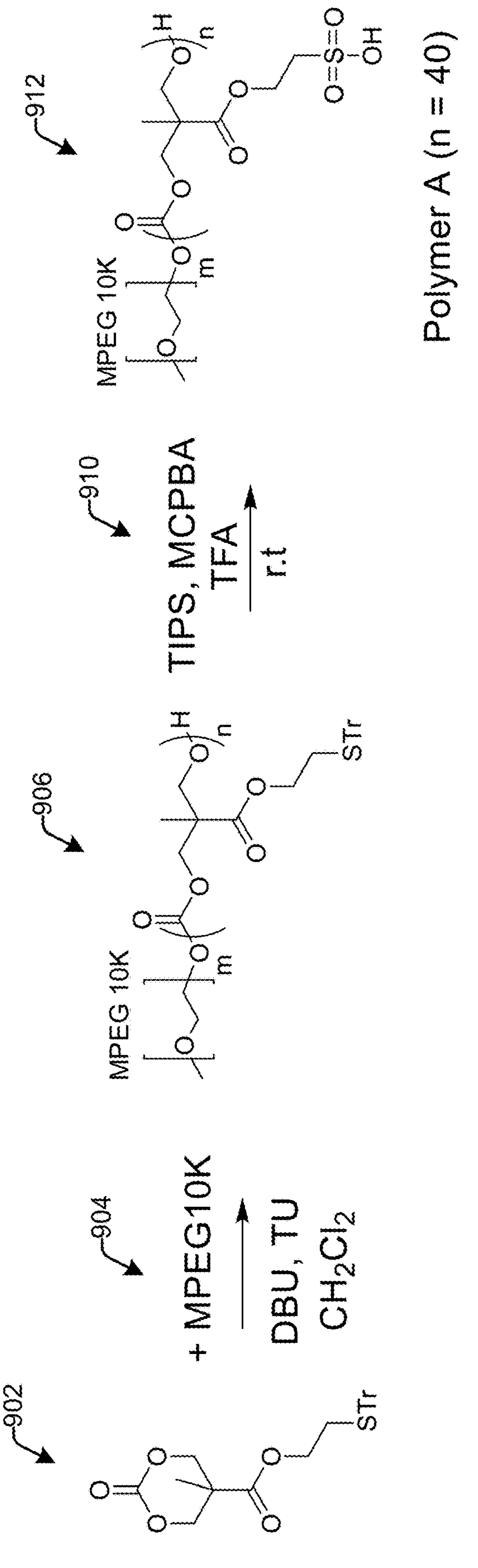
FIG. 9A presents an example synthesis route for forming Polymer A in accordance with various embodiments described herein. In the embodiment shown.

FIG. 9A presents an example synthesis route 900 for forming Polymer A in accordance with various embodiments described herein. In the embodiment shown, a tritol (Tr) protected thiol monomer 902 can be reacted with reactants 904 including MPEG 10K, DBU/TU and $CH_2CL_2$ to form the block copolymer 906. In this regard, using MPEG as an initiator, a ROP of the cyclic carbonate of protected thiol monomer 902 can be performed to generate the block copolymer 906 including the protected thiol with the Tr group. Tr represents three phenyl groups. These phenyl groups can be deprotected resulting in an unprotected sulfurhydrogen (SH) thiol. In this regard, the block copolymer 906 can further be reacted with reactants 910, including triisopropylsilane (TIPS), meta-chloroperoxybenzoic acid (MCPBA) and TFA at r.t., to deprotect the Tr group and cause an oxidation of the thiol to generate the sulfonate polymer 912, referred to herein as Polymer A.

Figure 9B:
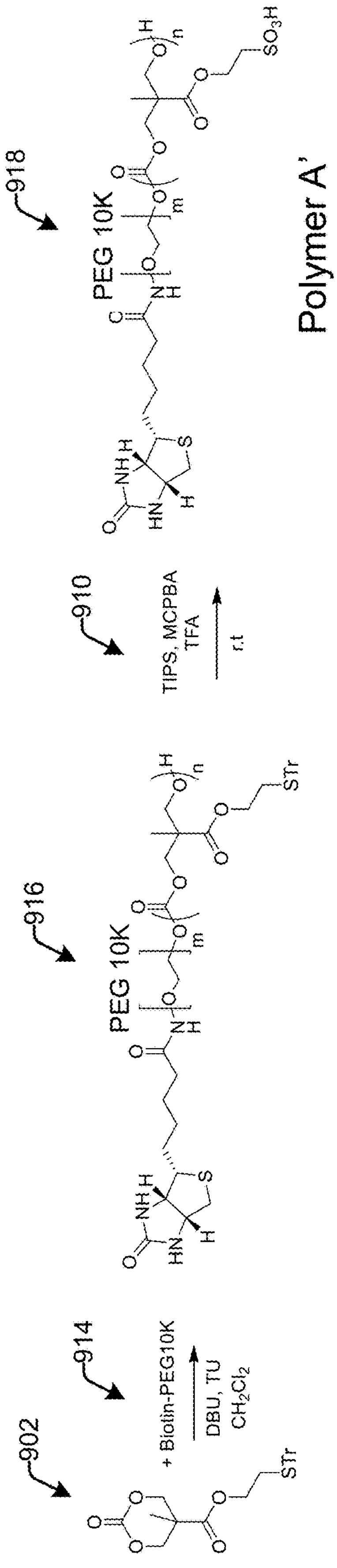
FIG. 9B presents an example synthesis route for forming Polymer A' in accordance with various embodiments described herein.

FIG. 9B presents an example synthesis route 901 for forming Polymer A' in accordance with various embodiments described herein. Synthesis route 901 is similar to synthesis route 900 with the addition of a biotin functional group to the PEG 10K used for the ROP of the protected thiol monomer 902. Repetitive description of like elements employed in respective embodiments is omitted for sake of brevity. In accordance with synthesis route 901, the Tr, protected thiol monomer 902 can be reacted with reactants 914 including biotinylated PEG, DBU/TU and $CH_2CL_2$ to form the block copolymer 916. In this regard, using biotinylated PEG as an initiator, a ROP of the cyclic carbonate of protected thiol monomer 902 can be performed to generate block copolymer 916 including the Tr group and the biotinol functional group bound to an end of the block copolymer 916. The block copolymer 916 can further be reacted with reactants 910, including TIPS, MCPBA and TFA at r.t., to deprotect the Tr group and cause an oxidation of the thiol to generate the biotinylated sulfonate polymer 918, referred to herein as Polymer A'.

Figure 9C:
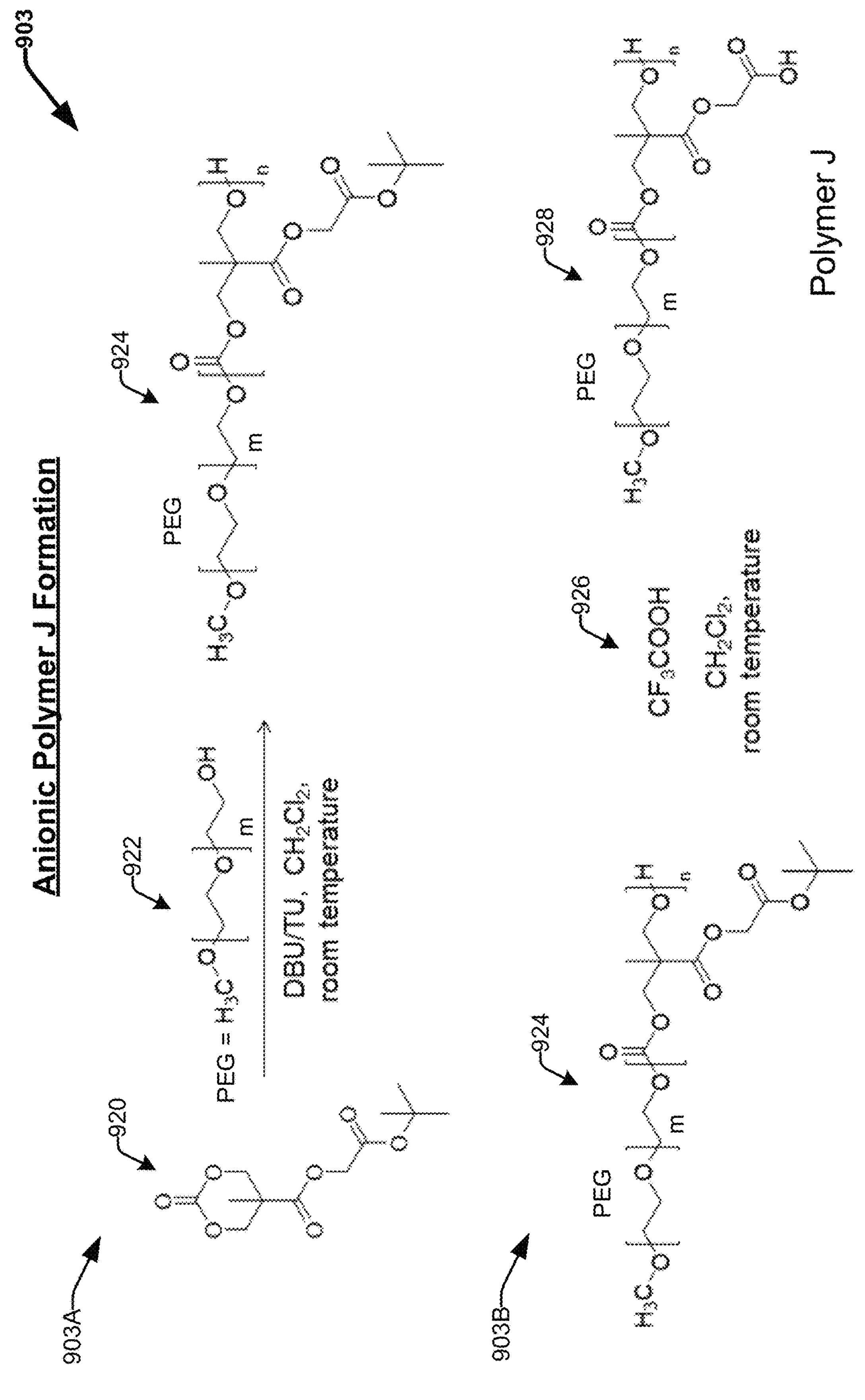
FIG. 9C presents an example synthesis route for forming Polymer J in accordance with various embodiments described herein. In the embodiment shown.

FIG. 9C presents an example synthesis route 903 for forming Polymer J in accordance with various embodiments described herein. Synthesis route 903 is described as a two-part reaction including route 903A followed by route 903B. With reference to route 903A, in the embodiment shown, a protected cyclic carboxylic acid monomer 920 can be reacted with reactants 922 including PEG, DBU/TU and $CH_2CL_2$ to form block copolymer 924 with a protected carboxylic acid group. In this regard, using the PEG as an initiator, a ROP of the protected cyclic carboxylic acid monomer 920 can be performed to generate the block copolymer 924 including a protected carboxylic acid group. In accordance with route 903B, the block copolymer 924 can further be reacted with reactants 926, including $CF_3COOH$ (trifluoroacetic acid) and $CH_2Cl_2$ at r.t., to deprotect the carboxylic acid group to generate the diblock acid functionalized polycarbonate referred to herein as Polymer J.

Figure 9D:
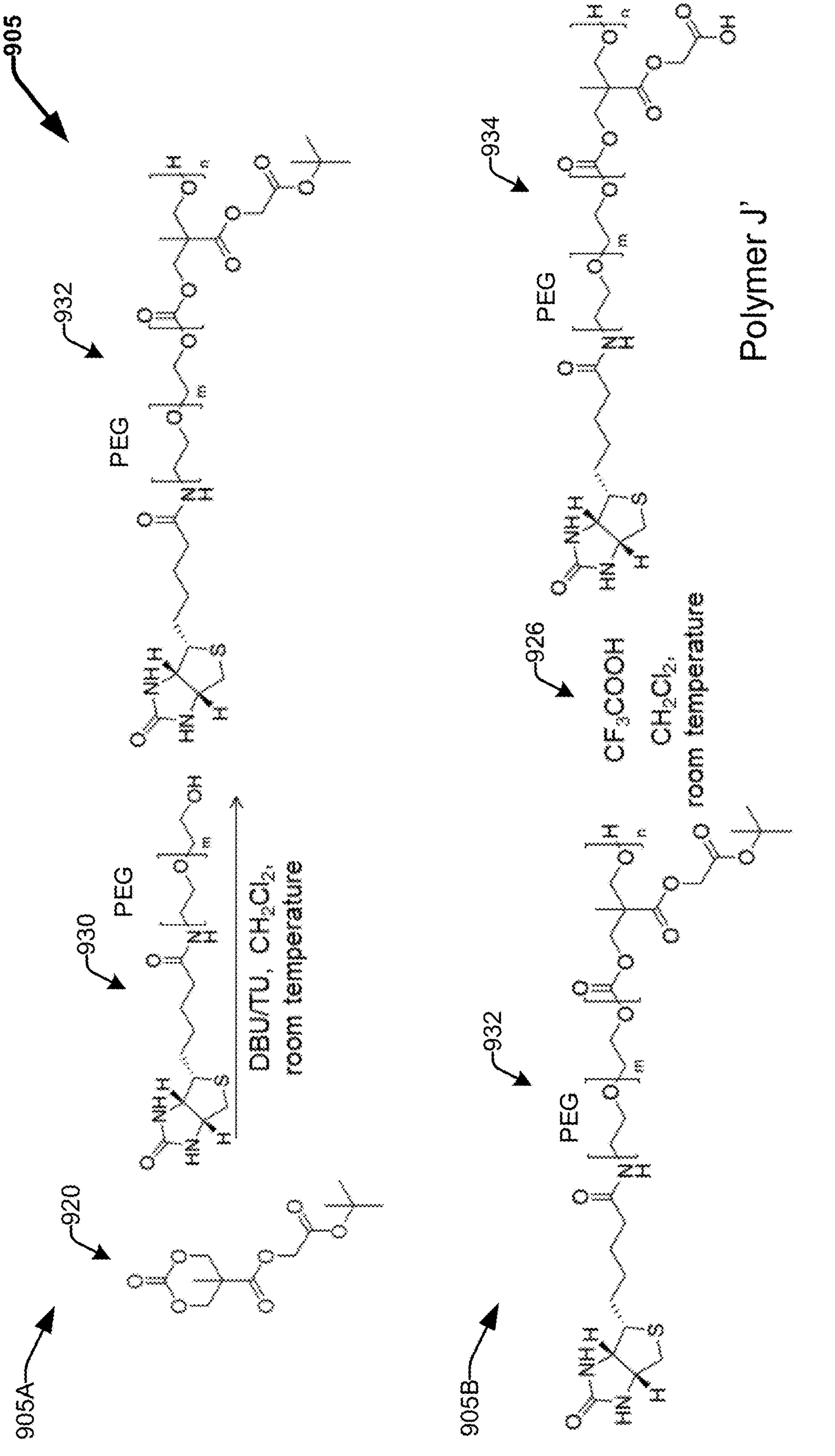
FIG. 9D presents an example synthesis route for forming Polymer J' in accordance with various embodiments described herein.

FIG. 9D presents an example synthesis route 905 for forming Polymer J' in accordance with various embodiments described herein. Synthesis route 905 is described as a two-part reaction including route 905A followed by route 905B. Synthesis route 905 is similar to synthesis route 903 with the addition of a biotin functional group to the PEG used for the ROP of the protected carboxylic acid monomer 920. Repetitive description of like elements employed in respective embodiments is omitted for sake of brevity. In accordance with synthesis route 905A, the protected carboxylic acid monomer 920 can be reacted with reactants 930 including biotinylated PEG, DBU/TU and $CH_2CL_2$ at r.t. to form the block copolymer 932. In this regard, using the biotinylated PEG as an initiator, a ROP of the protected cyclic carboxylic acid monomer 920 can be performed to generate the block copolymer 922 including a protected carboxylic acid group and a biotinol group. In accordance with route 905B, the block copolymer 923 can further be reacted with reactants 926, including $CF_3COOH$ (trifluoroacetic acid) and $CH_2Cl_2$ at r.t., to deprotect the carboxylic acid group to generate the biotinylated diblock acid functionalized polycarbonate referred to herein as Polymer J'.

Figure 10:
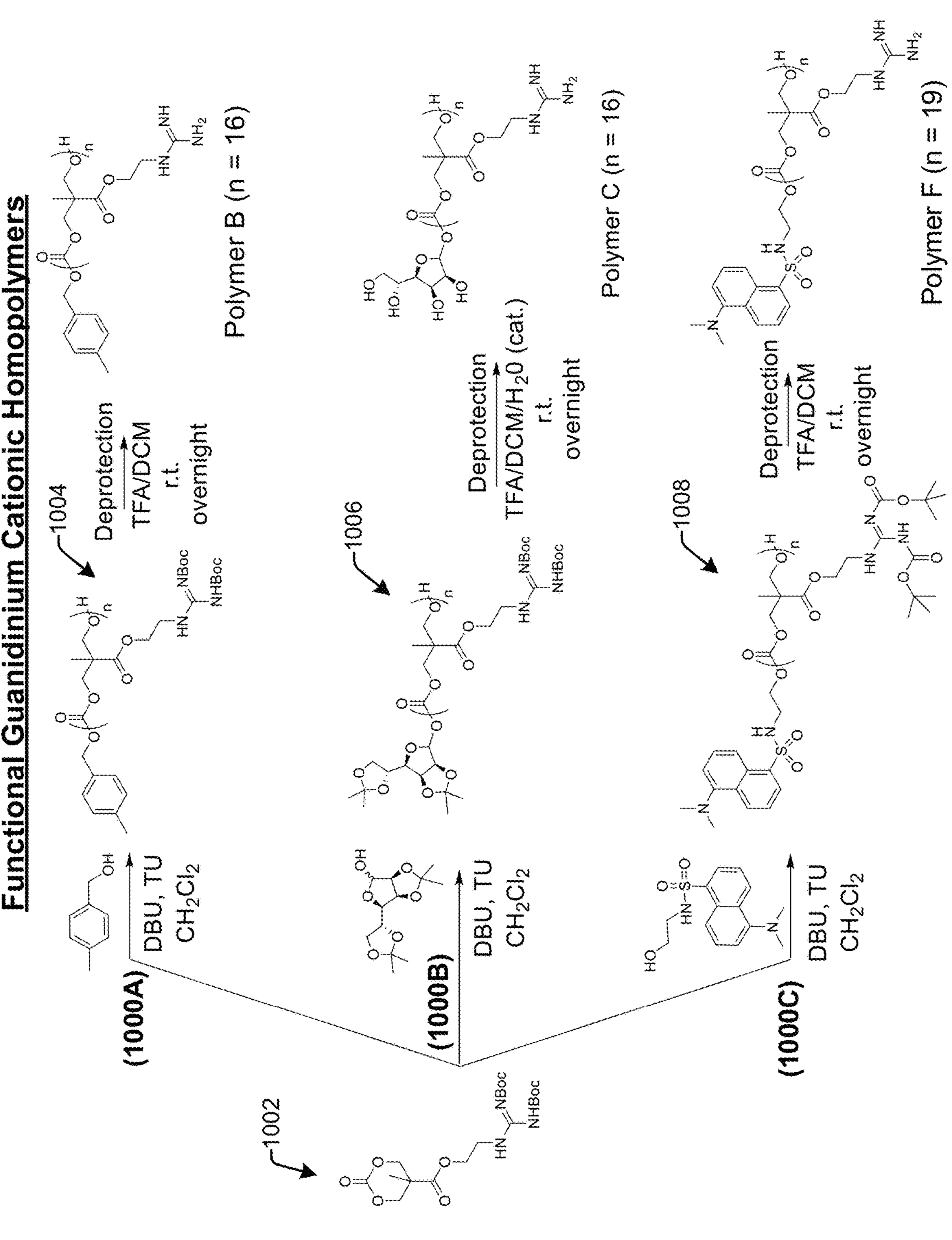
FIG. 10 presents example synthesis routes for forming functional guanidinium cationic homopolymers in accordance with various embodiments described herein.

FIG. 10 presents example synthesis routes for forming functional guanidinium cationic homopolymers Polymer B, Polymer C and Polymer F in accordance with various embodiments described herein. In the embodiment shown, the respective synthesis routes are identified as route 1000A, route 1000B and route 1000C. Route 1000A can be used to form Polymer B, route 1000B can be used to form polymer C and route 1000C can be used to form Polymer F. Each of these routes involve a ROP of guanidinium monomer 1002 with a different chemical initiator (and catalysts DBU, TU and solvent $CH_2CL_2$) to generate the corresponding protected homopolymers 1004, 1006 and 1008. For example, the initiator used with route 1000A comprises benzyl alcohol, the initiator used with route 1000B comprises a disaccharide (e.g., mannose), and the initiator used with route 1000C comprises a dansyl amid (a reactive fluorescent dye). The protected homopolymers 1004, 1006 and 1008 respectively, can subsequently be deprotected using TFA and DCM to generate the corresponding functional guanidinium cationic homopolymers including Polymer B, Polymer C and Polymer F, respectively.

Figure 11:
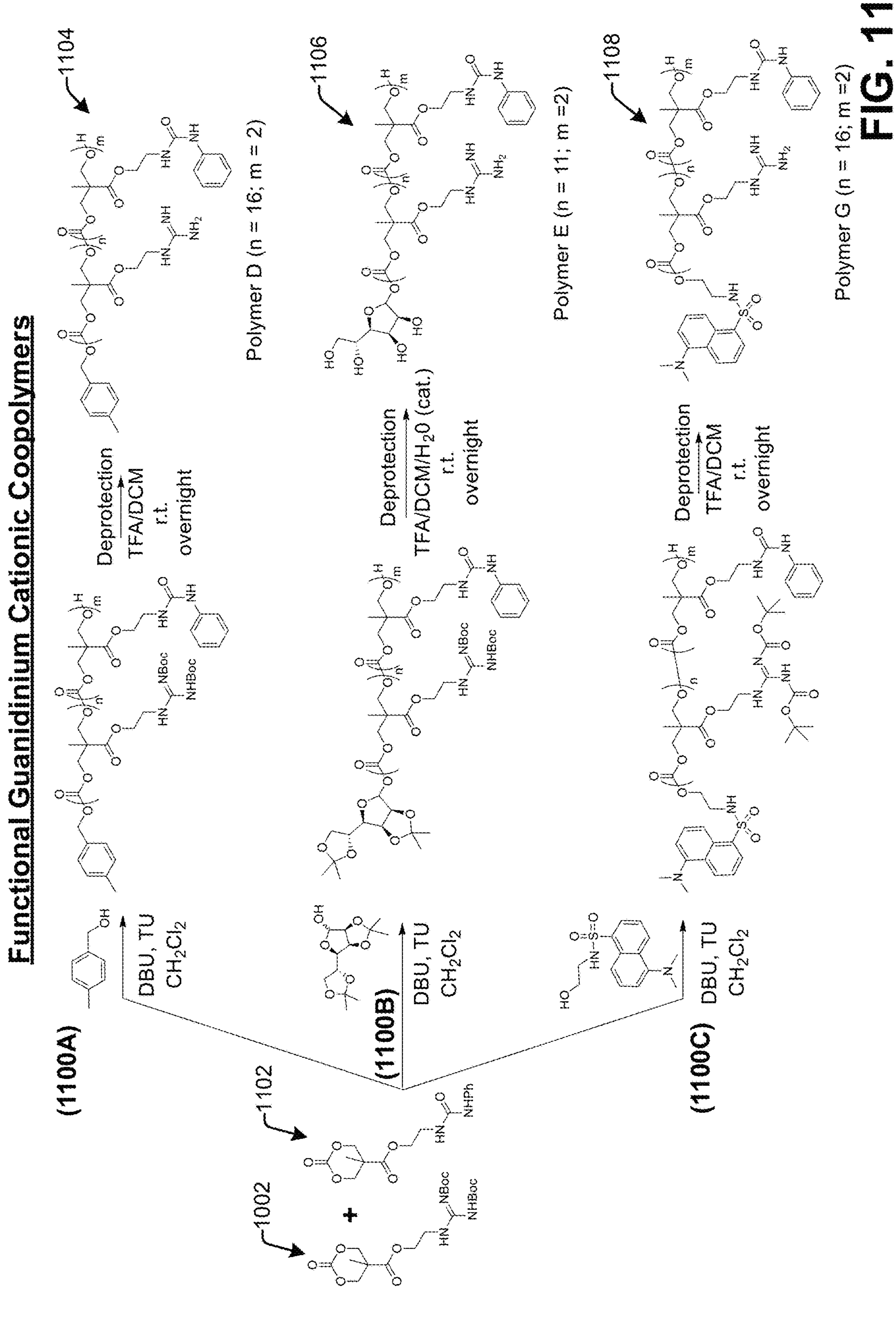
FIG. 11 presents example synthesis routes for forming functional guanidinium cationic copolymers in accordance with various embodiments described herein.

FIG. 11 presents example synthesis routes for forming functional guanidinium cationic copolymers, Polymer D, Polymer E and Polymer G, in accordance with various embodiments described herein. Repetitive description of like elements employed in respective embodiments is omitted for sake of brevity.

In the embodiment shown, the respective synthesis routes are identified as route 1100A, route 1100B and route 1100C. Route 1100A can be used to form Polymer D 1104, route 1100B can be used to form polymer E 1106, and route 1000C can be used to form Polymer G 1108. Routes 1100A, 1100B, and 1100C are similar to routes 1000A, 1000B and 1000C, respectively, with the addition of a urea monomer 1102 with the guanidinium monomer 1002. The urea monomer 1102 comprises a urea group (NH-carbonyl-NH). The urea monomer 1102 enhances the kinetic stability of the resulting functional guanidinium cationic copolymers (e.g., Polymer D, Polymer E, and Polymer G, respectively) and the subsequent coacervates that are formed when the cationic polymers are combined with an anionic polymer. The amount of urea monomer used can be less than the amount of guanidinium monomer used to form the respective polymers. For example, in the embodiments shown, the respective polymers can include 11 or 16 guanidinium monomer units and only 2 urea monomer units.

FIG. 12 provides a Table 1200 identifying physical characteristics of example therapeutic coacervate complexes in accordance with various embodiments described herein. In particular, Table 1200 identifies the particle size, the polydispersity index (PDI) and the zeta potential of various antimicrobials, including Complexes B, C, D, E and E'. Repetitive description of like elements employed in respective embodiments is omitted for sake of brevity.

The coacervates formed between one or more of the disclosed cationic therapeutic polymers and anionic carriers are well-defined complexes having a particle size less than 200 nm, 150 nm or 100 nm. In this regard, the coacervate complexes disclosed herein can be characterized as a nanocomplex or nanoplex. For example, as shown in Table 1200, Complex B exhibits a particle size at or near 132.0±1 nm, Complex C exhibits a particle size at or near 117.0±1 nm, Complex D exhibits a particle size at or near 138.0±1 nm, Complex E exhibits a particle size at or near 82.0±1 nm, and Complex E' exhibits a particle size at or near 71.0±1 nm. The small particle size of the subject coacervate complexes facilitates circulation of the coacervates and inhibits sequestering by mammalian cells in vivo. The small particle size further facilitates uptake of the complexes by cancer cells via the enhanced permeation retention effect (EPR). For example, as a tumor multiplies, the vascular around the tumor opens up, leaving holes that the small coacervates having a size less than 200 nm can fall into. Accordingly, the nanoparticle size of the subject coacervate complexes facilitates the transport of the polymer complex into the cancer/tumor cell for intracellular killing.

The respective complexes further exhibit low PDI. For example, Complex E and E' demonstrate a very narrow size distribution with a PDI of about 0.08±0.02 nm. Complexes B, C and D also exhibit low PDIs. The polydispersity index (PDI) (or more recently referred to as dispersity index), provides a measure of the distribution of molecular mass in a given polymer sample of the particles sizes. The lower the PDI, the more uniform the distribution of the particle size. A low PDI facilitates the antimicrobial and/or anticancer efficacy and/or selectivity of the subject coacervate complexes. For example, high PDI reflects a mixture of particles with vast size variation (some very large, some very small), which weakens the rate of update or permeation of the complexes intracellularly.

The zeta potential is a measure of electric charge associated with a molecule or macromolecule. The closer the zeta potential to zero, the more neutrally charged the complex, thereby promoting better circulation, and inhibiting in vivo sequestering by macrophages and biomolecules. Accordingly, a zeta potential close to zero is preferred. As shown in Table 1200, the subject Complexes respectively demonstrate relatively neutral zeta potentials, with Complex E and Complex E' demonstrating the lowest.

Complex E and Complex E' are highlighted in Table 1200 because these particular Complexes demonstrate higher overall physical characteristics relative the other coacervate Complexes. For example, complex E exhibits a particle size at or near 82.0±1 nm, with a very narrow size distribution or PDI of about 0.08±0.02, and a Zeta potential that is substantially zero, a −0.01±0.3 mV. Importantly, lyophilized Complex E gave similar size (97±4 nm) to its aqueous dispersion form (82±1 nm), and was able to re-disperse in water easily without using cryoprotectants. Complex E' exhibits similar PDI and Zeta potential characteristics as Complex E, with an even smaller particle size, at or near 72.0±1. Accordingly, Complex E and Complex E' are highly promising targets for antimicrobial and/or anticancer agents. Several example experiments described infra evaluating the selectivity and efficacy of the subject coacervate Complexes use Complex E and/or Complex E' as a primary example based in part on the superior physical properties exhibited by these complexes.

In addition to the excellent physical characteristics of the subject coacervate complexes described with reference to Table 1200, the coacervate complexes demonstrate strong kinetic stability under physiological conditions even in the presence of serum proteins.

Figure 13A:
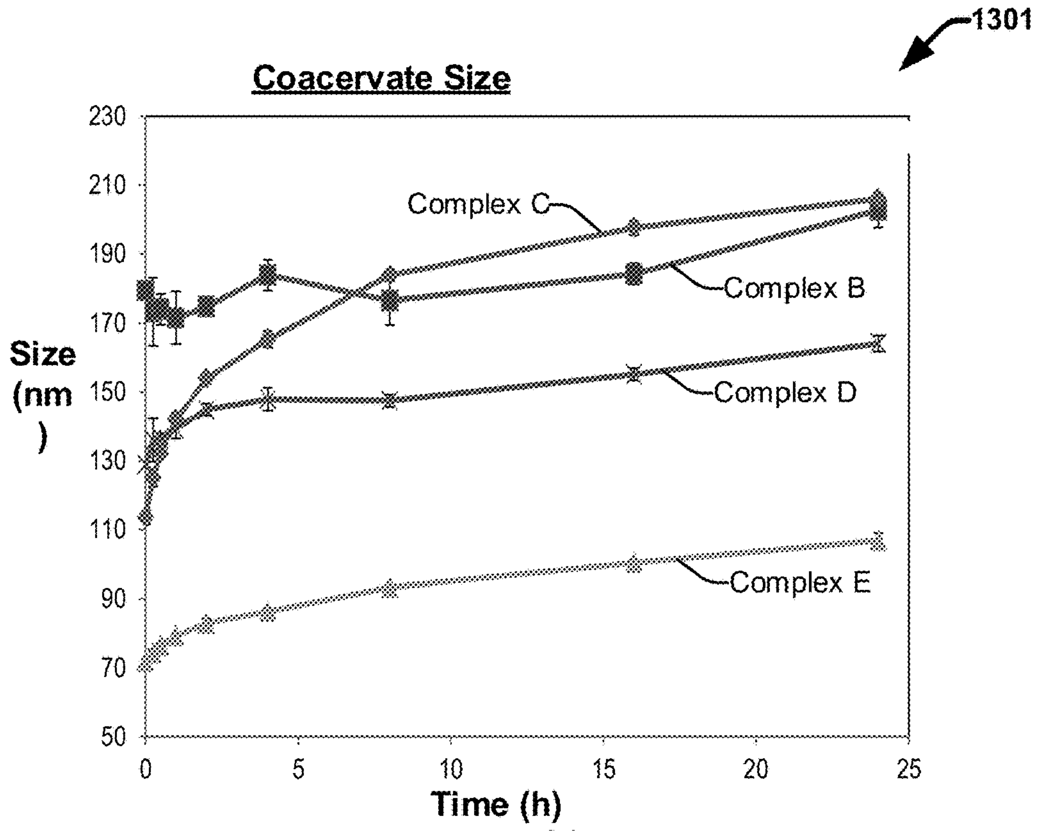
FIGS. 13A and 13B present graphs illustrating the kinetic stability characteristics of example coacervates in accordance with various embodiments described herein.
Figure 13B:
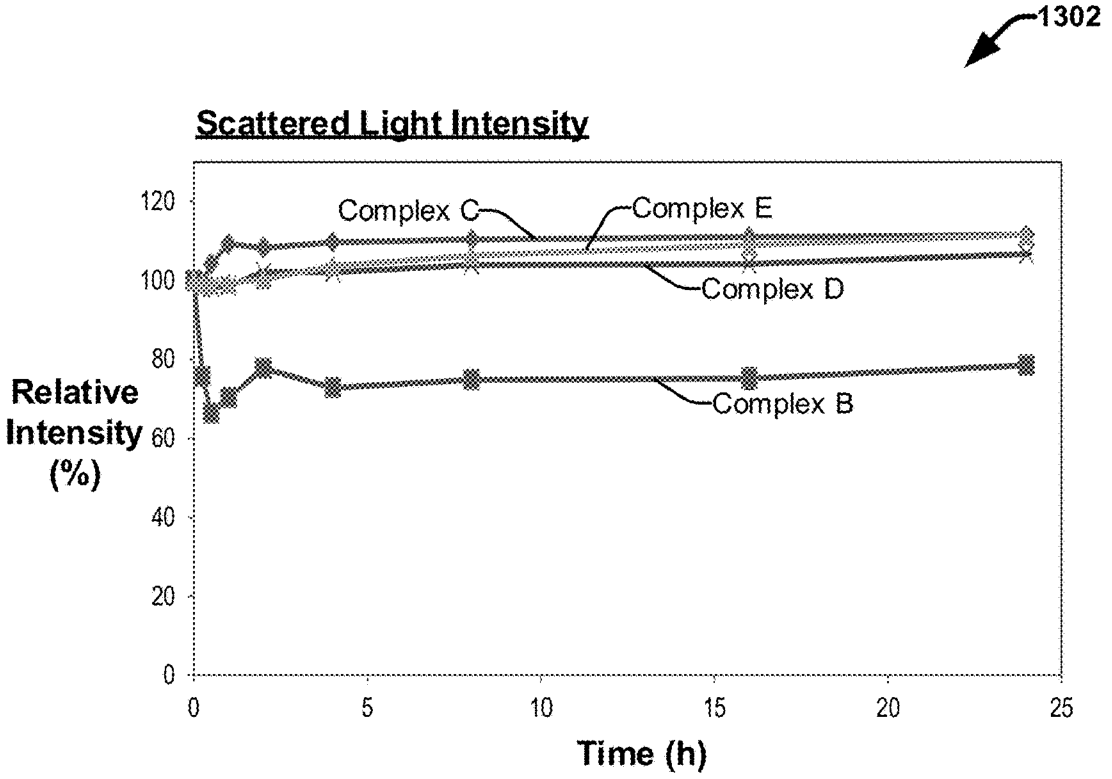

FIGS. 13A and 13B present graphs illustrating the kinetic stability of example coacervates in accordance with various embodiments described herein. The coacervates measured in graphs shown in FIGS. 13A and 13B include coacervates formed with anionic Polymer A, and respective cationic polymers B, C, D and E when mixed in a solution comprising deionized water (DI) with 10% fetal bovine serum. The coacervates formed are respectively include Complex B, Complex C, Complex D, and complex E. Repetitive description of like elements employed in respective embodiments is omitted for sake of brevity.

FIG. 13A presents a Graph 1301 demonstrating the change in coacervate size over time after the respective complexes are initially formed in the solution. As shown in Graph 1301, the size of the respective coacervates remained below 210 nm over a 24-hour period. This indicates that the respective complexes did not interact with and/or were not disrupted by biomolecules present in the fetal bovine serum. Thus, the respective coacervates demonstrate strong kinetic stability within serum without sequestering or interaction with serum proteins.

FIG. 13B presents a Graph 1302 demonstrating the change in scattered light intensity over time measured after addition of Triton-X to the DI water in which the respective coacervates are formed. The Triton-X is used to intentionally stress or destabilize the complexes to test their stability as a function of resistance to the Triton-X over time. In this regard, addition of the Triton-X to the DI water after formation of the complexes therein emulates the in vivo environment the complexes would encounter when injected into a mammalian model (e.g., from a solution into the body, a phenomenon referred to as infinite dilution). In Graph 1302, the relative intensity (%) is represented as the percentage of scattered light intensity at a variable time point relative to scattered light intensity at time h=0. As shown in Graph 1302, all of the measured coacervates (e.g., Complex B, Complex C, Complex D and Complex E), remained intact or substantially intact (e.g., did not disassemble) over a 24-hour period. This simulated experiment indicates that the disclosed coacervate complexes demonstrate strong kinetic stability in an in vitro environment.

Figure 14:
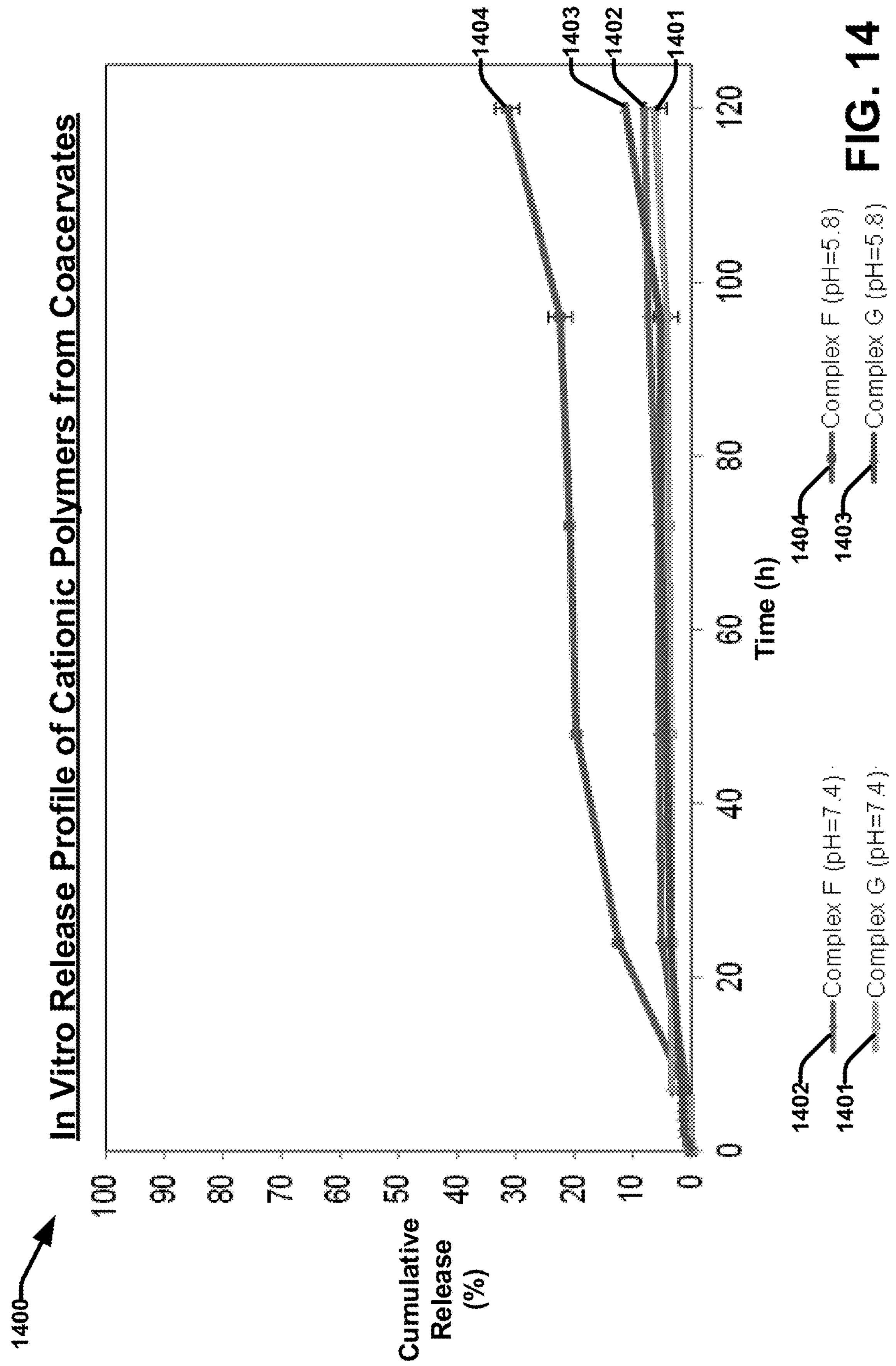
FIG. 14 presents a graph illustrating the in vitro release profile of cationic polymers from some example coacervates in accordance with various embodiments described herein.

FIG. 14 presents a Graph 1400 illustrating the in vitro release profile of cationic polymers from some example coacervates in accordance with various embodiments described herein. Graph 1400 depicts the results of an experiment in which coacervates including Complex F and Complex G were mixed in a phosphate buffered-saline (PBS) solution at 7.4 pH and 5.8 pH under simulated shaking conditions at 37° Celsius (C). This experiment tests the release of polymer F and G from the respective coacervates Complexes F and G as a function of time. As shown in Graph 1400, with respect to lines 1401, 1402, and 1403, release of Polymer F at a pH of 7.4 and Polymer G at a pH of 7.4 and 5.8 was slow over a 120-hour period. As indicated by line 1404, release of Polymer F at 5.8 pH was relatively higher over the 120-hour period, with a cumulative release less than 40%. Although the overall release of the cationic polymers was slow, they would dissociate from the complexes to bind anionic phosphate groups on bacterial membrane surface upon contact with bacteria and translocate across the membrane.

The various coacervate complexes disclosed herein, such as those identified in Table 1 and similar variations, have demonstrated strong selectivity and antimicrobial efficacy and specificity toward a variety of bacteria types including *P. aeruginosa*. The antimicrobial efficacy and/or specificity (or the degree of selectivity toward bacteria cells as opposed to mammalian cells) of the coacervate form of the various cationic therapeutic polyguanidiniums (e.g., Polymer B, Polymer C, Polymer D, Polymer, E, Polymer F, Polymer G, Polymer H and Polymer BG) when combined with an anionic Polymer (e.g., Polymer A, Polymer A', Polymer J, Polymer J' and the like) relative to the same cationic polyguanidiniums polymers alone was further increased. The coacervate complexes identified in Table 1 and variations thereof have also demonstrated strong specificity and efficacy as an anticancer agent for many different cancer cell lines. Similarly, the degree of selectivity of the coacervates toward cancer cells as opposed to mammalian cells and the degree of efficacy of the coacervates against cancer cells relative to their corresponding cationic polymers alone was further increased. FIGS. 15A-23 provide evidence-based data demonstrating these therapeutic properties and the disclosed coacervate complexes.

Figure 15A:
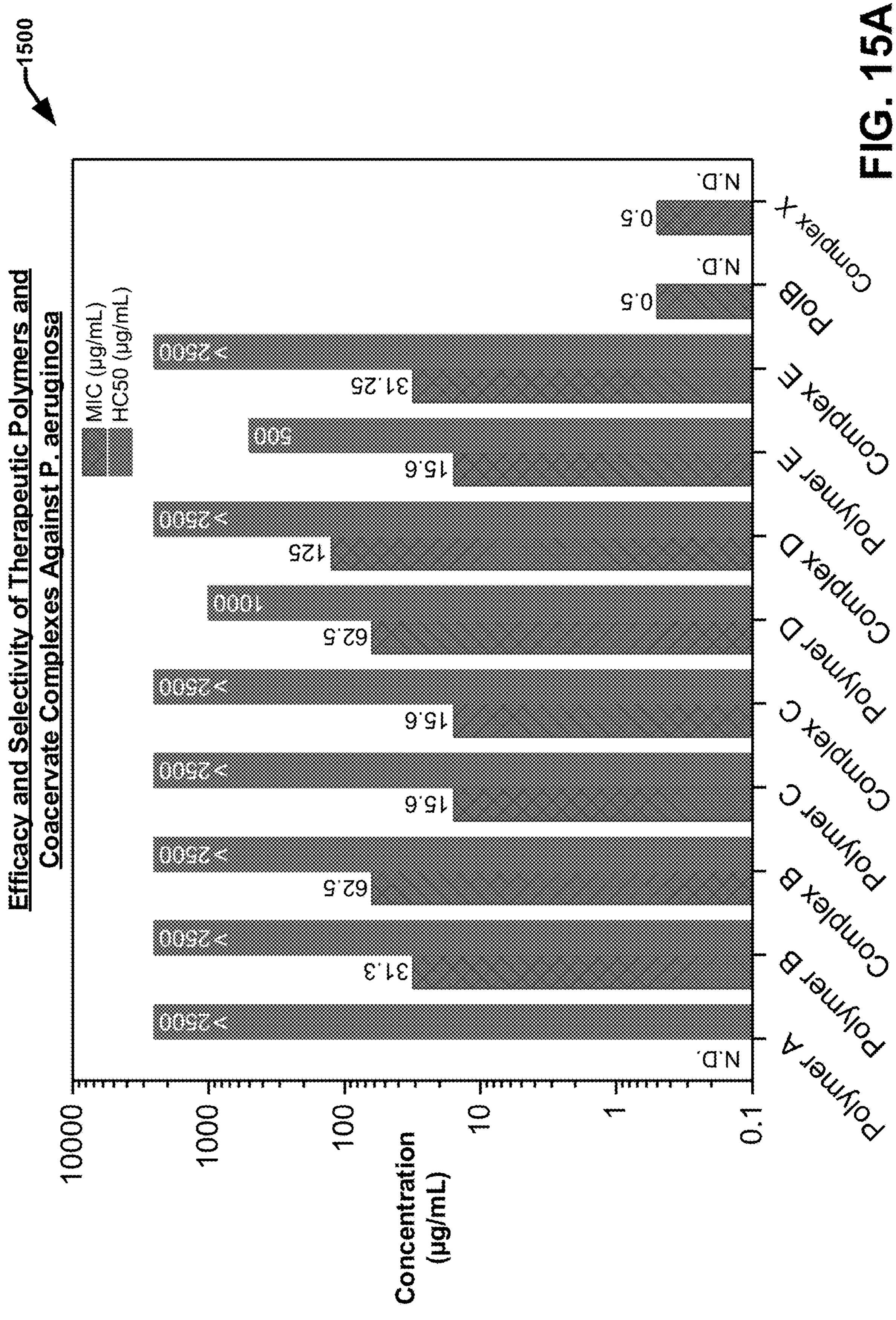
FIG. 15A presents a graph illustrating the antimicrobial selectivity and efficacy of example therapeutic polymers and coacervate complexes against *Pseudomonas aeruginosa* (*P. aeruginosa*) in accordance with various embodiments described herein.

FIG. 15A presents a Graph 1500 illustrating the antimicrobial selectivity and efficacy of example therapeutic polymers and coacervate complexes against *P. aeruginosa* in accordance with various embodiments described herein. In accordance with Graph 1500, individual polymers including Polymer A, Polymer B, Polymer C, Polymer D along with coacervates including Complex B, Complex C, Complex D and Complex E were tested for efficacy against *P. aeruginosa*. The tested efficacy is based on their respective minimal inhibitory concentrations (MICs) toward *P. aeruginosa*. Their selectivity/toxicity toward rat red blood cells (RBCs) was also tested, measured in hemolysis concentration (HC) 50 or (HC50), which corresponds to the amount of antibacterial agent required to kill 50% of the RBCs. The commercial standard antibiotic Polymyxin B sulfate (PolyB) and Complex X were also tested for selectivity and efficacy/toxicity for comparison. Complex X is used herein to refer to a coacervate complex formed with Polymer A in combination with PolyB (as opposed to Polymer A and the disclosed therapeutic polyguanidinium based Polymers). FIG. 15B provides a corresponding Table 1501 for Graph 1500. In addition to the MIC and HC50 values reflected in Graph 1500, Table 1501 also identifies the therapeutic index (SI) of the respective polymers and corresponding coacervate complexes. Repetitive description of like elements employed in respective embodiments is omitted for sake of brevity.

With reference to Graph 1500 and Table 1501, Polymer E alone (not in coacervate form) has an efficacy 15.6 μg/mL MIC, which is relatively higher compared to PolyB, which has an MIC of only 0.5 μg/mL. Polymer E also has a relatively low selectivity/toxicity toward RBCs represented by an HC50 value of 500 μg/mL. However, when Polymer E is combined with Polymer A to form Complex E, the selectivity substantially increases relative to Polymer E alone. In particular, compared to the HC50 value of 500 μg/mL for Polymer E, the HC50 value for Complex E skyrockets to beyond 2500 μg/mL. This is achieved with only a minor increase in the MIC amount for Complex E relative to Polymer E (from 15.6 μg/mL for Polymer E to 31.25 μg/mL for Complex E). Thus, Complex E demonstrates extremely low toxicity toward RBCs while providing strong antimicrobial efficacy. Based on this comparison of Polymer E with Complex E, it is evident that the coacervate form significantly increases selectivity without diminishing the antimicrobial efficacy.

FIG. 16 presents Table 1600 illustrating characteristics of example coacervate Complexes HJ with varying degrees of polymerization (DP). MIC values were obtained in *K. pneumoniae* (ATCC 700603). The coacervate Complexes shown in Table 1600, respectively include coacervate complexes formed with cationic Polymer H (cationic dansylated polyguanidinium having chemical Formula 15), and anionic Polymer J with a DP of 10, 20 and 30. Similar to the other coacervate complexes described herein, Complex HJ also demonstrates excellent physical characteristics for usage as an antimicrobial/anticancer agent. For example, with reference to Complex HJ with a DP of 20 (e.g., n=20), the complex has a size near 32 nm, a PDI of about 0.07±0.04 and a close to neutral surface (zeta potential: near −2.5±2.4 mV) when the acid/guanidinium molar ratio is 1:1. Complex HJ also has comparable antimicrobial activity against *K. pneumoniae* as compared to the polyguanidinium when the acid block has a DP of 20 and the acid/guanidinium molar ratio is 1.1 For example, as shown in Table 1600, Complex HJ with a DP of 20 and molar ratio of 1:1 has an MIC of 15.6 μg/mL which is similar to that of dansylated guanidinium Polymer H alone, which has an MIC of 7.8 μg/mL.

Figure 17:
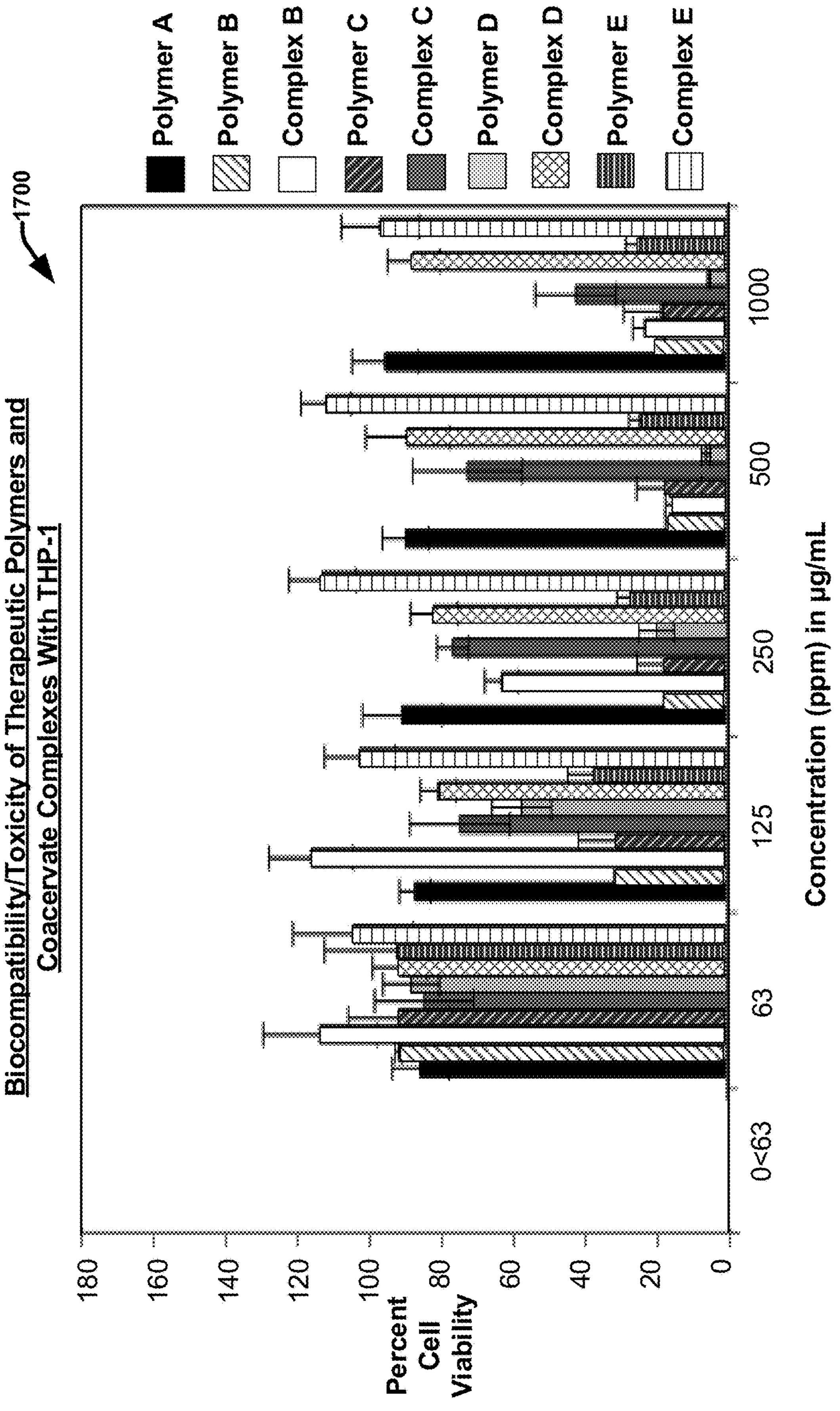
FIG. 17 presents is a graph illustrating the biocompatibility/toxicity of various therapeutic polymers and coacervate complexes with mammalian cells in accordance with various embodiments described herein FIG. 18 provides a graph illustrating the cell viability of mammalian cells with Polymyxin B (PolyB) and a coacervate form of PolyB in accordance with various embodiments described herein.

FIG. 17 presents a Graph 1700 illustrating the biocompatibility/toxicity of various therapeutic polymers and coacervate complexes with mammalian cells in accordance with various embodiments described herein. More particularly, Graph 1700 reflects the biocompatibility/toxicity of the various therapeutic polymers and coacervate complexes with THP-1 cells (a human monocytic cell line) as a function of cell viability at incrementally increased dosages. In accordance with the data reflected in Graph 1700, different dosages (e.g., from 2 ppm to 1000 ppm in μg/mL) of the respective polymers and coacervate complexes were incubated with the THP-1 cells for 24 hours at 37° C. The polymers tested include Polymer A, Polymer B, Polymer C, Polymer D, and Polymer E. The coacervates tested include Complex B, Complex C, Complex D, and Complex E. The percent cell viability detected at concentrations less than 63 ppm were substantially the same as those shown for 63 ppm, and thus are not depicted to minimize the complexity of the visualization.

With reference to the respective bars corresponding to Polymer E and Complex E, as the dosage increased from 63 ppm to 1000 ppm, the difference between the percent cell viability for Polymer E significantly drops from about 90% to about 25%. However, the percent cell viability for the coacervate formed with Polymer E and Polymer A, Complex E, remained substantially at or near 100%, event up to 1000 ppm. Similarly, with reference to the bars for Polymer D and Complex D, the percent cell viability for Polymer D alone dropped from more than 80% at 63 ppm to 5% at 1000 ppm, while Complex D demonstrated a cell viability at about 90% from 63 ppm to 1000 ppm. In this regard, Complex D and Complex E mitigated the toxicity of polymers D and E respectively, and did not showed significant cytotoxicity even at concentrations of 1000 ppm (in μg/mL). Thus, the disclosed coacervates, particularly Complex E and Complex D, demonstrate strong specificity toward bacteria cells and no or low toxicity toward mammalian cells.

Figure 18:
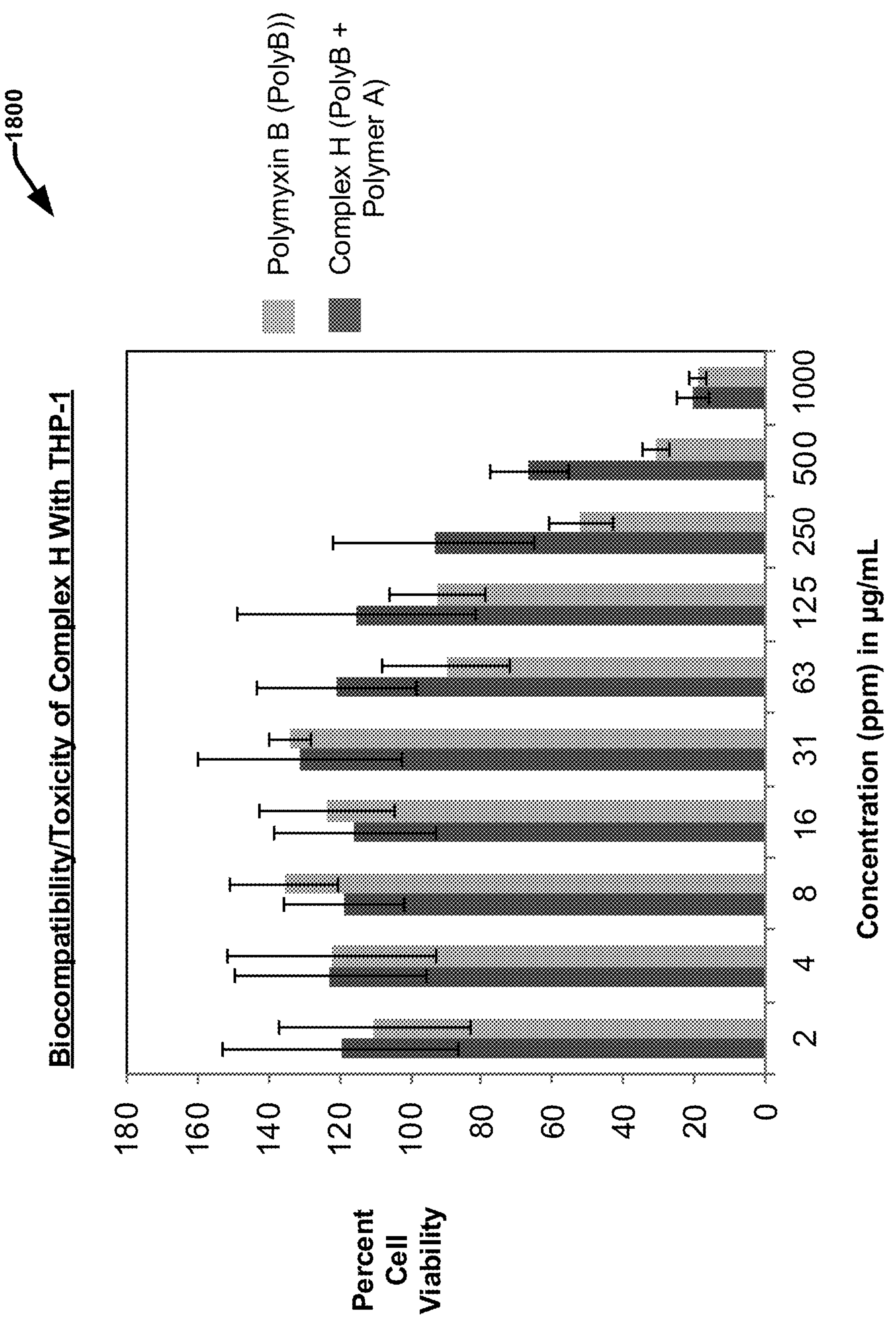

In contrast, FIG. 18 provides a Graph 1800 illustrating the cell viability of THP-1 with PolyB and a coacervate complex formed with PolyB and Polymer A, referred to herein as Complex H. As shown in Graph 1800, PolyB demonstrates high toxicity toward mammalian cells, with a 50% cell viability at about 250 ppm, and about a 30% cell viability at about 500 ppm, dropping to below 20% at 1000 ppm. Furthermore, the integration PolyB with Polymer A into the coacervate Complex H, did not substantially mitigate the toxicity of PolyB at 500 ppm or greater. In this regard, in contrast to Complex D and Complex E, Complex X was unable to mitigate the toxicity of the corresponding cationic antimicrobial polymer alone high concentrations (e.g., 500 ppm or greater).

Figure 19:
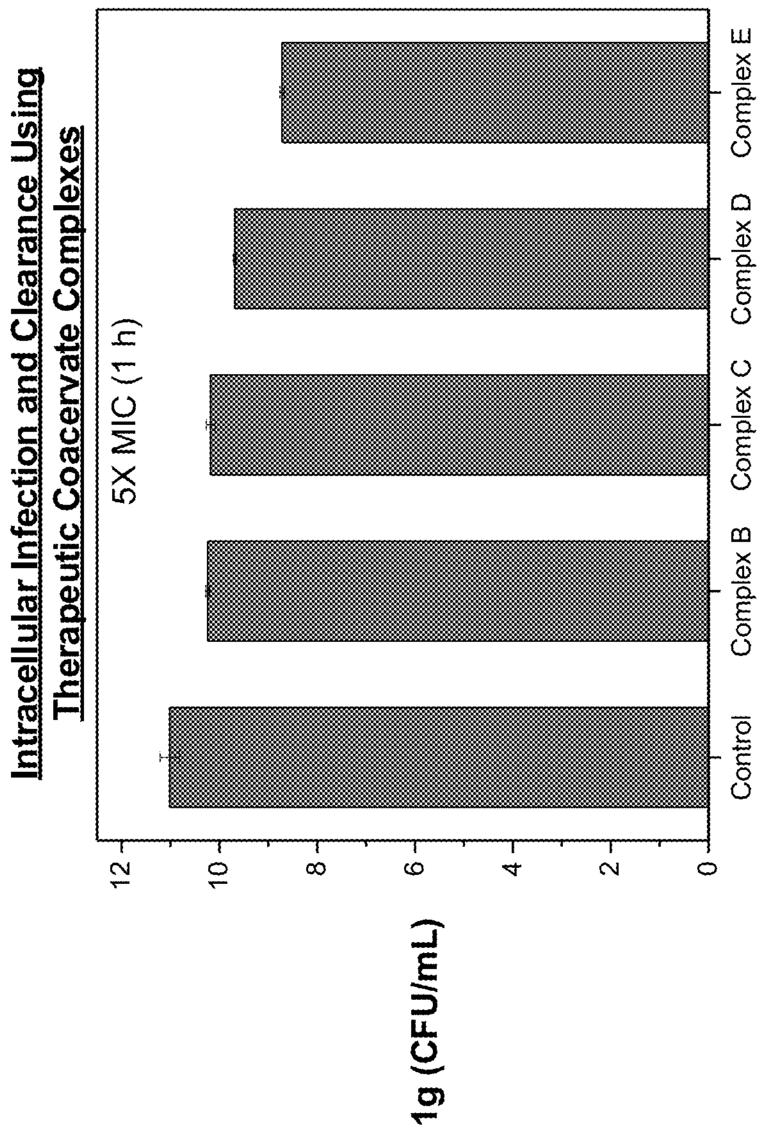
FIG. 19 presents a graph illustrating the intracellular *P. aeruginosa* infection clearance using various coacervate embodiments described herein.

FIG. 19 presents a graph 1900 illustrating the intracellular infection clearance of example coacervates with *P. aeruginosa* in accordance with various embodiments described herein. Not all bacteria cells are floating freely within an infected body. Many bacterial infections involve intracellular infections, wherein bacteria cells translocate into other cells and macrophages. In order to combat intracellular bacterial infections, the antibacterial agent must possess an ability to kill intracellular bacteria cells.

Graph 1900 demonstrates the results of an experiment in which Complex B, Complex C, Complex D and Complex E were respectively incubated with a sample comprising intracellular *P. aeruginosa* for a period of 1 hour. As shown in Graph 1900, each of these respective complexes successfully eradicated 99% of intracellular *P. aeruginosa* after incubation for only 1 hour. Thus, as exemplified with reference to Graph 1900, Complex B, Complex C, Complex D and Complex E demonstrate strong antimicrobial efficacy against intracellular bacterial infections, including *P. aeruginosa.*

Figure 20A:
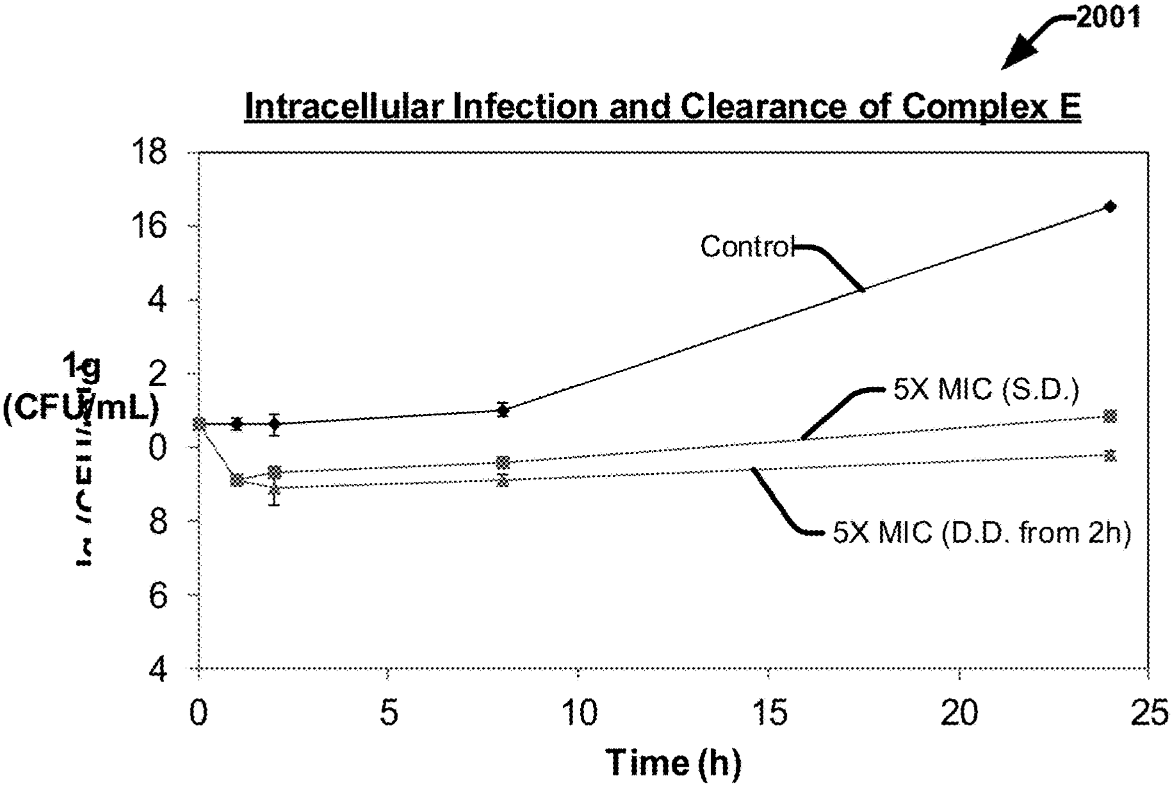
FIGS. 20A and 20B present graphs illustrating the intracellular infection clearance of Complex E with *P. aeruginosa* in accordance with various embodiments described herein.
Figure 20B:
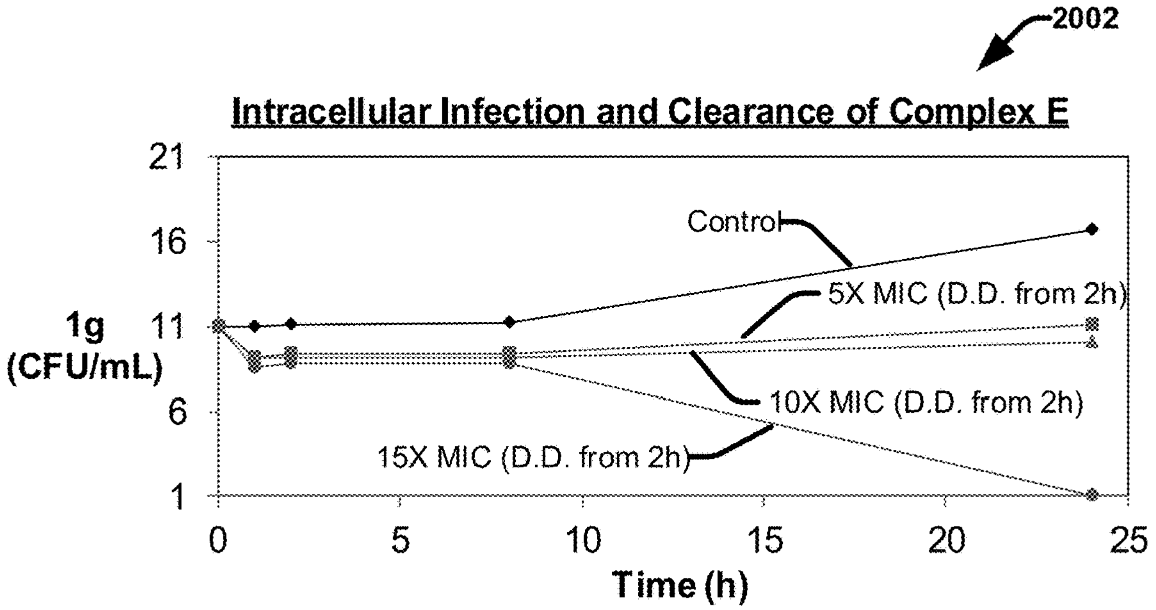

FIGS. 20A and 20B present graphs further illustrating the intracellular infection clearance of Complex E with *P. aeruginosa* in accordance with various embodiments described herein. FIG. 20A presents a Graph 2001 demonstrating incubation of Complex E with samples comprising cells with intracellular *P. aeruginosa* at different dosages of 5×MIC over a period of 24 hours. In accordance with Graph 2001, a first sample of intracellular *P. aeruginosa* was given a single dose (S.D.) of Complex E and incubated for 24 hours. A second sample of intracellular *P. aeruginosa* was given double doses (D.D.) of Complex E, at 5×MIC. In particular, with the second sample, a single dose (S.D.) of Complex E initially (at 0 hours) and given a second dose one hour later and left to incubate for the remaining 23 hours. FIG. 20B presents a Graph 2002 demonstrating incubation of Complex E with samples comprising cells with intracellular *P. aeruginosa* with double dosages of 5×, 10× and 15×MIC over a period of 24 hours. In accordance with Graph 2002, for all three samples (a first given 5×MIC, a second giving 10×MIC and a third given 15×MIC), the first dose was administered at time 0 hours and the second dose was administered two hours later.

As shown in Graphs 2001 and 2002, as the dose and MIC level increased the amount of eradicated intracellular *P. aeruginosa* also increased. This demonstrates that the dose of Complex E can be calibrated to selectively eradicate 100% of intracellular *P. aeruginosa.*

FIGS. 21A and 21B provides tables illustrating the in vivo toxicity and antimicrobial efficacy of coacervate complexes in accordance with various embodiments described herein. FIG. 21A provides a Table 2101 demonstrating the in-vivo toxicity in mice, and FIG. 21B provides a Table 2102 demonstrating the in-vivo antimicrobial efficacy. The data presented in both tables 2101 and 2102 reflect testing using a mouse model.

With reference to FIG. 21 and Table 2101 the in vivo toxicity of different antimicrobials was measured as a function of the lethal dose 50 (LD50) values (which is the amount of antimicrobial that kills 50% of the tested population). As shown in Table 2101, the commercial antimicrobial PolyB exhibits extremely high toxicity with an LD50 value of 5.4 milligrams per kilogram (mg/kg). This high toxicity level does not change when PolyB is administered in a coacervate complex with Polymer A. Polymer E alone provides a much better toxicity level relative to PolyB, with an LD50 value between 17.5 and 50 mg/kg, which is below the therapeutic does. However, this does not compare to toxicity level of Complex E. In this regard, Complex E has an LD50 value that goes beyond 175 mg/kg. In fact, the LD50 level of Complex E is so high that is cannot be measured. This demonstrates that Complex E is an extremely safe and non-toxic to mammals. This in-vivo toxicity data is further commensurate with the in vitro toxicity data and in vitro hemolysis data discussed above.

With reference to FIG. 21B, the data in Table 2102 reflect treatment of a blood infected mouse model with Complex E and Complex E'. In accordance with the results shown in Table 2102, mice infected with 200 μL of *P. aeruginosa* at 5 to $7\times10^6$ CFU/mL, with a body weight between 23 and 25 grams, were injected with either Complex E or Complex E'. Interestingly, although Complex E demonstrate impressive in vitro antibacterial efficacy, when used in vivo, Complex E' proved to be more effective in vivo. In this regard, the mice treated with Complex E were unable to survive the infection with a dose of 42.2 mg/kg. However, mice treated with Complex E' were effectively cured with a dose of 42.2 mg/kg. These results demonstrate that the addition of biotin to the disclosed cationic polymers significantly enhances their antimicrobial efficacy of the polymer in vivo.

Figure 22:
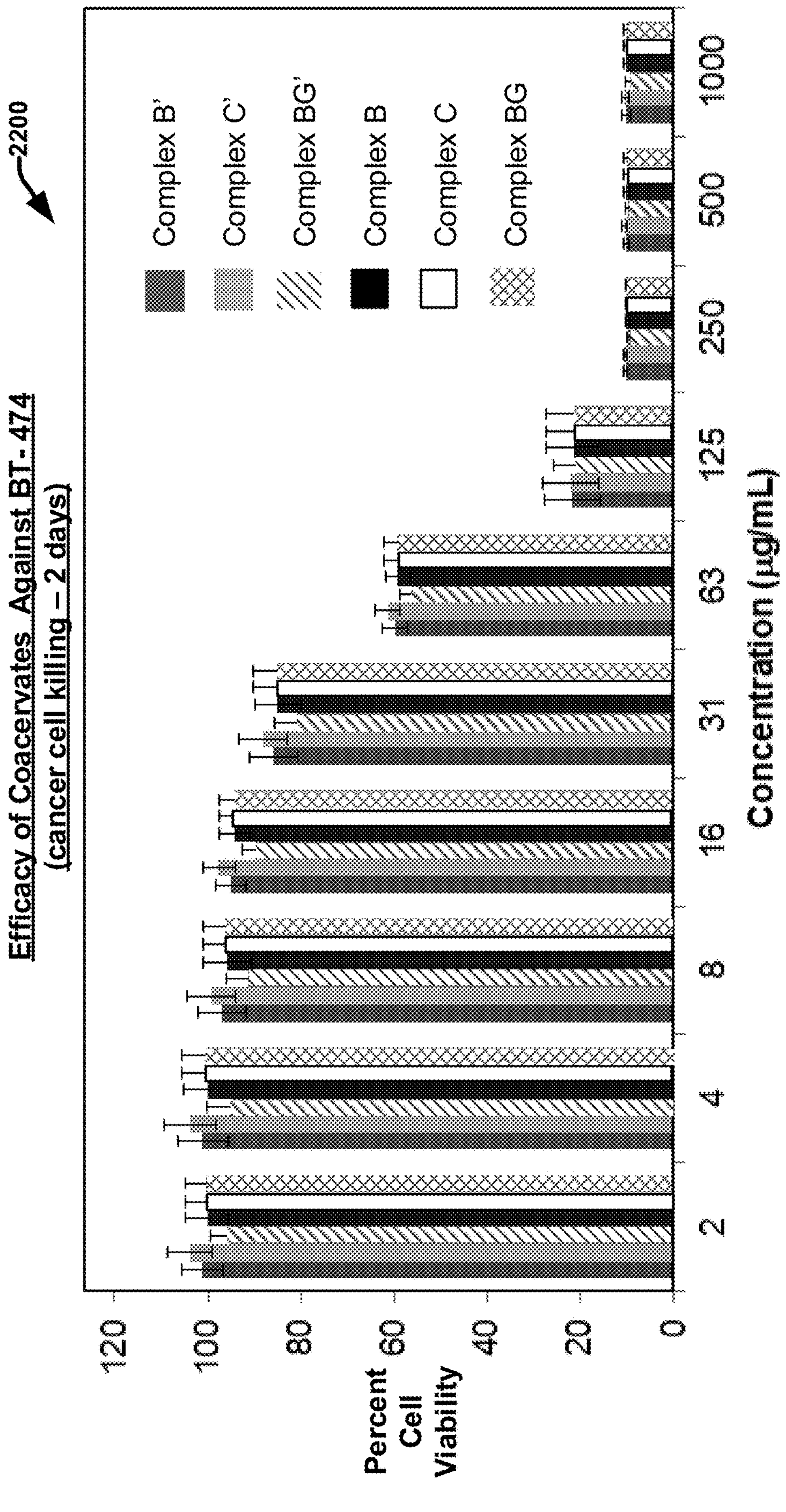
FIG. 22 provides a graph demonstrating the efficacy of various coacervate complexes against BT-474 cancer cells in accordance with various embodiments described herein.
Figure 23:
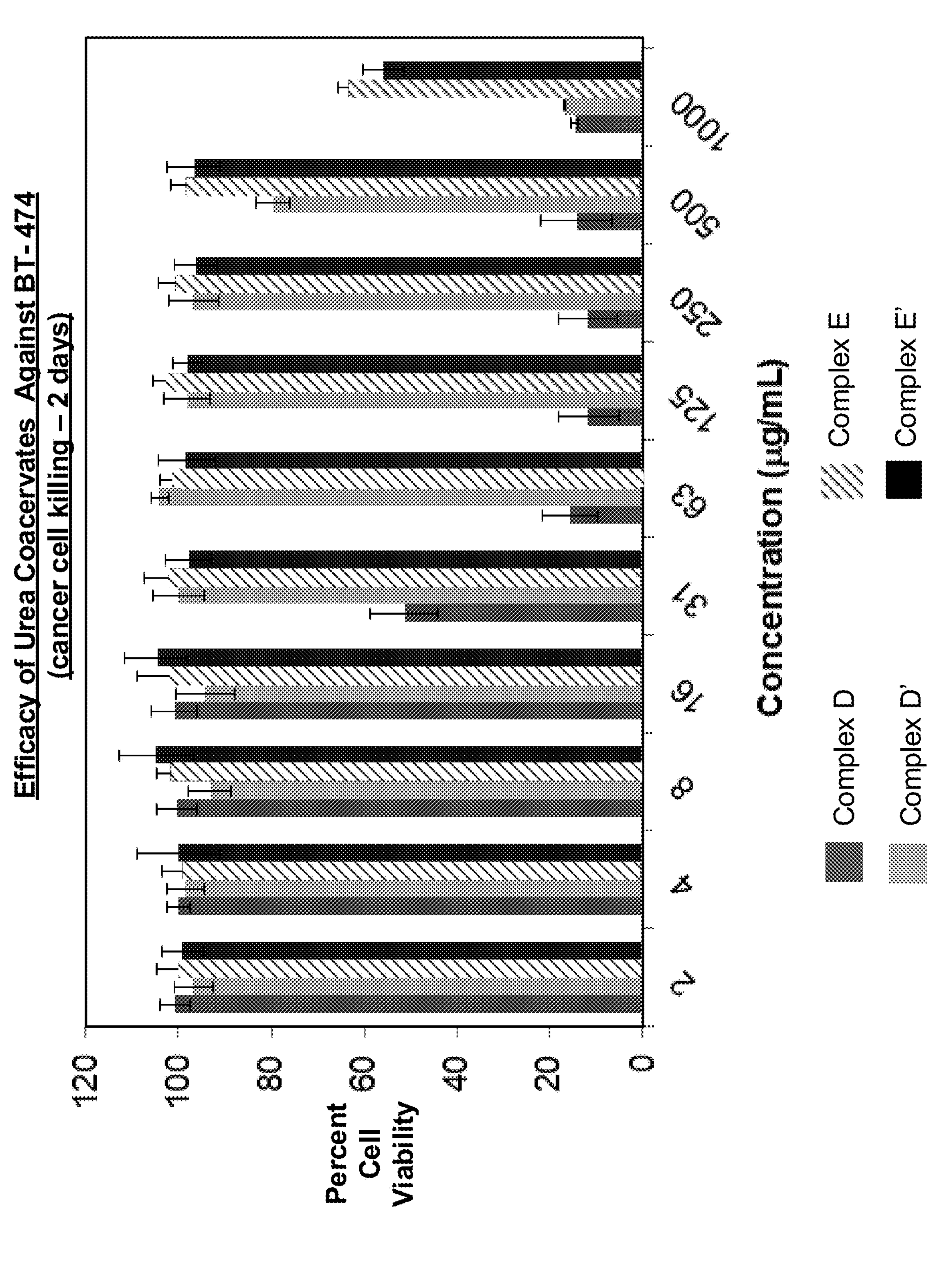
FIG. 23 provides a graph demonstrating the efficacy of various coacervate complexes with urea against BT-474 cancer cells in accordance with various embodiments described herein.
Figure 24:
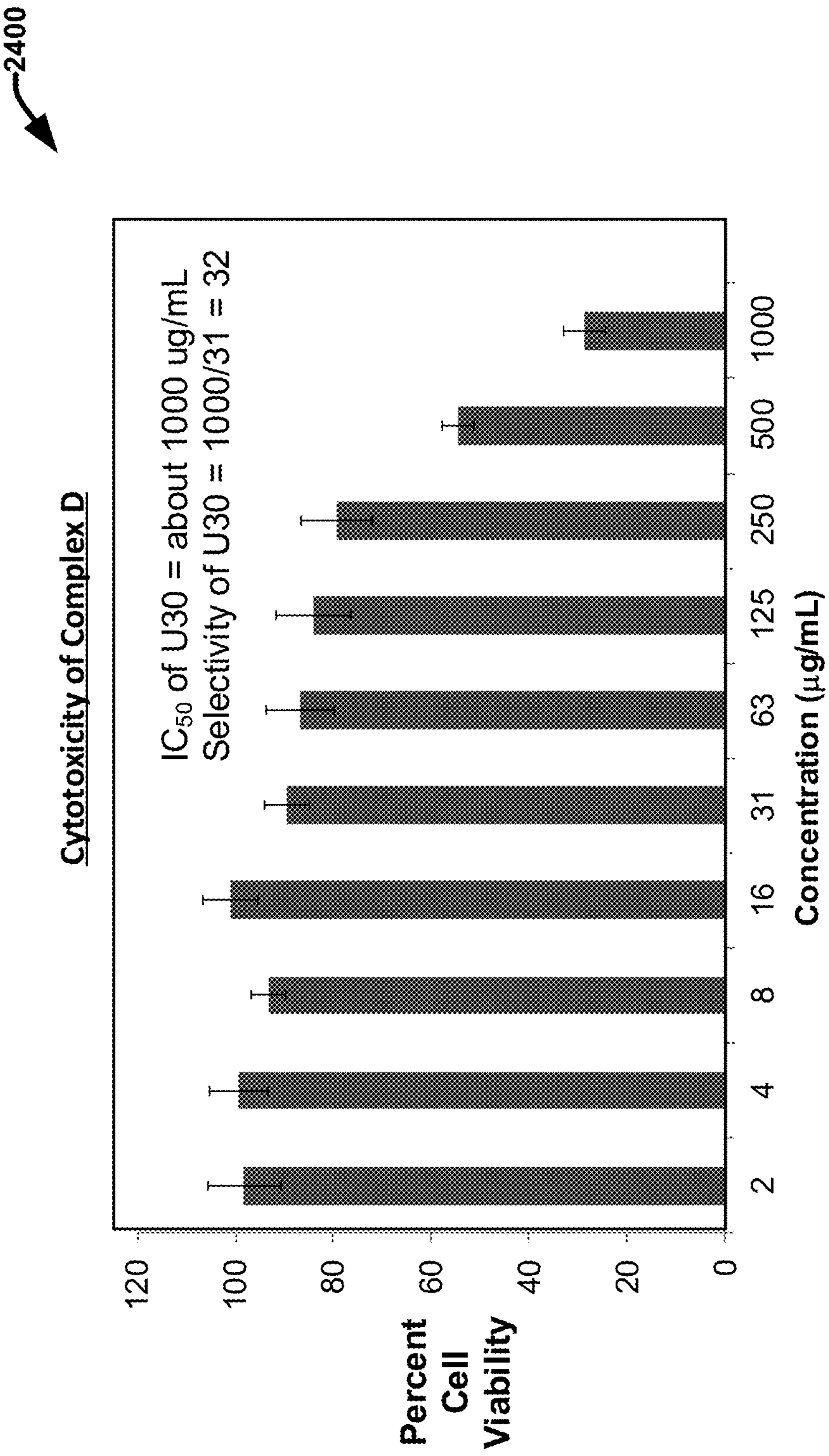
FIG. 24 presents a chart illustrating the cytotoxicity of a coacervate Complex D against healthy non-cancerous mammalian cell line HEK293 in accordance with various embodiments described herein.

Thus far, the antimicrobial selectivity and efficacy of the disclosed therapeutic coacervates has been demonstrated. In addition to antimicrobial efficacy, one or more embodiments of the disclosed coacervates can also serve as an excellent anticancer agent against various cancer cell lines with enhanced selectivity and efficacy relative to solo cationic therapeutic polymers. FIGS. 22-24 demonstrate some example anticancer properties of various coacervates in accordance with one or more embodiments described herein. Repetitive description of like elements employed in respective embodiments is omitted for sake of brevity.

FIG. 22 provides a Graph 2200 demonstrating the efficacy of various coacervate complexes against BT-474 cancer cells in accordance with various embodiments described herein. The coacervate complexes tested include Complex B', Complex C', Complex BG', Complex B, Complex C, and Complex BG. The anticancer efficacy of the respective coacervates was tested as a function of cell viability using an MTT assay. As shown in Graph 2200, all of the tested coacervate complexes demonstrated strong anticancer efficacy with IC50 concentrations between 63 and 125 μg/mL. The respective complexes further substantially eradicate the diseased cells at concentrations greater than 125 μg/mL ppm. In this regard, taking into account that that the respective complexes are two component systems wherein 50% of the complex is a sulfonate, and only a portion of the cationic polymer comprises the active therapeutic component, the relative amount of active agent represented in the 63 to 125 μg/mL is less than half. Thus, the relative amount of toxic active agent included in the dosage amount required to eradicate the cancer cells is substantially less than 63 to 125 μg/mL. Furthermore, as demonstrated with reference to the cytotoxicity and hemolysis data presented above, the toxicity of the example coacervates remains low even at high concentrations (e.g., concentrations greater than a LD50 value of 175 mg/kg).

FIG. 23 provides a Graph 2300 demonstrating the efficacy of coacervate complexes with urea against BT-474 cancer cells in accordance with various embodiments described herein. In particular, Graph 2300 demonstrates the efficacy of Complex D and Complex D' (which respectively include a small amount of urea), and Complex E and Complex E' (which respectively include a small amount of urea and mannose). As shown in Graph 2300, Complex D demonstrated high efficacy against BT-474 with a 50% cell viability at only 31 μg/mL and less than 20% cell viability at 63 μg/mL or greater. However, Complex D' with the added biotin only demonstrated significant efficacy at much high concentrations (e.g., 500 to 1000). This indicates that the presence of urea negatively interacts with biotin, causing the biotin functional group to be sequestered into the core of the micelle. Complex E and Complex E' also demonstrated efficacy against BT-474, however only at high concentrations (e.g., greater than 500 or 1000 ppm). Accordingly, Complex D is the more promising anticancer agent against BT-474.

FIG. 24 presents a Chart 2400 illustrating the cytotoxicity of a coacervate Complex D against healthy non-cancerous mammalian cell line HEK293 in accordance with various embodiments described herein. In accordance with Chart 2400, the cytotoxicity of Complex D against HEK293 was tested as a function of polymer concentration using an MTT assay. As shown in Chart 2400, almost 100% of the HEK293 cells survived at concentrations of Complex D at the therapeutic amount of 31 ppm (μg/ml). This high cell viability remained even up to concentrations up to 500 ppm. Complex D further demonstrated an $IC_{50}$ of 1000 μg/mL and thus a selectivity of =1000/31=32. This demonstrates that Complex D not only demonstrates strong efficacy as an anticancer agent against BT-474, but also demonstrate strong selectivity toward diseased cells over healthy mammalian cells, and those poses a very low toxicity level.

Figure 25:
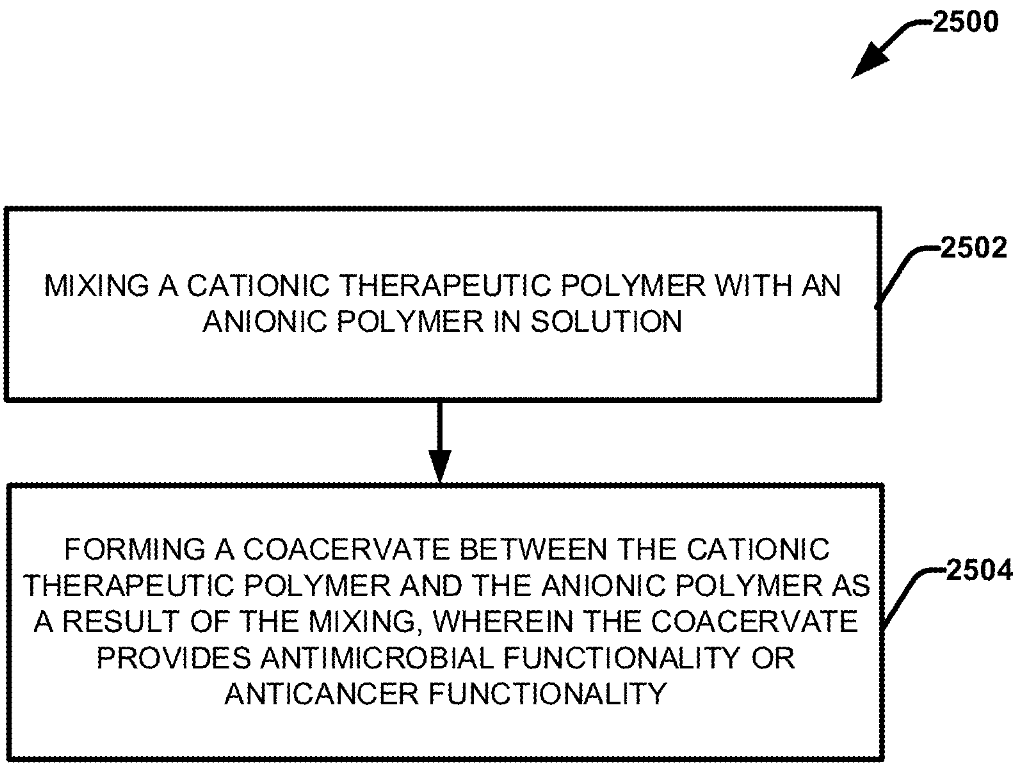
FIG. 25 presents a high-level flow diagram of an example method for enhancing the selectivity and efficacy of therapeutic polymers against a broad spectrum of pathogens and cancer cell lines using a coacervate complex in accordance with various embodiments described herein.

FIG. 25 presents a high-level flow diagram of an example method 2500 for enhancing the selectivity and efficacy of therapeutic polymers against a broad spectrum of pathogens and cancer cell lines using a coacervate complex in accordance with various embodiments described herein. Repetitive description of like elements employed in respective embodiments is omitted for sake of brevity.

At 2502, a cationic therapeutic polymer (e.g., Polymer E, Polymer B, Polymer C, Polymer F, Polymer D, Polymer G, BG and the like) can be mixed with an anionic polymer (e.g., Polymer A, Polymer A' and the like) in solution (e.g., water, serum, etc.). At 2504, a coacervate complex can be formed between the cationic therapeutic polymer and the anionic polymer as a result of the mixing, wherein the coacervate provides antimicrobial functionality or anticancer functionality.

Figure 26:
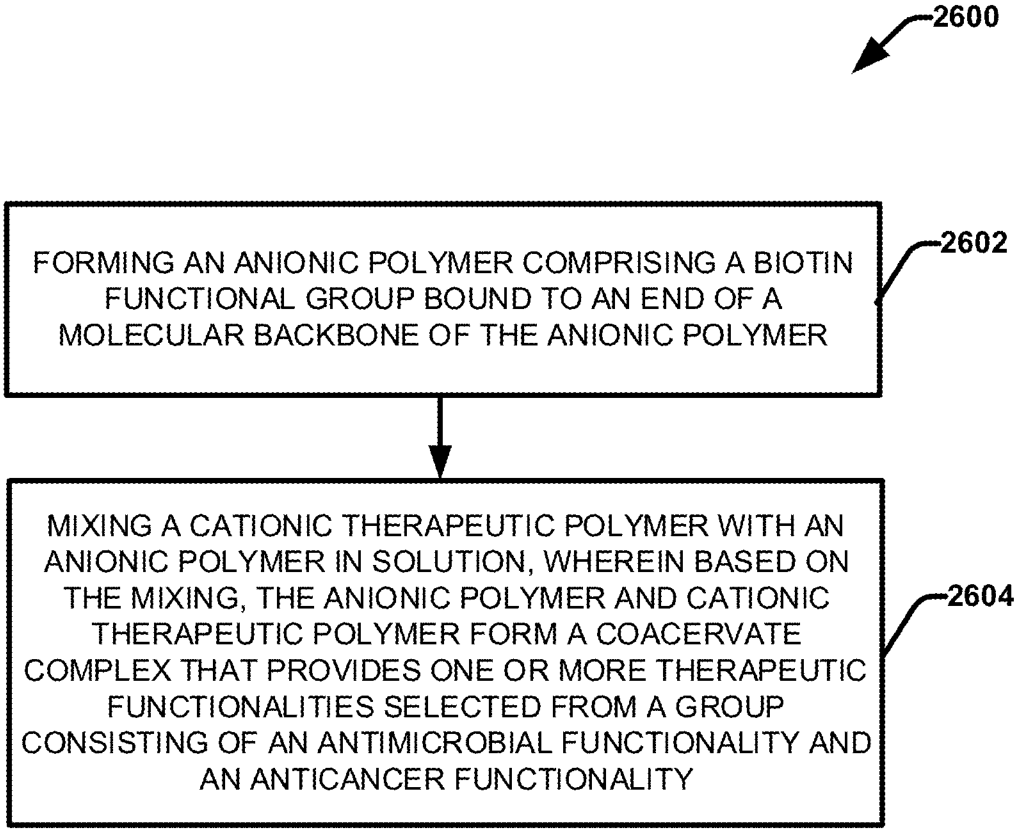
FIG. 26 presents a high-level flow diagram of an example method for enhancing the selectivity and efficacy of therapeutic polymers against a broad spectrum of pathogens and cancer cell lines using a coacervate complex comprising a biotinylated anionic polymer in accordance with various embodiments described herein.

FIG. 26 presents a high-level flow diagram of an example method 2600 for enhancing the selectivity and efficacy of therapeutic polymers against a broad spectrum of pathogens and cancer cell lines using a coacervate complex comprising a biotinylated anionic polymer in accordance with various embodiments described herein. Repetitive description of like elements employed in respective embodiments is omitted for sake of brevity.

At 2602 an anionic polymer can be formed comprising a biotin functional group bound to an end of a molecular backbone of the anionic polymer (e.g., Polymer A' or the like). At 2604, a cationic therapeutic polymer (e.g., Polymer E, Polymer B, Polymer C, Polymer F, Polymer D, Polymer G, and the like) can be mixed with an anionic polymer in solution, wherein based on the mixing, the anionic polymer and the cationic therapeutic polymer form a coacervate complex that provides one or more therapeutic functionalities selected from a group consisting of an antimicrobial functionality and an anticancer functionality III—Fluorescence Coacervate Diagnostics One or more additional embodiments of the disclosed subject matter are directed to usage of the above described coacervates for diagnostic purposes. In accordance with these embodiments, a fluorescent dye functional group can be attached to the aniconic polymer and combined with a cationic polymer to form a coacervate complex in solution (e.g., DI water). The cationic polymer can be calibrated to target or react with a specific pathogen and/or cancer cell type. The fluorescent properties of the dye are quenched as a result of the formation of the coacervate complex when the functionalized anionic polymer is combined with the cationic polymer. However, when the coacervate opens up as a result of interaction between the cationic polymer with the target pathogen or cancer cell type, the anionic polymer is released and the fluorescent dye illuminates. Thus, detection of luminescence in response to exposure of the cationic complex to a fluid sample (e.g., urine, saliva, etc.) can indicate the specific target pathogen or cancer cell is present.

Figure 27:
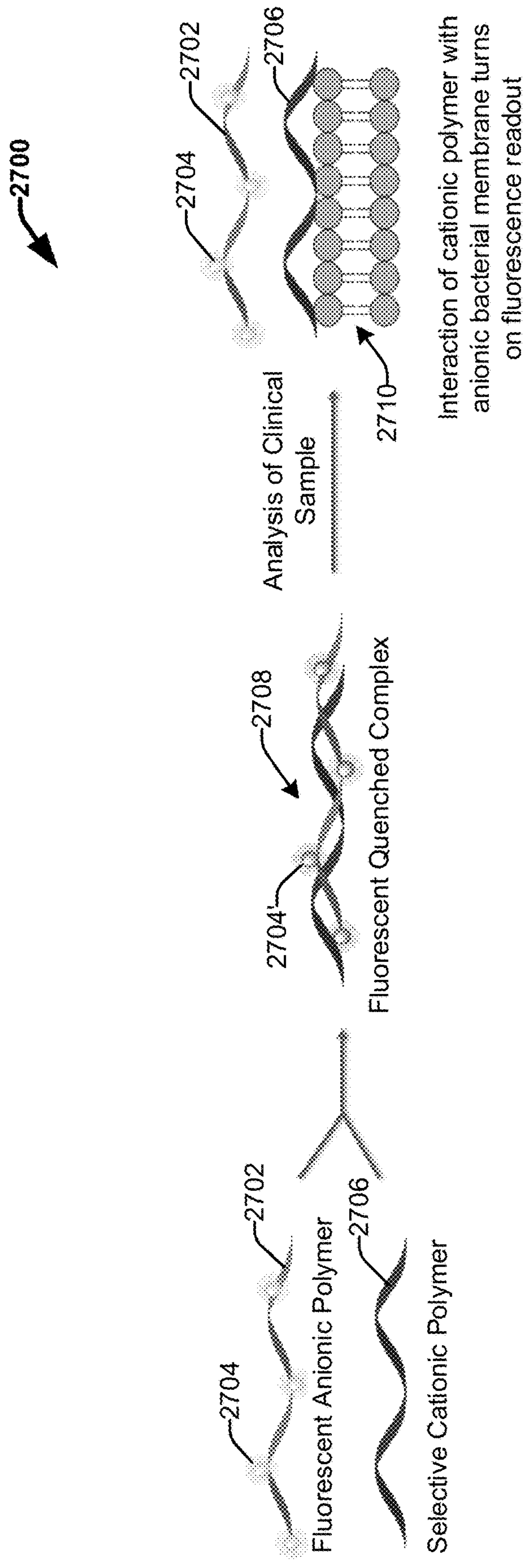
FIG. 27 provides a diagram illustrating fluorescence based coacervate diagnostics in accordance with various embodiments described herein.

FIG. 27 provides a diagram illustrating a fluorescence based coacervate diagnostic process 2700 in accordance with various embodiments described herein. Repetitive description of like elements employed in respective embodiments is omitted for sake of brevity.

In accordance with process 2700, an anionic polymer such as Polymer A, Polymer A' or the like, can be labeled with a fluorescent die to form fluorescent anionic polymer 2702 comprising fluorescent functional groups 2704. The fluorescent anionic polymer 2702 can further be combined with selective cationic polymer 2706 that has been calibrated or tailored to only react with a specific target biomarker, such as a specific type of bacteria and/or bacteria strain, a specific type of cancer cell, or the like. For example, in various embodiments, the selective cationic polymer 2706 can comprises a functional guanidinium cationic homopolymer (e.g., Polymer B, Polymer C, Polymer BG, etc.), a functional guanidinium cationic copolymer (e.g., Polymer D, Polymer E, etc.), a block copolymer or the like. When the fluorescent anionic polymer 2702 is separated from the selective cationic polymer 2707, the fluorescent functional groups 2704 can be configured to illuminate. However, when the fluorescent anionic polymer 2702 and the selective cationic polymer 2706 self-assemble into a coacervate complex 2708, the fluorescent functional groups 2704 become quenched and an unable to emit light (as indicated by the change from the fluorescent functional groups 2704 to the quenched state 2704').

This quenched form of coacervate complex 2708 can further be mixed with a clinical sample of comprising biological fluid (e.g., urine, saliva, interocular fluid, blood, etc.) to facilitate detecting presence of the target biomarker. In this regard, if the biomarker (e.g., the specific target bacteria type/strain, the specific cancer cell type, etc.) is present in the clinical sample, the selective cationic polymer with interact with the target biomarker, resulting in the release of the fluorescent anionic polymer 2702 therefrom and the unquenching of the fluorescent functional groups. As a result, the functional groups will emit light. For example, in various embodiments, the selective cationic polymer 2706 can interact with the anionic surface of the bacterial membrane 2710 (or the cancer cell membrane) and perform an ion exchange therewith, causing the fluorescent anionic polymer 2702 to be released. In this regard, the presence and/or amount of the target biomarker present in the clinical sample can be determined based on detection of light/photon emission and/or an amount of light/photons emitted from the clinical sample. In various embodiments, a fluorometer or another suitable instrument can be used to detect and measure the fluorescent light/photon emission. The amount of light/photons emitted can thus be correlated to a specific target biomarker which can further be correlated to a specific infection, disease, condition, etc.

Figure 28:
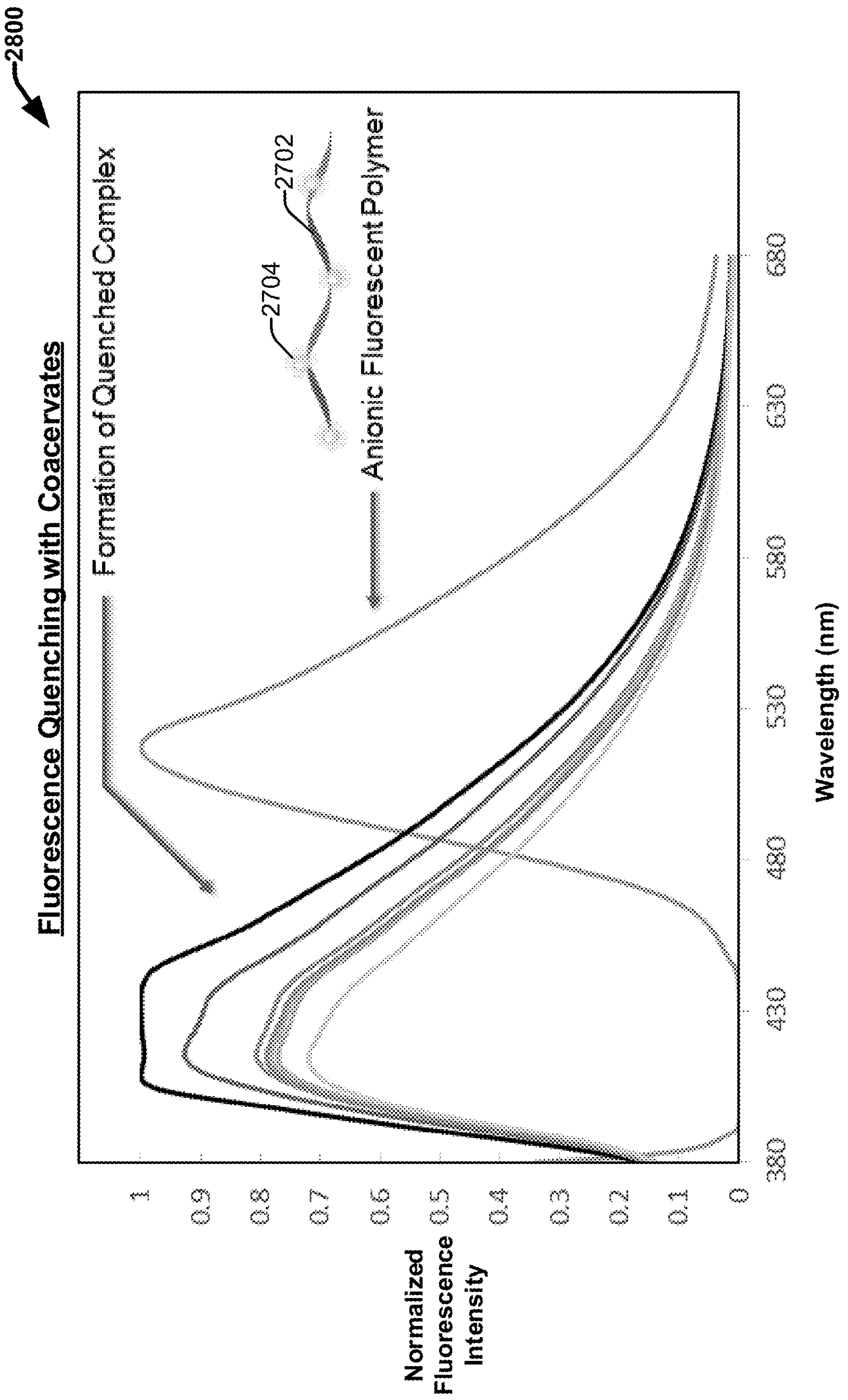
FIG. 28 presents a graph illustrating the fluorescence quenching characteristics of diagnostic coacervate complexes in accordance with various embodiments described herein.

FIG. 28 presents a Graph 2800 illustrating the fluorescence quenching characteristics of diagnostic coacervate complexes in accordance with various embodiments described herein. As shown in Graph 2800, the free floating, fluorescent anionic polymer 2702 emits a significantly higher wavelength relative to the quenched coacervate complexes.

Figure 29:
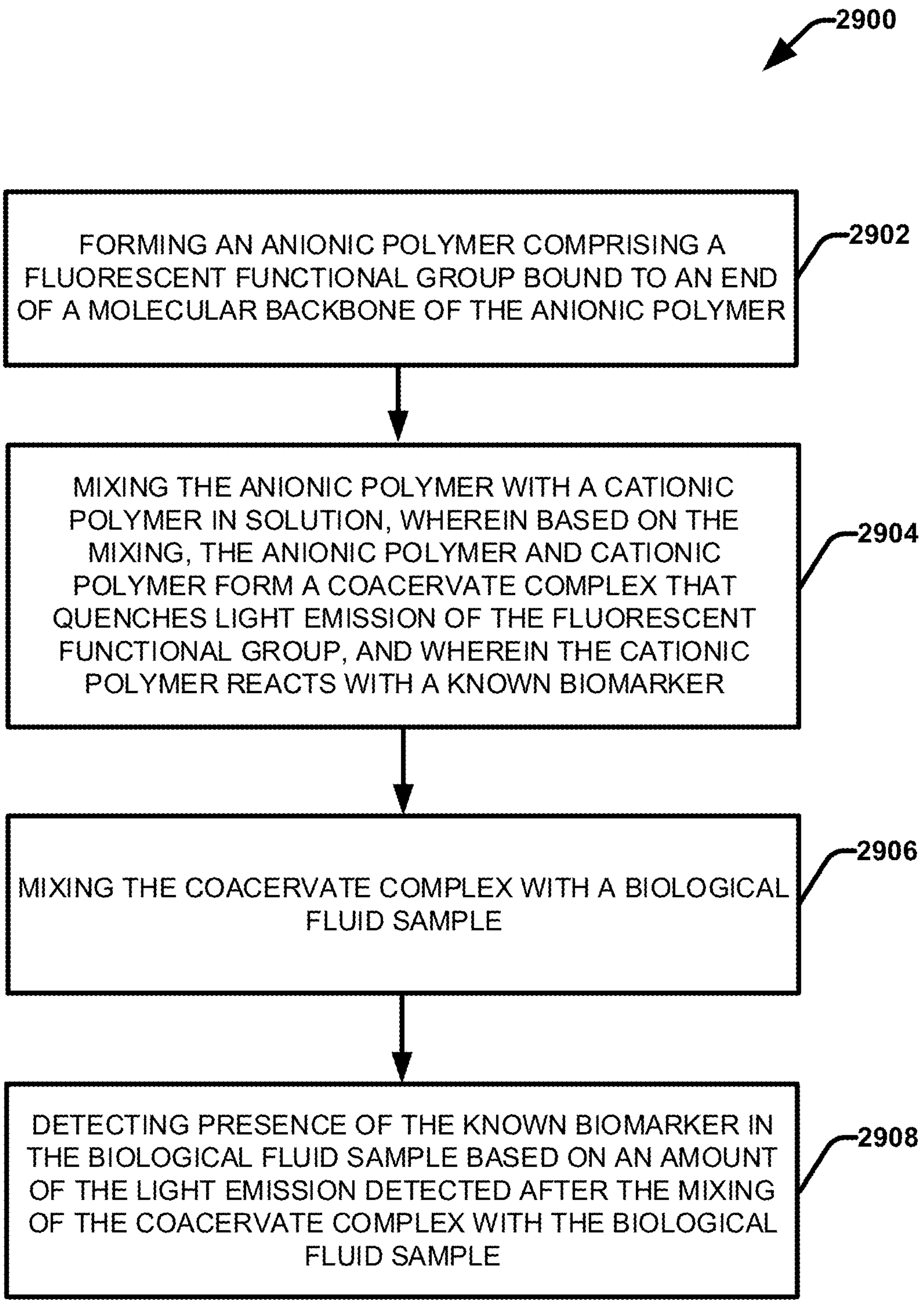
FIG. 29 presents a high-level flow diagram of an example method for diagnosing a disease or condition using a fluorescence based coacervate assay in accordance with various embodiments described herein.

FIG. 29 presents a high-level flow diagram of an example method 2900 for diagnosing a disease or condition using a fluorescence based coacervate assay in accordance with various embodiments described herein. Repetitive description of like elements employed in respective embodiments is omitted for sake of brevity.

At 2902, an anionic polymer can be formed comprising a fluorescent functional group bound to an end of a molecular backbone of the anionic polymer. At 2904, the anionic polymer can be mixed with cationic polymer in solution, wherein based on the mixing, the anionic polymer and cationic polymer form a coacervate complex that quenches light emission of the fluorescent functional group, and wherein the cationic polymer reacts with a known biomarker. At 2906, the coacervate complex can be mixed with a biological fluid sample, and at 2908, presence of the known biomarker can be detected in the biological fluid sample based on an amount of the light emission detected after the mixing of the coacervate complex with the biological fluid sample.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In this regard, with respect to any figure or numerical range for a given characteristic, a figure or a parameter from one range may be combined with another figure or a parameter from a different range for the same characteristic to generate a numerical range. Other than in the operating examples, or where otherwise indicated, all numbers, values and/or expressions referring to quantities of ingredients, reaction conditions, etc., used in the specification and claims are to be understood as modified in all instances by the term "about."

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A therapeutic agent, comprising:

a cationic polymer and an anionic polymer, wherein the cationic polymer and the anionic polymer form a coacervate complex in a fluid;

wherein the anionic polymer comprises a polycarbonate backbone comprising anionic functional groups bound to the polycarbonate backbone; and wherein the cationic polymer comprises:

a polymer backbone;

at least one therapeutic functional group bound to the polymer backbone, wherein the at least one therapeutic functional group provides at least one of an antimicrobial functionality or an anticancer functionality of the therapeutic agent; and a biotin-based functional group bound to an end of the polymer backbone, wherein the biotin-based functional group being bound to the end of the polymer backbone improves the at least one of the antimicrobial functionality or the anticancer functionality of the therapeutic agent.

2. The therapeutic agent of claim 1, wherein the at least one therapeutic functional group comprises guanidinium moieties.

3. The therapeutic agent of claim 1, wherein the therapeutic agent facilitates necrosis of bacteria cells.

4. The therapeutic agent of claim 1, wherein the therapeutic agent facilitates autophagy of cancer cells.

5. The therapeutic agent of claim 1, wherein the biotin-based functional group comprises biotinol.

6. The therapeutic agent of claim 1, wherein the at least one therapeutic functional group comprises at least one member selected from the group consisting of: a guanidinium moiety, a thiol moiety, and a carboxylic acid moiety.

7. The therapeutic agent of claim 1, wherein cationic polymer has a chemical structure characterized by Formula I:

Formula I

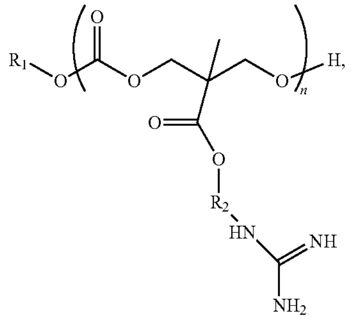

wherein n represents an integer between 10 and 50, wherein $R_1$ comprises the biotin-based functional group, and wherein $R_2$ comprises a spacer group.

8. The therapeutic agent of claim 1, wherein the cationic polymer has a chemical structure characterized by Formula II:

Formula II

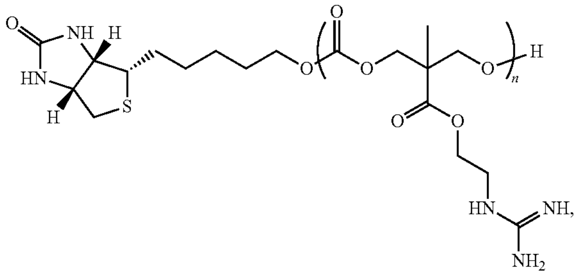

wherein n represents an integer between 10 and 50.

9. The therapeutic agent of claim 1, wherein the coacervate complex exhibits reduced hemotoxicity relative to the cationic polymer alone.

10. The therapeutic agent of claim 1, wherein the anionic functional groups are selected from the group consisting of: sulfonate groups, carboxylate groups, and phosphoric acid groups.

11. The therapeutic agent of claim 1, wherein the anionic polymer comprises a polyethylene glycol tail.

12. The therapeutic agent of claim 11, wherein the polyethylene glycol tail is formed around the cationic polymer of the coacervate complex.

13. The therapeutic agent of claim 1, wherein the coacervate complex comprises a circular or spherical nanoparticle structure.

14. The therapeutic agent of claim 1, wherein the coacervate complex comprises a nanoparticle structure having a size from about 70 nanometers (nm) to about 200 nm.

15. A therapeutic, agent, comprising:

a cationic polymer and an anionic polymer;

wherein the cationic polymer and the anionic polymer form a coacervate complex in a fluid;

wherein the anionic polymer comprises a polycarbonate backbone comprising anionic functional groups bound to the polycarbonate backbone; and wherein the cationic polymer has a chemical structure characterized by Formula I:

Formula I

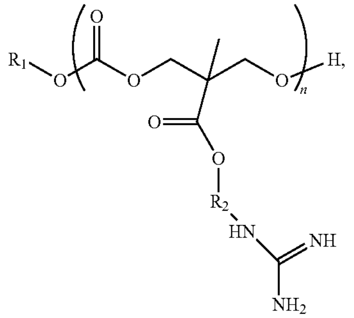

wherein n represents an integer between 10 and 50, wherein $R_1$ comprises a biotin-based functional group that improves at least one of an antimicrobial functionality or an anticancer functionality provided by at least one therapeutic functional group of the cationic polymer, and wherein $R_2$ comprises a spacer group.

16. The therapeutic agent of claim 15, wherein the therapeutic agent is an anticancer agent.

17. The therapeutic agent of claim 15, wherein the therapeutic agent is an antimicrobial agent.

18. A therapeutic agent, comprising:

a cationic polymer and an anionic polymer;

wherein the cationic polymer and the anionic polymer form a coacervate complex in a fluid;

wherein the anionic polymer comprises a polycarbonate backbone comprising anionic functional groups bound to the polycarbonate backbone; and wherein the cationic polymer has a chemical structure characterized by Formula I:

Formula I
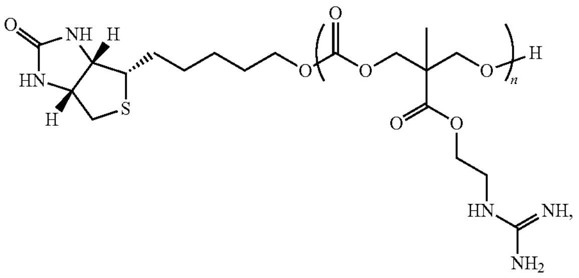
wherein n represents an integer between 10 and 50, and where the therapeutic gent is effective against a plurality of different cancer cell lines.
19. The therapeutic agent of claim 18, wherein the plurality of different cancer cell lines comprises cancer cell line BT-474.
* * * * *